United States Patent
Mailliet et al.

(10) Patent No.: US 6,291,679 B1
(45) Date of Patent: Sep. 18, 2001

(54) PROCESS FOR PREPARING BENZOPERHYDROISOINDOLE COMPOUNDS

(75) Inventors: Patrick Mailliet, Fontenay Sous Bois; Christophe Salagnad, Ormesson sur Marne, both of (FR)

(73) Assignee: Rhone-Poulenc Rorer S.A., Antony (FR)

( * ) Notice: Subject to any disclaimer, the term of this patent is extended or adjusted under 35 U.S.C. 154(b) by 0 days.

(21) Appl. No.: 09/360,646

(22) Filed: Jul. 26, 1999

(30) Foreign Application Priority Data

Jul. 22, 1999 (FR) .................................................. 99 09508

(51) Int. Cl.[7] .................................................. C07D 209/58
(52) U.S. Cl. ........................................ 546/276.7; 548/426
(58) Field of Search ........................... 548/426; 546/276.7

(56) References Cited

U.S. PATENT DOCUMENTS

| 6,013,662 | * | 1/2000 | Bourzat et al. | 514/410 |
| 6,124,465 | * | 9/2000 | Bourzat et al. | 546/276.7 |

FOREIGN PATENT DOCUMENTS

| 2736641 | 1/1997 | (FR) . |
| 2772764 | 6/1999 | (FR) . |
| WO/9512612 | 5/1995 | (WO) . |
| WO/9703050 | 1/1997 | (WO) . |

* cited by examiner

*Primary Examiner*—Joseph K. McKane
*Assistant Examiner*—Sonya Wright
(74) *Attorney, Agent, or Firm*—Finnegan, Henderson, Farabow, Garrett & Dunner, L.L.P.

(57) ABSTRACT

The present invention relates to a novel process for the preparation of benzoperhydroisindole compounds.

12 Claims, No Drawings

PROCESS FOR PREPARING BENZOPERHYDROISOINDOLE COMPOUNDS

The present invention relates to a novel process for the preparation of compounds of benzoperhydroisoindole type of general formula (I):

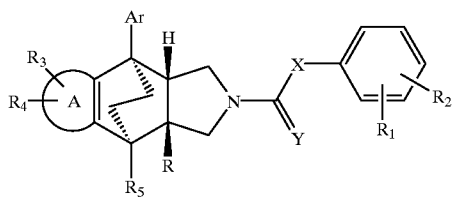

The compounds of general formula and their activity as farnesyl transferase inhibitors are disclosed in Applications WO 98/29390 and FR 2,772,764.

The protein farnesyl transferase is an enzyme which catalyzes the transfer of the farnesyl group from farnesyl pyrophosphate (FPP) to the terminal cysteine residue of the tetrapeptide sequence CAAX of a certain number of proteins and in particular of the p21Ras protein, which expresses the ras oncogene. The ras (H-, N- or K-ras) oncogene is known to play a key role in cell signaling pathways and cell division processes. The mutation of the ras oncogene or its overexpression is often associated with human cancer: the mutated p21Ras protein is found in many human cancers and in particular in more than 50% of cancers of the colon and 90% of cancers of the pancreas (Kohl et al., Science, 260, 1834–1837, 1993). The inhibition of farnesyl transferase and consequently of the farnesylation of the p21Ras protein blocks the ability of the mutated p21Ras protein to induce cell proliferation and to transform normal cells into cancerous cells. Moreover, it has been demonstrated that farnesyl transferase inhibitors are also active with respect to tumoral cell lines which do not express mutated or overexpressed ras but which exhibit the mutation of an oncogene or the overexpression of an oncoprotein, the signaling pathway of which uses the farnesylation of a protein, such as a normal ras (Nagasu et al., Cancer Research, 55, 5310–5314, 1995; Sepp-Lorenzino et al., Cancer Research, 55, 5302–5309, 1995) or such as rhoB (Wei et al., Molecular and Cellular Biology, 19, 1831–1840, 1999). The inhibitors of Farnesyl transferase are inhibitors of cell proliferation and consequently antitumor and antileukemic agents.

The process for the preparation of the compounds of general formula (I) is also disclosed in Applications WO 98/29390 and FR 2,772,764: According to this process, the final compounds are obtained in the form of a racemic mixture, which requires a subsequent separation of the enantiomers constituting this mixture. The result of this is therefore a problematic additional stage, the consequence of which is to decrease the overall yield with respect to the starting material and to each of the reactants.

According to the present invention, a process has been discovered which makes it possible to obtain the products of general formula (I) directly in the form of optical isomers, without employing a separation. This process comprises an enzymatic stage which makes possible the enantiomeric resolution of the compounds of general formula (I).

The present invention therefore relates to a process for the preparation of the optical isomers of the compounds disclosed in Applications WO 98/29390 and FR 2,772,764, which are incorporated here by reference.

The compounds capable of being prepared by the process according to the present invention are the compounds of general formula (I):

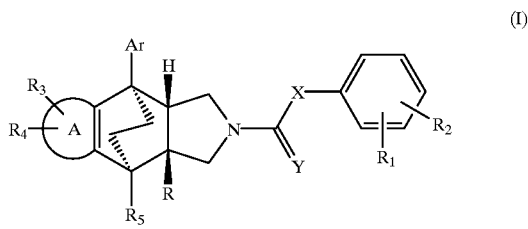

in which:

A represents:
either a phenyl radical fused with the isoindole nucleus, and in this case:
$R_3$ and $R_4$, which are identical or different, represent a hydrogen or halogen atom or an alkyl, hydroxyl, alkyloxy, alkylcarbonyloxy, mercapto, alkylthio, alkylsulfonyl or alkylsulfinyl, amino, alkylamino or dialkylamino, alkyloxycarbonylamino, carboxyl, alkyloxycarbonyl, carbamoyl, alkylcarbamoyl or dialkylcarbamoyl, formyl, alkylcarbonyl, cyano or trifluoromethyl radical,
preferably, either $R_3$ and $R_4$ each represent a hydrogen atom or alternatively one of the $R_3$ or $R_4$ symbols represents a hydrogen atom and the other of the $R_3$ or $R_4$ symbols represents a methoxy radical, more advantageously at the 5 position of the benzoperhydroisoindole nucleus;
very advantageously, $R_3$ and $R_4$ each represent a hydrogen atom;
with, for all of the radicals possessing an alkyl group provided in the definition of $R_3$ and $R_4$, alkyl comprising 1 to 4 carbon atoms,
or A represents a monocyclic or condensed bi- or tricyclic system in which each saturated or unsaturated ring comprises from 4 to 7 members and in which at least one of the rings comprises from 1 to 4 identical or different heteroatoms chosen independently from nitrogen, oxygen and sulfur atoms; this optionally substituted heterocyclic system can be condensed with the isoindole nucleus by any 2 of its adjacent atoms; A preferably represents a 5- to 9-membered aromatic mono- or bicyclic system comprising a nitrogen or sulfur atom; it also being possible for A to be chosen, without implied limitation, from the following radicals: thienyl, furyl, pyrrolyl, pyrazolyl, imidazolyl, pyridyl, pyrazinyl, pyrimidinyl, pyridazinyl, benzofuranyl, benzothienyl, chromenyl, indolyl or quinolyl, as well as their iso isomers;
preferably, A represents a thienyl or indolyl radical; advantageously, according to the invention, A represents thienyl;
and in this case $R_3$ and $R_4$ represent a hydrogen atom,
Ar represents
a phenyl radical optionally substituted by one or more atoms or radicals, which are identical or different, chosen from halogen atoms and the following radicals: alkyl comprising 1 to 4 carbon atoms, such as methyl, alkenyl comprising 2 to 4 carbon atoms, hydroxyl, mercapto, alkylthio, alkylsulfonyl or alkylsulfinyl, amino, alkylamino or dialkylamino, formyl, alkylcarbonyl, carboxyl, alkoxycarbonyl, carbamoyl, alkylcarbamoyl or dialkylcarbamoyl, cyano or trifluoromethyl, or alkoxy comprising 1 to 4 carbon atoms, such as methoxy, the alkyl portion of which is optionally perhalogenated, such as trifluoromethoxy, or a phenyl radical condensed with a 4- to 7-membered heterocycle comprising one or more heteroatoms chosen from oxygen, nitrogen and sulfur atoms, it being possible for the bicyclic system thus formed to be in particular chosen from 2,3-dihydro-1,4-benzodioxin-6-yl or 2,3-dihydrobenzofuran-5-yl or 2,3-dihydrobenzopyran-6-yl or benzothienyl radicals or a polycyclic aromatic or nonaromatic radical, such as 1- or 2-naphthyl or 5-indanyl or 1,2,3,4-tetrahydronaphth-6-yl a 5- to 12-membered heterocyclic aromatic or nonaromatic radical incorporating one or more heteroatoms chosen from oxygen, nitrogen and sulfur atoms, bonded to the condensed ring via a carbon-carbon bond, said radical being substituted, if appropriate, by one or more atoms or radicals, which are identical or different, chosen from halogen atoms and the following radicals: alkyl, alkenyl comprising 2 to 4 carbon atoms, hydroxyl, alkoxy comprising 1 to 4 carbon atoms, mercapto, alkylthio, alkylsulfonyl or alkylsulfinyl, amino, alkylamino or dialkylamino, formyl, alkylcarbonyl, carboxyl, alkoxycarbonyl, carbamoyl, alkylcarbamoyl or dialkylcarbamoyl, cyano or trifluoromethyl, preferably Ar represents a 2,3-dihydro-1,4-benzodioxin-6-yl or 2,3-dihydrobenzofuran-5-yl or benzothienyl radical or a phenyl radical optionally substituted at the 2 and/or 4 position, preferably by a halogen atom or a methyl, trifluoromethyl or methoxy radical; in particular, the 2,3-dihydro-1,4-benzodioxin-6-yl or benzothienyl radical; very advantageously, Ar represents a phenyl radical optionally substituted at the 4 position by a methyl radical or at the 2,4 position by a halogen atom, with, for all of these radicals, alkyl comprising 1 to 4 carbon atoms, R represents a radical of general formula

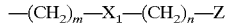

in which
X$_1$ represents a single bond or an oxygen or sulfur atom,
m represents an integer equal to 0 or 1,
n represents an integer equal to 0, 1 or 2,
one or more methylene radicals can be substituted by a carboxyl, alkoxycarbonyl, carbamoyl, alkylcarbamoyl, dialkylcarbamoyl, amino, alkylamino or dialkylamino radical with, for all of these radicals, alkyl comprising 1 to 4 carbon atoms, Z represents
a carboxyl radical,
a COOR$_6$ radical, in which R$_6$ represents a straight or branched alkyl radical comprising 1 to 3 carbon atoms, such as the methyl, or
a radical of formula CON(R$_7$) (R$_8$) in which
R$_7$ represents a hydrogen atom or a straight or branched alkyl radical comprising 1 to 6 carbon atoms and
R$_8$ represents
a hydrogen atom,
a hydroxyl radical,
an arylsulfonyl radical, such as phenylsulfonyl, optionally substituted by one or more atoms or radicals, which are identical or different, chosen from halogen atoms and alkyl or alkyloxy radicals with, for these radicals, alkyl comprising 1 to 4 carbon atoms,
a 5- to 7-membered heterocycle incorporating one or more heteroatoms chosen from nitrogen, oxygen or sulfur atoms, it being possible for said heterocycle to be bonded via a heteroatom,
an amino radical optionally substituted by one or two radicals, which are identical or different, chosen from the following radicals:
alkyl comprising 1 to 4 carbon atoms,
aryl, such as phenyl, optionally substituted by one or more radicals, which are identical or different, chosen from alkyl or alkyloxy radicals with, for these radicals, alkyl comprising 1 to 4 carbon atoms,
5- to 7-membered heterocyclyl comprising one or more heteroatoms chosen from nitrogen, oxygen and sulfur atoms,
arylcarbonyl, such as benzoyl, optionally substituted by one or more radicals, which are identical or different, chosen from alkyl or alkyloxy radicals with, for these radicals, alkyl comprising 1 to 4 carbon atoms,
an alkyloxy radical comprising 1 to 6 straight- or branched-chain carbon atoms optionally substituted by a phenyl radical,
a straight or branched alkyl radical comprising 1 to 6 carbon atoms, such as methyl, optionally substituted by an amino, alkylamino, dialkylamino, hydroxyl, alkoxy comprising 1 to 4 carbon atoms, mercapto, alkylthio, alkyloxycarbonyl, carboxyl or cyano radical, an optionally substituted mono- or polycyclic aromatic radical having from 5 to 12 ring members which may or may not incorporate one or more heteroatoms chosen from oxygen, nitrogen and sulfur atoms, it being possible for said aromatic radical to be in particular the 2- or 3- or 4-pyridyl radical, preferably 3-pyridyl or 4-pyridyl, or the N-oxide of pyridine, or it also being possible for said aromatic radical to be a phenyl radical optionally substituted by one or more halogen atoms or by one or more hydroxyl, amino or trifluoromethyl groups or by one or more alkyl or alkenyl, alkoxy, alkylthio, alkylamino, alkylcarbonyl or C2 to C4 alkoxycarbonyl, carbamoyl, alkylcarbamoyl or dialkylcarbamoyl, the alkyl part of which comprises 1 to 8 carbon atoms, or formyl radicals, or alternatively a 1- or 2-naphthyl radical, or,
preferably, R represents a carboxyl radical or a —COOMe radical or alternatively a —CON(R$_7$) (R$_8$) radical in which, when R$_7$ represents a hydrogen atom, R$_8$ represents a methyl radical substituted by the 3-pyridyl radical; very advantageously, R represents a carboxyl radical; very particularly advantageously, R represents a —CON(R$_7$)(R$_8$) radical in which, when R$_7$ represents a hydrogen atom, R$_8$ represents a methyl radical substituted by the 3-pyridyl radical;

Z represents
a PO(OR$_9$)$_2$ radical in which R$_9$ represents a hydrogen atom or a straight or branched alkyl radical comprising 1 to 6 carbon atoms, or
an —NH—CO—T radical in which T represents a hydrogen atom or a straight or branched alkyl radical comprising 1 to 6 carbon atoms optionally substituted by an amino, carboxyl, alkyloxycarbonyl, hydroxyl, alkyloxy, mercapto or alkylthio radical, or alternatively

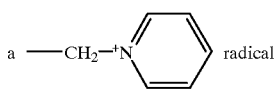

having an anion, such as trifluoromethanesulfonate, as counterion, with, for all of the radicals possessing an alkyl group provided in the definition of Z, alkyl comprising 1 to 4 carbon atoms, $R_1$ and $R_2$, which are identical or different, represent a hydrogen atom, a halogen atom or an alkyl radical, an alkyloxy radical, such as methoxy, each optionally substituted by a dialkylamino radical, each alkyl part of which comprises 1 to 4 carbon atoms or forms, with the nitrogen atom, a saturated heterocycle containing 5 or 6 ring members, an alkylthio radical or an alkyloxycarbonyl radical, or alternatively situated at the ortho position with respect to one another, $R_1$ and $R_2$ form a saturated or unsaturated heterocycle comprising 1 or 2 heteroatoms chosen from nitrogen and oxygen, optionally substituted by a halogen atom or by an alkyl or alkyloxy radical, preferably, one of the $R_1$ or $R_2$ symbols represents a hydrogen atom and the other of the symbols represents a methoxy radical, more advantageously attached at the ortho position of the phenyl ring, with, for all of the radicals possessing an alkyl group provided in the definition of $R_1$ and $R_2$, alkyl comprising 1 to 4 carbon atoms, $R_5$ represents a hydrogen atom or an alkyl radical or an alkylthio radical, with, for the definition of $R_5$, alkyl comprising 1 to 4 carbon atoms; preferably, $R_5$ represents a hydrogen atom or a methyl radical;

very advantageously, $R_5$ represents a hydrogen atom;

X represents an oxygen or sulfur atom or one of the following groups: —NH—, —CO—, methylene, alken-1,1-diyl, such as vinyldiyl, or cycloalkan-1,1-diyl comprising 3 to 6 carbon atoms, preferably, X represents a methylene or vinyldiyl group, in a particularly advantageous way, X represents the vinyldiyl group, and Y represents an oxygen or sulfur atom, preferably, Y represents an oxygen atom, their optical isomers, as well as the salts of the product of general formula (I).

In the preceding and following definitions, the "alkyl comprising 1 to 8 carbon atoms" radicals or portions defines the methyl, ethyl, propyl, butyl, pentyl, hexyl, heptyl and octyl radicals and the corresponding iso, sec and tert isomers, the "alkyl comprising 1 to 6 carbon atoms" radicals or portions defines the methyl, ethyl, propyl, butyl, pentyl and hexyl radicals and the corresponding iso, sec and tert isomers, the "alkyl comprising 1 to 4 carbon atoms" radicals or portions defines the methyl, ethyl, propyl and butyl radicals and the corresponding iso, sec and tert isomers, "alkenyls comprising 2 to 4 carbon atoms" defines the vinyl, allyl, propene-2-yl, butene-1-yl, butene-2-yl and butene-3-yl radicals and the corresponding iso isomers, "alkoxy comprising 1 to 4 carbon atoms" defines the methoxy, ethoxy, propoxy and butoxy radicals and the corresponding iso, sec and tert isomers, "C2 to C4 alkoxycarbonyl" defines the metoxycarbonyl, ethoxycarbonyl and propoxycarbonyl radicals and the corresponding iso, sec and tert isomers.

Preferably, the compounds capable of being prepared by the process according to the invention exhibit a general formula (I) in which:

A represents either a phenyl radical fused to the isoindole ring and $R_3$ and $R_4$ represent a hydrogen atom, or a thienyl radical and $R_3$ and $R_4$ represent a hydrogen atom, Ar represents a 2,3-dihydro-1,4-benzodioxin- 6-yl or 2,3-dihydrobenzofuran-5-yl or benzothien-2-yl radical or a phenyl radical optionally substituted at the 4 position, preferably by a methyl, trifluoromethyl or methoxy radical or by a chlorine or bromine atom, or at the 3-, 4- or 2-, 4-position by a chlorine atom;

R represents a carboxyl radical or a —COOMe radical or alternatively a —CON($R_7$) ($R_8$) radical in which, when $R_7$ represents a hydrogen atom, $R_8$ represents a methyl radical substituted by the 3-pyridyl radical, one of the $R_1$ or $R_2$ symbols represents a hydrogen atom and the other of the symbols represents a methoxy radical, more advantageously attached at the ortho position of the phenyl ring, $R_5$ represents a hydrogen atom or a methyl radical, X represents a methylene or vinyldiyl group, Y represents an oxygen atom;

in the form of their optical isomers, as well as their salts.

According to the invention, the compounds of general formula (I) are preferably provided in the dextrorotatory form.

Mention may be made, according to the invention, of any compound of general formula (I) individually selected from:

methyl (3aRS,4SR,9SR,9aRS)-4,9-ethano-2-[2-(2-methoxyphenyl)propenoyl]-9-(4-methylphenyl)-2,3,3a,4,9,9a-hexahydro-1H-benzo[f]isoindole-3a-carboxylate (3aRS,4SR,9SR,9aRS)-4,9-ethano-2-(2-methoxyphenyl)-propenoyl-9-(4-methylphenyl)-2,3,3a,4,9,9a-hexahydro-1H-benzo[f]isoindole-3a-carboxylic acid (3aRS,4SR,9SR,9aRS)-4,9-ethano-2-[(2-methoxyphenyl)-acetyl]-9-(4-methylphenyl)-2,3,3a,4,9,9a-hexahydro-1H-benzo[f]isoindole-3a-carboxylic acid (3aRS,4SR,9SR,9aRS)-4,9-ethano-9-(4-methoxyphenyl)-2-[(2-methoxyphenyl)acetyl]-2,3,3a,4,9,9a-hexahydro-1H-benzo[f]isoindole-3a-carboxylic acid (3aRS,4SR,9SR,9aRS)-4,9-ethano-2-[(2-methoxyphenyl)-acetyl]-9-(4-methylsulfanylphenyl)-2,3,3a,4,9,9a-hexahydro-1H-benzo[f]isoindole-3a-carboxylic acid (3aRS,4SR,9SR,9aRS)-4,9-ethano-9-(4-fluorophenyl)-2-[(2-methoxyphenyl)acetyl]-2,3,3a,4,9,9a-hexahydro-1H-benzo[f]isoindole-3a-carboxylic acid (3aRS,4SR,9SR,9aRS)-4,9-ethano-2-[(2-methoxyphenyl)-acetyl]-9-(3-methylphenyl)-2,3,3a,4,9,9a-hexahydro-1H-benzo[f]isoindole-3a-carboxylic acid (3aRS,4SR,9SR,9aRS)-4,9-ethano-9-(3-methoxyphenyl)-2-[(2-methoxyphenyl)acetyl]-2,3,3a,4,9,9a-hexahydro-1H-benzo[f]isoindole-3a-carboxylic acid methyl (3aRS,4SR,9SR,9aRS)-9-(3,4-dimethylphenyl)-4,9-ethano-2-[(2-methoxyphenyl)acetyl]-2,3,3a,4,9,9a-hexahydro-1H-benzo[f]isoindole-3a-carboxylate (3aRS,4SR,9SR,9aRS)-9-(3,4-dimethylphenyl)-4,9-ethano-2-[(2-methoxyphenyl)acetyl]-2,3,3a,4,9,9a-hexahydro-1H-benzo[f]isoindole-3a-carboxylic acid (3aRS,4SR,9SR,9aRS)-3a-N-benzylcarbamoyl-4,9-ethano-2 -[2-(2-methoxyphenyl)propenoyl]-9-(4-methylphenyl)-2,3,3a,4,9,9a-hexahydro-1H-benzo[f]isoindole (3aRS,4SR,9SR,9aRS)-3a-carbamoyl-4,9-ethano-2-[2-(2-methoxyphenyl)propenoyl]-9-(4-methylphenyl)-2,3,3a,4,9,9a-hexahydro-1H-benzo[f]isoindole benzyl (3aRS,4SR,9SR,9aRS)-4,9-ethano-2-[2-(2-methoxyphenyl)

propenoyl]-9-(4-methylphenyl)-2,3,3a,4,9,9a-hexahydro-1H-benzo[f]isoindole-3a-hydroxamate (3aRS,4SR,9SR,9aRS)-4,9-ethano-2-[2-(2-methoxyphenyl)-propenoyl]-9-(4-methylphenyl)-,3,3a,4,9,9a-hexahydro-1H-benzo[f]isoindole-3a-hydroxamic acid (3aRS,4SR,9SR,9aRS)-4,9-ethano-2-[2-(2-methoxyphenyl)propenoyl]-9-(4-methylphenyl)-2,3,3a,4,9,9a-hexahydro-1H-benzo[f]isoindole-3a-N-(3-pyridylmethyl)-carboxamide (3aRS,4SR,9SR,9aRS)-4,9-ethano-2-[2-(2-methoxyphenyl)propenoyl]-9-(4-methylphenyl)-2,3,3a,4,9,9a-hexahydro-1H-benzo[f]isoindole-3a-N-(4-pyridylmethyl)-carboxamide methyl (3aRS,4SR,9SR,9aRS)-4,9-ethano-2-[2-(2-methoxyphenyl)propenoyl]-9-(4-methylphenyl)-2,3,3a,4,9,9a-hexahydro-1H-benzo[f]isoindole-3a-hydroxamate (3aRS,4SR,9SR,9aRS)-4,9-ethano-2-[2-(2-methoxyphenyl)propenoyl]-9-(4-methylphenyl)-2,3,3a,4,9,9a-hexahydro-1H-benzo[f]isoindole-3a-N',N'-dimethyl-carbohydrazide (3aRS,4SR,9SR,9aRS)-4,9-ethano-2-[2-(2-methoxyphenyl)propenoyl]-9-(4-methylphenyl)-2,3,3a,4,9,9a-hexahydro-1H-benzo[f]isoindole-3a-N'-phenylcarbohydrazide (3aRS,4SR,9SR,9aRS)-4,9-ethano-2-[2-(2-methoxyphenyl)propenoyl]-9-(4-methylphenyl)-2,3,3a,4,9,9a-hexahydro-1H-benzo[f]isoindole-3a-N',N'-pentamethylene-carbohydrazide (3aRS,4SR,9SR,9aRS)-4,9-ethano-2-[2-(methoxyphenyl)propenoyl]-9-(4-methylphenyl)-3a-phenylsulfonylaminocarbonyl-2,3,3a,4,9,9a-hexahydro-1H-benzo[f]isoindole (3aRS,4SR,9SR,9aRS)-4,9-ethano-2-[2-(2-methoxyphenyl)propenoyl]-9-(4-methylphenyl)-2,3,3a,4,9,9a-hexahydro-1H-benzo[f]isoindole-3a-N-(N-oxo-3pyridyl)-methylcarboxamide (3aRS,4SR,9SR,9aRS)-4,9-ethano-2-[2-(2-methoxyphenyl)propenoyl]-9-(4-methylphenyl)-2,3,3a,4,9,9a-hexahydro-1H-benzo[f]isoindole-3a-N'-(4-methoxyphenyl)-carbohydrazide (3aRS,4SR,9SR,9aRS)-4,9-ethano-2-[2-(2-methoxyphenyl)propenoyl]-9-(4-methylphenyl)-2,3,3a,4,9,9a-hexahydro-1H-benzo[f]isoindole-3a-N'-methyl,N'-phenylcarbohydrazide (3aRS,4SR,9SR,9aRS)-4,9-ethano-2-[2-(2-methoxyphenyl)propenoyl]-9-(4-methylphenyl)-2,3,3a,4,9,9a-hexahydro-1H-benzo[f]isoindole-3a-N'-(2-methylphenyl)carbohydrazide methyl (3aRS,4SR,9SR,9aRS)-9-(2,3-dihydro-1,4-benzodioxin-6-yl)-4,9-ethano-2-[2-(2-methoxyphenyl)-propenoyl]-2,3,3a,4,9,9a-hexahydro-1H-benzo[f]-isoindole-3a-carboxylate (3aRS,4SR,9SR,9aRS)-9-(2,3-dihydro-1,4-benzodioxin-6-yl)-4,9-ethano-2-[2-(2-methoxyphenyl)propenoyl]-2,3,3a,4,9,9a-hexahydro-1H-benzo[f]isoindole-3a-carboxylic acid (3aRS,4SR,9SR,9aRS)-9-(2,3-dihydro-1,4-benzodioxin-6-yl)-4,9-ethano-2-[2-(2-methoxyphenyl)propenoyl]-2,3,3a,4,9,9a-hexahydro-1H-benzo[f]isoindole-3a-[N-(3-pyridylmethyl)carboxamide (3aRS,4SR,9SR,9aRS)-9-(2,3-dihydro-1,4-benzodioxin-6-yl)-4,9-ethano-2-[2-(2-methoxyphenyl)propenoyl]-2,3,3a,4,9,9a-hexahydro-1H-benzo[f]isoindole-3a-N-(2-thienylmethyl)carboxamide (3aRS,4SR,9SR,9aRS)-4,9-ethano-2-[(2-methoxyphenyl)-acetyl]-9-(3,4,5-trimethylphenyl)-2,3,3a,4,9,9a-hexahydro-1H-benzo[f]isoindole-3a-carboxylic acid (3aRS,4SR,9SR,9aRS)-4,9-ethano-2-[2-(2-methoxyphenyl)-propenoyl]-9-(2-methylphenyl)-2,3,3a,4,9,9a-hexahydro-1H-benzo[f]isoindole-3a-carboxylic acid methyl (3aRS,4SR,9SR,9aRS)-4,9-ethano-2-[2-(2-methoxyphenyl)propenoyl]-9-(4-trifluoromethylphenyl)-2,3,3a,4,9,9a-hexahydro-1H-benzo[f]isoindole-3a-carboxylate (3aRS,4SR,9SR,9aRS)-4,9-ethano-2-[2-(2-methoxyphenyl)-propenoyl]-9-(4-trifluoromethylphenyl)-2,3,3a,4,9,9a-hexahydro-1H-benzo[f]isoindole-3a-carboxylic acid (3aRS,4SR,9SR,9aRS)-4,9-ethano-2-[2-(2-methoxyphenyl)-propenoyl]-9-(4-trifluoromethylphenyl)-2,3,3a,4,9,9a-hexahydro-1H-benzo[f]isoindole-3a-N-(4-pyridylmethyl)carboxamide (3aRS,4SR,9SR,9aRS)-4,9-ethano-2-[2-(2-methoxyphenyl)-propenoyl]-9-(4-trifluoromethylphenyl)-2,3,3a,4,9,9a-hexahydro-1H-benzo[f]isoindole-3a-N'-benzoylcarbohydrazide (3aRS,4SR,9SR,9aRS)-4,9-ethano-2-[2-(2-methoxyphenyl)-propenoyl]-9-(4-trifluoromethylphenyl)-2,3,3a,4,9,9a-hexahydro-1H-benzo[f]isoindole-3a-N'-phenylcarbohydrazide methyl (3aRS,4SR,9SR,9aRS)-4,9-ethano-2-[2-(2-methoxyphenyl)propenoyl]-9-(2-naphthyl)-2,3,3a,4,9,9a-hexahydro-1H-benzo[f]isoindole-3a-carboxylate (3aRS,4SR,9SR,9aRS)-4,9-ethano-2-[2-(2-methoxyphenyl)-propenoyl]-9-(2-naphthyl)-2,3,3a,4,9,9a-hexahydro-1H-benzo[f]isoindole-3a-carboxylic acid methyl (3aRS,4SR,9SR,9aRS)-4,9-ethano-2-[2-(2-methoxyphenyl)propenoyl]-9-(5-methyl-2-thienyl)-2,3,3a,4,9,9a-hexahydro-1H-benzo[f]isoindole-3a-carboxylate (3aRS,4SR,9SR,9aRS)-4,9-ethano-2-[2-(2-methoxyphenyl)-propenoyl]-9-(5-methyl-2-thienyl)-2,3,3a,4,9,9a-hexahydro-1H-benzo[f]isoindole-3a-carboxylic acid methyl (3aRS,4SR,9SR,9aRS)-9-(4-bromophenyl)-4,9-ethano-2-[2-(2-methoxyphenyl)propenoyl]-2,3,3a,4,9,9a-hexahydro-1H-benzo[f]isoindole-3a-carboxylate (3aRS,4SR,9SR,9aRS)-9-(4-bromophenyl)-4,9-ethano-2-[2-(2-methoxyphenyl)propenoyl]-2,3,3a,4,9,9a-hexahydro-1H-benzo[f]isoindole-3a-carboxylic acid (3aRS,4SR,9SR,9aRS)-9-(3,4-dichlorophenyl)-4,9-ethano-2-[2-(2-methoxyphenyl)propenoyl]-2,3,3a,4,9,9a-hexahydro-1H-benzo[f]isoindole-3a-carboxylic acid methyl (3aRS,4SR,9SR,9aRS)-4,9-ethano-2-[2-(2-methoxyphenyl)propenoyl]-9-(4-chlorophenyl)-2,3,3a,4,9,9a-hexahydro-1H-benzo[f]isoindole-3a-carboxylate (3aRS,4SR,9SR,9aRS)-9-(4-chlorophenyl)-4,9-ethano-2-[2-(2-methoxyphenyl)propenoyl]-2,3,3a,4,9,9a-hexahydro-1H-benzo[f]isoindole-3a-carboxylic acid (3aRS,4SR,9SR,9aRS)-4,9-ethano-2-[2-(2-methoxyphenyl)-propenoyl]-9-(4-methoxy-3-methylphenyl)-2,3,3a,4,9,9a-hexahydro-1H-benzo[f]isoindole-3a-carboxylic acid methyl (3aRS,4SR,9SR,9aRS)-4,9-ethano-2-[2-(2-methoxyphenyl)propenoyl]-9-(3-indolyl)-2,3,3a,4,9,9a-hexahydro-1H-benzo[f]isoindole-3a-carboxylate (3aRS,4SR,9SR,9aRS)-4,9-ethano-9-(4-isopropylphenyl)-2-[(2-methoxyphenyl)acetyl]-2,3,3a,4,9,9a-hexahydro-1H-benzo[f]isoindole-3a-carboxylic acid (3aRS,4SR,9SR,9aRS)-4,9-ethano-9-(4-isopropylphenyl)-2-[2-(2-methoxyphenyl)propenoyl]-2,3,3a,4,9,9a-hexahydro-1H-benzo[f]isoindole-3a-carboxylic acid methyl (3aRS,4SR,9SR,9aRS)-4,9-ethano-2-[2-(2-methoxyphenyl)propenoyl]-9-(3-thienyl)-2,3,3a,4,9,9a-hexahydro-1H-benzo[f]isoindole-3a-carboxylate methyl (3aRS,4SR,9SR,9aRS)-4,9-ethano-9-(4-ethylphenyl)-2-[2-(2-methoxyphenyl)propenoyl]-2,3,3a,4,9,9a-hexahydro-1H-benzo[f]isoindole-3a-carboxylate (3aRS,4SR,9SR,9aRS)-4,9-ethano-9-(4-ethylphenyl)-2-[2-(2-methoxyphenyl)propenoyl]-2,3,3a,4,9,9a-hexahydro-1H-benzo[f]isoindole-3a-carboxylic acid methyl (3aRS,4SR,9SR,9aRS)-9-(2,3-dihydrobenzofuran-5-yl)-4,9-ethano-2-[2-(2-methoxyphenyl)propenoyl]-2,3,3a,4,9,9a-hexahydro-1H-benzo[f]isoindole-3a-carboxylate methyl (3aRS,4SR,9SR,9aRS)-9-(2,3-dihydrobenzofuran-5-yl)-4,9-ethano-2-[2-(2-methoxyphenyl)propenoyl]-2,3,3a,4,9,9a-hexahydro-1H-benzo[f]isoindole-3a-carboxylate acid (3aRS,4SR,9SR,9aRS)-9-(2,3-dihydrobenzofuran-5-yl)-4,9-ethano-2-[2-(2-methoxyphenyl)propenoyl)]-2,3,3a,4,9,9a-hexahydro-1H-benzo[f]isoindole-3a-N-(3-pyridylmethyl)-carboxamide methyl (3aRS,4SR,9SR,9aRS)-4,9-ethano-9-(4-fluorophenyl)-2-[2-(2-methoxyphenyl)propenoyl]-2,3,3a,4,9,9a-hexahydro-1H-benzo[f]isoindole-3a-carboxylate (3aRS,4SR,9SR,9aRS)-4,9-ethano-9-(4-fluorophenyl)-2-[2-(2-methoxyphenyl)propenoyl]-2,3,3a,4,9,9a-hexahydro-1H-benzo[f]isoindole-3a-carboxylic acid methyl (3aRS,4SR,9SR,9aRS)-9-(4-chloro-3-fluorophenyl)-4,9-ethano-2-[2-(2-methoxyphenyl)propenoyl]-2,3,3a,4,9,9a-hexahydro-1H-benzo[f]isoindole-3a-carboxylate (3aRS,4SR,9SR,9aRS)-9-(4-chloro-3-fluorophenyl)-4,9-ethano-2-[2-(2-methoxyphenyl)propenoyl]-2,3,3a,4,9,9a-hexahydro-1H-benzo[f]isoindole-3a-carboxylic acid methyl (3aRS,4SR,9SR,9aRS)-4,9-ethano-2-[2-(2-methoxyphenyl)propenoyl]-9-(3-methylphenyl)-2,3,3a,4,9,9a-hexahydro-1H-benzo[f]isoindole-3a-carboxylate (3aRS,4SR,9SR,9aRS)-4,9-ethano-2-[2-(2-methoxyphenyl)propenoyl]-9-(3-methylphenyl)-2,3,3a,4,9,9a-hexahydro-1H-benzo[f]isoindole-3a-carboxylic acid methyl (3aRS,4SR,9SR,9aRS)-9-(1,3-benzodioxol-5-yl)-4,9-ethano-2-[2-(2-methoxyphenyl)propenoyl]-2,3,3a,4,9,9a-hexahydro-1H-benzo[f]isoindole-3a-carboxylate methyl (3aRS,4SR,9SR,9aRS)-9-(3,4-dimethylphenyl)-4,9-ethano-2[2-(2-methoxyphenyl)propenoyl]-2,3,3a,4,9,9a-hexahydro-1H-benzo[f]isoindole-3a-carboxylate (3aRS,4SR,9SR,9aRS)-9-(3,4-dimethylphenyl)-4,9-ethano-2[2-(2-methoxyphenyl)propenoyl]-2,3,3a,4,9,9a-hexahydro-1H-benzo[f]isoindole-3a-carboxylic acid methyl (3aRS,4SR,9SR,9aRS)-4,9-ethano-9-(4-methoxyphenyl)-2-[2-(2-methoxyphenyl)propenoyl]-2,3,3a,4,9,9a-hexahydro-1H-benzo[f]isoindole-3a-carboxylate (3aRS,4SR,9SR,9aRS)-4,9-ethano-9-(4-methoxyphenyl)-2-[2-(2-methoxyphenyl)propenoyl]-2,3,3a,4,9,9a-hexahydro-1H-benzo[f]isoindole-3a-carboxylic acid (3aRS,4SR,9SR,9aRS)-4,9-ethano-9-(4-methoxyphenyl)-2 -[2-(2-methoxyphenyl)propenoyl]-2,3,3a,4,9,9a-hexahydro-1H-benzo[f]isoindole-3a-N-(3-pyridylmethyl)carboxamide (3aRS,4SR,9SR,9aRS)-4,9-ethano-9-(4-methoxyphenyl)-2-[2-(2-methoxyphenyl)propenoyl]-2,3,3a,4,9,9a-hexahydro-1H-benzo[f]isoindole-3a-N'-phenylcarbohydrazide (3aRS,4SR,9SR,9aRS)-4,9-ethano-9-(4-methoxyphenyl)-2-[2-(2-methoxyphenyl)propenoyl]-2,3,3a,4,9,9a-hexahydro-1H-benzo[f]isoindole-3a-hydroxamic acid (3aRS,4SR,9SR,9aRS)-4,9-ethano-9-(4-methoxyphenyl)-2-[2-(2-methoxyphenyl)propenoyl]-2,3,3a,4,9,9a-hexahydro-1H-benzo[f]isoindole-3a-N'-(3-pyridyl)carbohydrazide (3aRS,4SR,9SR,9aRS)-4,9-ethano-9-(4-methoxyphenyl)-2-[2-(2-methoxyphenyl)propenoyl]-2,3,3a,4,9,9a-hexahydro-1H-benzo[f]isoindole-3a-N-(3-thienylmethyl)carboxamide (RS)- and (SR)-2-{(3aRS,4SR,9SR,9aRS)-4,9-ethano-9-(4-methoxyphenyl)-2-[2-(2-methoxyphenyl)propenoyl]-2,3,3a,4,9,9a-hexahydro-1H-benzo[f]isoindole-3a-carbonylamino}phenylacetic acids (3aRS,4SR,9SR,9aRS)-4,9-ethano-2-[2-(2-methoxyphenyl)propenoyl]-9-(4-trifluoromethoxyphenyl)-2,3,3a,4,9,9,9a-hexahydro-1H-benzo[f]isoindole-3a-carboxylic acid methyl (3aRS,4SR,9SR,9aRS)-9-(3-bromophenyl)-4,9-ethano-2-[2-(2-methoxyphenyl)propenoyl]-2,3,3a,4,9,9a-hexahydro-1H-benzo[f]isoindole-3a-carboxylate (3aRS,4SR,9SR,9aRS)-9-(3-bromophenyl)-4,9-ethano-2-[2-(2-methoxyphenyl)propenoyl]-2,3,3a,4,9,9a-hexahydro-1H-benzo[f]isoindole-3a-carboxylic acid methyl (3aRS,4SR,9SR,9aRS)-4,9-ethano-9-(3-fluorophenyl-2-[2-(2-methoxyphenyl)propenoyl]-2,3,3a,4,9,9a-hexahydro-1H-benzo[f]isoindole-3a-carboxylate (3aRS,4SR,9SR,9aRS)-4,9-ethano-9-(3-fluorophenyl)-2-[2-(2-methoxyphenyl)propenoyl])-2,3,3a,4,9,9a-hexahydro-1H-benzo[f]-isoindole-3a-carboxylic acid (3aRS,4SR,9SR,9aRS)-4,9-ethano-9-(3-fluorophenyl)-2-[2-(2-methoxyphenyl)propenoyl)]-2,3,3a,4,9,9a-hexahydro-1H-benzo[f]isoindole-3a-[N-(3-pyridylmethyl)carboxamide methyl (3aRS,4SR,9SR,9aRS)-9-(3-chlorophenyl)-4,9-ethano-2-[2-(2-methoxyphenyl)propenoyl]-2,3,3a,4,9,9a-hexahydro-1H-benzo[f]isoindole-3a-carboxylate (3aRS,4SR,9SR,9aRS)-9-(3-chlorophenyl)-4,9-ethano-2-(2-(2-methoxyphenyl)propenoyl]-2,3,3a,4,9,9a-hexahydro-1H-benzo[f]isoindole-3a-carboxylic acid (3aRS,4SR,9SR,9aRS)-9-(3-chlorophenyl)-4,9-ethano-2-[2-(2-methoxyphenyl)propenoyl)]-2,3,3a,4,9,9a-hexahydro-1H-benzo[f]isoindole 3a-[N-(3-pyridylmethyl)carboxamide methyl (3aRS,4SR,9SR,9aRS)-9-(3-N,N-dimethyl-aminophenyl)-4,9-ethano-2-[2-(2-methoxyphenyl)-propenoyl]-2,3,3a,4,9,9,9a-hexahydro-1H-benzo[f]-isoindole-3a-carboxylate (3aRS,4SR,9SR,9aRS)-9-(3-N,N-dimethylaminophenyl)-4,9-ethano-2-[2-(2-methoxyphenyl)propenoyl]-2,3,3a,4,9,9,9a-hexahydro-1H-benzo[f]isoindole-3a-carboxylic acid methyl (3aRS,4SR,9SR,9aRS)-9-(3-aminophenyl)-4,9-ethano-2-[2-(2-methoxyphenyl)propenoyl]-2,3,3a,4,9,9,9a-hexahydro-1H-benzo[f]isoindole-3a-carboxylate hydrochloride methyl (3aRS,4SR,9SR,9aRS)-9-(4-N,N-dimethylaminophenyl)-4,9-ethano-2-[2-(2-methoxyphenyl)propenoyl]-2,3,3a,4,9,9,9a-hexahydro-1H-benzo[f]isoindole-3a-carboxylate (3aRS,4SR,9SR,9aRS)-9-(4-cyanophenyl)-4,9-ethano-2-[2-(2-methoxyphenyl)propenoyl]-2,3,3a,4,9,9,9a-hexahydro-1H-benzo[f]isoindole-3a-carboxylic acid methyl (3aRS,4SR,9SR,9aRS)-9-(3-cyanophenyl)-4,9-ethano-2-[2-(2-methoxyphenyl)propenoyl]-2,3,3a,4,9,9,9a-hexahydro-1H-benzo[f]isoindole-3a-carboxylate (3aRS,4SR,9SR,9aRS)-4,9-ethano-9-(3-hydroxy-4-methoxyphenyl)-2-[2-(2-methoxyphenyl)propenoyl]-2,3,3a,4,9,9a-hexahydro-1H-benzo[f]isoindole-3a-carboxylic acid methyl (3aRS,4SR,9SR,9aRS)-4,9-ethano-5-methoxy-2-[2-(2-methoxyphenyl)propenoyl]-9-(4-methylphenyl)-2,3,3a,4,9,9a-hexahydro-1H-benzo[f]isoindole-3a-carboxylate (3aRS,4SR,9SR,9aRS)-4,9-ethano-5-methoxy-2-[2-(2-methoxyphenyl)propenoyl]-9-(4-methylphenyl)-2,3,3a,4,9,9a-hexahydro-1H-benzo[f]isoindole-3a-carboxylic acid (3aRS,4SR,9SR,9aRS)-4,9-ethano-2[2-(2-methoxyphenyl)-2-propenoyl]-4-methyl-9-(4-methoxyphenyl)-2,3,3a,4,9,9a-hexahydro-1H-benzo[f]isoindole-3a-carboxylic acid (3aRS,4SR,9SR,9aRS)-9-(benzothien-2-yl)-4,9-ethano-2-[2-(2-methoxyphenyl)propenoyl)]-2,3,3a,4,9,9a-hexahydro-1H-benzo[f]isoindole-3a-carboxylic acid (3aRS,4SR,9SR,9aRS)-9-(2,4-dichlorophenyl)-4,9-ethano-2-[2-(2-methoxyphenyl)propenoyl)]-2,3,3a,4,9,9a-hexahydro-1H-benzo[f]isoindole-3a-carboxylic acid (3aRS,4SR,8SR,8aRS)-4,8-ethano-2-[2-(2-methoxyphenyl)propenoyl]-8-phenyl-2,3,3a,4,8,8a-hexahydro-1H-thieno[2,3-f]isoindole-3a-carboxylic acid (3aRS,4SR,8SR,8aRS)-4,8-ethano-2-[2-(2-methoxyphenyl)propenoyl]-8-(4-methylphenyl)-2,3,3a,4,8,8a-hexahydro-1H-thieno[2,3-f]isoindole-3a-carboxylic acid (3aRS,4SR,8SR,8aRS)-4,8-ethano-2-[2-(2-methoxyphenyl)propenoyl]-8-(4-trifluoromethylphenyl)-2,3,3a,4,8,8a-hexahydro-1H-thieno[2,3-f]isoindole-3a-carboxylic acid (3aRS,4SR,8SR,8aRS)-N-benzyl-4,8-ethano-2-[2-(2-methoxyphenyl)propenoyl]-8-(4-trifluoromethylphenyl)-2,3,3a,4,8,8a-hexahydro-1H-thieno[2,3-f]isoindole-3a-carboxamide (3aRS,4SR,10SR,10aRS)-4,9-ethano-2-[2-(2-methoxyphenyl)propenoyl]-10-(4-methylphenyl)-2,3,3a,4,10,10a-hexahydro-1H-indolo[2,3-f]isoindole-3a-carboxylic acid (3aRS,4SR,8SR,8aRS)-N-(3-pyridyl)methyl-4,8-ethano-2-[2-(2-methoxyphenyl)propenoyl]-8-(4-methylphenyl)-2,3,3a,4,8,8a-hexahydro-1H-thieno[2,3-f]isoindole-3a-carboxamide methyl (3aRS,4SR,8SR,BaRS)-4,8-ethano-8-(4-methoxyphenyl)-2-[2-(2-methoxyphenyl)propenoyl]-2,3,3a,4,8,8a-hexahydro-1H-thieno[2,3-f]isoindole-3a-carboxylate (3aRS,4SR,8SR,8aRS)-4,8-ethano-8-(4-methoxyphenyl)-2-[2-(2-methoxyphenyl)propenoyl]-2,3,3a,4,8,8a-hexahydro-1H-thieno[2,3-f]isoindole-3a-carboxylic acid (3aRS,4SR,8SR,8aRS)-N-(3-pyridyl)methyl-8-(benzo-1,4-dioxan-6-yl)-4,8-ethano-2-[2-(2-methoxyphenyl)propenoyl]-2,3,3a,4,8,8a-hexahydro-1H-thieno[2,3-f]isoindole-3a-carboxamide, in the racemic form or their optical isomers, as well as their salts.

In that which precedes and that which follows, the expression "optical isomer" or optically active form defines the pure form of said optical isomer or optionally the "enriched" mixture of optical isomers, that is to say predominantly comprising said optical isomer or said form.

More preferably, mention may also be made, according to the invention, of any compound of general formula (I) individually selected from:

(3aRS,4SR,9SR,9aRS)-4,9-ethano-2-[2-(2-methoxyphenyl)propenoyl]-9-(4-methylphenyl)-2,3,3a,4,9,9a-hexahydro-1H-benzo[f]isoindole-3a-carboxylic acid (3aRS,4SR,9SR,9aRS-9-(benzothien-2-yl)-4,9-ethano-2-[2-(2-methoxyphenyl)propenoyl)]-2,3,3a,4,9,9a-hexahydro-1H-benzo[f]isoindole-3a-carboxylic acid (3aRS,4SR,9SR,9aRS)-9-(2,4-dichlorophenyl)-4,9-ethano-2-[2-(2-methoxyphenyl) propenoyl)]-2,3,3a,4,9,9a-hexahydro-1H-benzo[f]isoindole-3a-carboxylic acid (3aRS,4SR,9SR,9aRS)-9-(3,4-dichlorophenyl)-4,9-ethano-2-[2-(2-methoxyphenyl)propenoyl]-2,3,3a,4,9,9a-hexahydro-1H-benzo[f]isoindole-3a-carboxylic acid (3aRS, 4SR,9SR,9aRS)-9-(4-bromophenyl)-4,9-ethano-2-[2-(2-methoxyphenyl)propenoyl]-2,3,3a,4,9,9a-hexahydro-1H-benzo[f]isoindole-3a-carboxylic acid (3aRS,4SR,9SR,9aRS)-4,9-ethano-2-[2-(2-methoxyphenyl)propenoyl]-9-(4-chlorophenyl)-2,3,3a,4,9,9a-hexahydro-1H-benzo[f]isoindole-3a-carboxylic acid methyl (3aRS,4SR,9SR,9aRS)-9-(2,3-dihydrobenzofuran-5-yl)-4,9-ethano-2-[2-(2-methoxyphenyl)propenoyl]-2,3,3a,4,9,9a-hexahydro-1H-benzo[f]isoindole-3a-carboxylate acid (3aRS,4SR,8SR,8aRS)-4,8-ethano-2-[2-(2-methoxyphenyl)propenoyl]-8-(4-methylphenyl)-2,3,3a,4,8,8a-hexahydro-1H-thieno[2,3-f]isoindole-3a-carboxylic acid in the form of their optical isomers, as well as their salts.

Mention may be made, as very particularly advantageous optical isomer of the compounds of general formula (I) according to the invention, of any compound individually chosen from:

(3aRS,4SR,9SR,9aRS)-4,9-ethano-2-[2-(2-methoxyphenyl)propenoyl]-9-(4-methylphenyl)-2,3,3a,4,9,9a-hexahydro-1H-benzo[f]isoindole-3a-carboxylic acid (3aRS,4SR,9SR,9aRS-9-(benzothien-2-yl)-4,9-ethano-2-[2-(2-methoxyphenyl)propenoyl)]-2,3,3a,4,9,9a-hexahydro-1H-benzo[f]isoindole-3a-carboxylic acid (3aRS,4SR,9SR,9aRS)-9-(2,4-dichlorophenyl)-4,9-ethano-2-[2-(2-methoxyphenyl)propenoyl)]-2,3,3a,4,9,9a-hexahydro-1H-benzo[f]isoindole-3a-carboxylic acid (3aRS,4SR,9SR,9aRS)-9-(3,4-dichlorophenyl)-4,9-ethano-2-[2-(2-methoxyphenyl)propenoyl]-2,3,3a,4,9,9a-hexahydro-1H-benzo[f]isoindole-3a-carboxylic acid (3aRS,4SR,9SR,9aRS)-9-(4-bromophenyl)-4,9-ethano-2-[2-(2-methoxyphenyl)propenoyl]-2,3,3a,4,9,9a-hexahydro-1H-benzo[f]isoindole-3a-carboxylic acid (3aRS,4SR,9SR,9aRS)-4,9-ethano-2-[2-(2-methoxyphenyl)propenoyl]-9-(4-chlorophenyl)-2,3,3a,4,9,9a-hexahydro-1H-benzo[f]isoindole-3a-carboxylic acid methyl (3aRS,4SR,9SR,9aRS)-9-(2,3-dihydrobenzofuran-5-yl)-4,9-ethano-2-[2-(2-methoxyphenyl)propenoyl]-2,3,3a,4,9,9a-hexahydro-1H-benzo[f]isoindole-3a-carboxylate acid (3aRS,4SR,8SR,8aRS)-4,8-ethano-2-[2-(2-methoxyphenyl)propenoyl]-8-(4-methylphenyl)-2,3,3a,4,8,8a-hexahydro-1H-thieno[2,3-f]isoindole-3a-carboxylic acid, or their salts.

According to Applications WO 98/29390 and FR 2,772,764, the process for the preparation of the products of general formula (I) employs the intermediate of general formula (X):

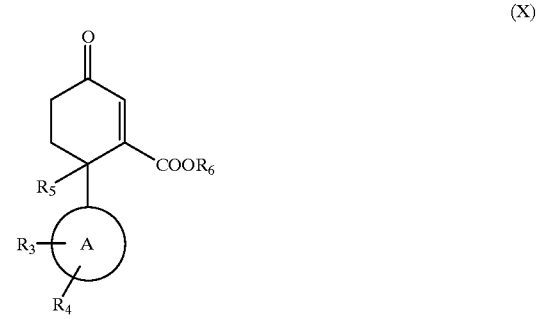

in which formula A, $R_3$, $R_4$, $R_5$ and $R_6$ are as defined in general formula (I), in the racemic form, resulting in subsequent products also in the racemic form.

According to the present invention, the stereochemistry of the products of general formula (X) in the racemic form can be resolved, forming the optical isomers (X') of the products of general formula (X).

This stage makes it possible to carry out the subsequent stages of the preparation process starting with the optical isomers of formula (X') of the products of general formula (X).

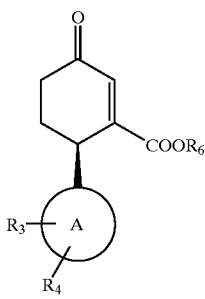

(X')

in which formula A, $R_3$, $R_4$ and $R_6$ are defined as above.

It is understood that the other subsequent stages of the process which are described above and below remain unchanged and can be carried out in the same way on the racemic mixture (X) or the optical isomers of the compounds of general formula (X'). The preparation process employing the enantiomeric resolution of the compound (X') is simpler and more efficient than that employing the racemic mixture of the compound (X): this is because this route makes it possible to avoid the final stage of separation of the enantiomers of the racemic mixture and also makes it possible to increase the overall yield while economizing on the amount of reactants employed in the stages subsequent to the enzymatic stage. This process also forms part of the present invention.

The optical isomers of general formula (X') can be obtained from the compounds of general formula (X) in the following way:

The optical isomers of general formula (X') of the compounds of general formula (X) can be separated from the compounds of general formula (X) in the form of a racemic mixture, advantageously by enzymatic resolution.

Very advantageously, it has been discovered according to the invention that the enantiomeric resolution can be obtained by carrying out an enantiospecific enzymatic reaction.

Use may preferably be made, as enzyme, of an enzyme which makes it possible to separate the enantiomers of general formula (X') with the desired stereochemistry, such as levorotatory enantiomers, from the other enantiomers, such as dextrorotatory enantiomers, or their derivatives.

According to the invention, the enzyme employed is chosen from lipases, esterases or proteases.

Use is preferably made of a lipase or an esterase in preparing the product of general formula (X') in the levorotatory form.

Use is preferably made of a protease or a lipase in preparing the product of general formula (X') in the dextrorotatory form.

Lipases, esterases and proteases and their uses are described in particular in Enzyme Catalysis in Organic Synthesis, K. Drauz et al., VCH.

Preference is given, among the lipases and esterases which make it possible to obtain the product of general formula X' in the levorotatory form, to: Chirazyme® L2 (sold by Boehringer Mannheim), Lipase PS C (sold by Amano Enzymes), ESL 01 (sold by Recombinant Biocatalyst), SP 525 (sold by Novo Nordisk), Chirazyme® L6 (sold by Boehringer Mannheim) and Esterase 30000 (sold by Gist Brocades).

Preference is given, among the proteases and lipases which make it possible to obtain the product of general formula X' in the dextrorotatory form, to: Pronase® (Boehringer Mannheim), Subtilisin (Novo Nordisk), Alacalase 2.4 L (Novo Nordisk), Protease Nagarse (Sigma), EH 16 (Altus Biologics), EH 15 (Altus Biologics), EH 11 (Altus Biol.) and Lipase M (Amano Enzymes).

The enzymes used may be commercially available or may be derived from suitable microorganisms, which can be chosen, for example, from the Catalogue of the American Type Culture Collection (ATCC), which microorganisms are optionally genetically modified, according to conventional methods known to the person skilled in the art, including in particular the use of isolated enzymes or of cellular extracts. Use is preferably made of a protease in preparing the product of general formula (X') in the dextrorotatory form.

Lipases, esterases and proteases and their uses are described in particular in Enzyme Catalysis in Organic Synthesis, K. Drauz et al., VCH.

The reaction is generally carried out starting with a mixture of a solution comprising the product of general formula (X) in the racemic form in a hydrocarbon-comprising organic solvent, such as cyclohexane, and of an aqueous potassium hydrogenphosphate solution, which solution is preferably adjusted to a pH of between 6 and 8, for example using phosphoric acid, to which mixture is added an aqueous solution of the appropriate enzyme. The concentration of the product of general formula (X) in the reaction mixture is generally between 5 and 50 g/l.

The volume of the organic solution preferably represents 10 to 30% of the total volume of the aqueous solution.

The amount of enzyme employed in the reaction mixture is preferably between 0.4 and 4 MU/l (1 MU : unit of enzymatic activity).

The reaction is generally carried out at a temperature of between 20 and 40° C., with stirring, and its progress can be monitored by chiral HPLC. The organic phase can optionally subsequently be separated from the aqueous phase and then clarified by addition of an appropriate solvent or a mixture of appropriate solvents, such as, for example, aliphatic alcohols, such as ethanol.

Very advantageously, it has been discovered according to the invention that the lipase from Candida Antartica, "fraction B", such as, for example, the enzyme Chirazyme L2 sold by Boehringer Mannheim, can carry out the reaction resulting in the compound of general formula (XI) with an enantiomeric excess of greater than 90%.

Very advantageously, it has been discovered according to the present invention that the compounds of general formula (X') in the levorotatory form make it possible to result directly in the compounds of general formula (I), in the dextrorotatory form, which are disclosed as particularly advantageous in Applications WO 98/29390 and FR 2,772,764.

The present invention also relates to the use of the compound of general formula (X') in the preparation of the compounds of general formula (I) in the form of optical isomers:

The subsequent stages of the process are then carried out on the optical isomer of general formula (X') in the same way as in the process disclosed in Applications WO 98/29390 and FR 2,772,764, which employs the racemic mixture of general formula (X).

Namely:

The product of general formula (X') is converted to the product of general formula (IX) in the form of optical isomers, preferably the levorotatory isomer:

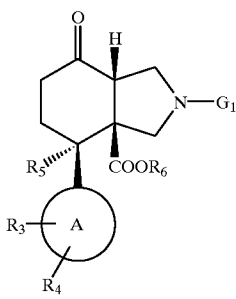

(IX)

in which formula A, $R_3$, R4, $R_5$, $R_6$ are as defined in general formula I and $G_1$ represents a protective group for the amine functional group, such as benzyl, by reaction with an N-trialkylsilylmethyl-N-(alkoxymethyl)amine carrying a protective group for the amine functional group, such as a benzyl radical, for example N-trimethylsilylmethyl-N-(n-butoxymethyl)benzylamine, which can be prepared under the conditions described in Chem. Pharm. Bull., 276 (1985).

The reaction is generally carried out in an organic solvent, such as a halogenated aliphatic hydrocarbon, for example dichloromethane, in the presence of a strong acid, such as trifluoroacetic acid, at a temperature of between 0° C. and reflux of the reaction mixture.

The products of general formula (IX) in the form of optical isomers are subsequently employed, according to the process disclosed in Applications WO 98/29390 and FR 2,772,764, according to the possible routes resulting in the products of general formula (I) in the form of optical isomers.

1. According to a first route, the products of general formula (I) in the form of optical isomers can be obtained from the products of general formula (IX), by cyclization of the cycloperhydroisoindole nucleus, by passing through the compounds of general formula (III)

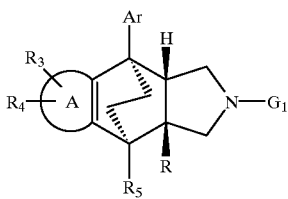

(III)

in the form of optical isomers, preferably the dextrorotatory isomer, in which formula:

A, Ar, R, $R_3$, $R_4$ and $R_5$ are defined according to the general formula I and $G_1$ represents a hydrogen atom, and then, without distinction, by coupling with the side chain and optionally modification of the R substituent.

The products of general formula (I) in which:

Y represents an oxygen or sulfur atom and

X represents one of the following groups: —CO—, methylene, alken-1,1-diyl, such as vinyldiyl, or cycloalkan-1,1-diyl comprising 3 to 6 carbon atoms, can be obtained by reaction of an acid of general formula (II):

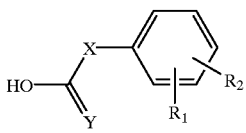

(II)

in which formula:

$R_1$ and $R_2$ are defined according to the general formula I and X defined as above and Y represents an oxygen or sulfur atom, of its methyl ester or of a derivative of this acid, such as a halide or the anhydride, with a product of general formula (III):

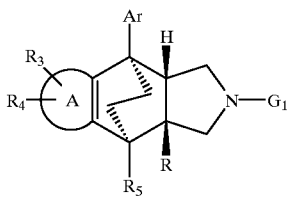

(III)

in which formula:

A, Ar, R, $R_3$, $R_4$ and $R_5$ are defined according to the general formula I and $G_1$ represents a hydrogen atom (which can be obtained from a product of general formula (III) in which $G_1$ represents a protective group for an amino functional group, such as a benzyl, benzyloxycarbonyl, tert-butoxycarbonyl or vinyloxycarbonyl radical, by hydrogenolysis in the presence of a catalyst, such as palladium-on-charcoal, when $G_1$ represents a benzyl or benzyloxycarbonyl radical, or by hydrolysis in acidic medium, when $G_1$ represents a tert-butoxycarbonyl, vinyloxycarbonyl or benzyloxycarbonyl radical).

In that which follows, the definition in which Gi represents a benzyl radical is given only by way of illustration and it is obvious to a person skilled in the art to adjust the various procedures to the other protective groups for an amino functional group, such as a benzyl, benzyloxycarbonyl, tert-butoxycarbonyl or vinyloxycarbonyl radical.

Generally, the reaction of the product of general formula (II), in the acid form, with the product of general formula (III) is carried out in an organic solvent, such as a halogenated aliphatic hydrocarbon, such as dichloromethane, in the presence of a coupling agent, such as i-ethyl-3-[3-(dimethylamino)propyl]carbodiimide hydrochloride, 1,3-dicyclohexylcarbodiimide or benzotriazol-1-yloxytris-(dimethylamino)phosphonium hexafluorophosphate, and optionally of an activating agent, such as hydroxybenzotriazole, at a temperature of between 0° C. and the reflux temperature of the reaction mixture.

The reaction of the product of general formula (II), in the form of the methyl ester, with a product of general formula (III) is generally carried out in an organic solvent, such as dioxane or a halogenated aliphatic hydrocarbon, such as dichloromethane, at a temperature of between 0° C. and the reflux temperature of the reaction mixture.

The reaction of the product of general formula (II), in the halide form, with the product of general formula (III) is generally carried out in an organic solvent, such as a halogenated aliphatic hydrocarbon, such as dichloromethane, in the presence of a base (tertiary aliphatic amine) at a temperature of between 0° C. and the reflux temperature of the reaction mixture.

The reaction of the product of general formula (II), in the anhydride form, with the product of general formula (III) is generally carried out in an organic solvent, such as a halogenated aliphatic hydrocarbon, such as dichloromethane, in the presence of a base (tertiary aliphatic amine, pyridine or 4-dimethylaminopyridine) at a temperature of between 0 and 50° C.

In addition, on conclusion of the reaction of II with III, it is optionally possible, when R represents or comprises a —COOR$_6$ or —PO(OR9)2 radical with R$_6$ and R$_9$ representing an alkyl radical, to saponify the product obtained, in order to obtain a product of general formula (I) in which R represents or comprises a carboxyl radical or to convert, by means of a nucleophilic agent, the product obtained, in order to obtain a product of general formula (I) in which R represents or comprises a —PO$_3$H$_2$ radical.

The saponification of a product of general formula (I) in which R represents or comprises an ester of general formula —COOR$_6$ into a product of general formula (I) in which R represents or comprises a carboxyl radical is generally carried out by means of an inorganic base, such as sodium hydroxide or potassium hydroxide or sodium carbonate, in an organic solvent, such as an alcohol, for example methanol or ethanol, or such as an ether, for example dioxane, at a temperature of between 20° C. and the reflux temperature of the solvent.

The conversion of a product of general formula (I) in which R represents or comprises a PO(OR$_9$)$_2$ radical into a product of general formula (I) in which R represents or comprises a PO$_3$H$_2$ radical is generally carried out by reaction with a nucleophilic agent, such as a trialkylsilyl (trimethylsilyl) halide (iodide), or with a sodium or lithium halide (sodium iodide) in the presence of a trialkylhalosilane (trimethylchlorosilane, trimethylbromosilane), the reaction being carried out in a solvent, such as carbon tetrachloride or acetonitrile, at a temperature of between 0 and 50° C., or by heating with an alkali metal halide (sodium iodide), followed by hydrolysis.

The present invention also relates to the products of general formula (III):

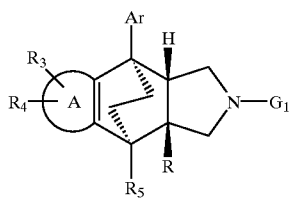

(III)

in the form of optical isomers, preferably the dextrorotatory isomer: in which formula:

Ar, R, R$_3$, R$_4$ and R$_5$ are defined according to the general formula I and G$_1$ represents a hydrogen atom or a protective group for an amino functional group, such as benzyl.

The products of general formula (I) in which:
Y represents an oxygen or sulfur atom and
X represents an oxygen atom can be obtained by the reaction of a haloformate or of a halothioformate of general formula (IV):

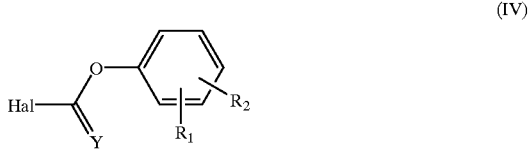

(IV)

in which formula:
Y represents an oxygen or sulfur atom,
R$_1$ and R$_2$ are defined as above and
Hal represents a halogen atom, with a product of general formula (III).

The reaction of the halide of general formula (IV) with the product of general formula (III) is generally carried out in organic or aqueous/organic medium, such as a dioxane/water mixture, in the presence of an inorganic base (sodium hydroxide) or organic base (triethylamine) at a temperature of between 0 and 50° C.

In the same way as above, when R represents or comprises a —COOR$_6$ or —PO(OR$_9$)$_2$ radical, it is possible to saponify the product obtained, in order to obtain a product of general formula (I) in which R represents or comprises a carboxyl radical, or to convert, by means of a nucleophilic agent, the product obtained into a product of general formula (I) in which R represents or comprises a —PO$_3$H$_2$ radical.

The products of general formula (I) in which:
Y represents an oxygen or sulfur atom and
X represents an NH group can be obtained by reaction of an isocyanate or of an isothiocyanate of general formula (V):

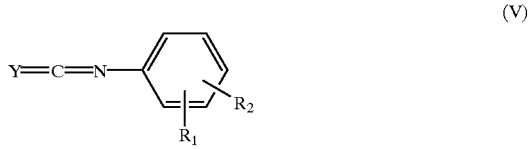

(V)

in which formula:
Y represents an oxygen or sulfur atom and
R$_1$ and R$_2$ are defined according to the general formula I with a product of general formula (III) as defined above.

The reaction of the product of general formula (V) with the product of general formula (III) is generally carried out in an inert organic solvent, such as tetrahydrofuran or toluene, in the presence of an activating agent, such as 4-dimethylaminopyridine or 4-pyrrolidinopyridine, at a temperature of between 0 and 50° C.

The reaction of V with II is optionally followed, when R represents or comprises a —COOR$_6$ or —PO(OR9)2 radical in which R$_6$ or R$_9$ represent an alkyl radical, by the saponification of the product obtained, in order to obtain a product of general formula (I) in which R represents or comprises a carboxyl radical, or by the conversion, by means of a nucleophilic agent, of the product obtained, in order to obtain a product of general formula (I) in which R represents or comprises a —PO$_3$H$_2$ radical. The optional conversion of the —COOR$_6$ and PO(OR$_9$) $_2$ radicals respectively by carboxyl and PO$_3$H$_2$ radicals is carried out under the conditions described above.

The products of general formula (I) in which:
R represents a radical of general formula

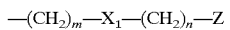

—(CH$_2$)$_m$—X$_1$—(CH$_2$)$_n$—Z with X$_1$, m and n defined as above and
Z representing a —COOR$_6$ radical with R$_6$ representing a straight or branched alkyl radical comprising 1 to 3 carbon atoms, can be obtained by esterification of a product of general formula (I) in which Z represents a carboxyl radical.

The esterification is generally carried out by means of an alcohol of general formula $R_6$—OH in which $R_6$ is defined as above, the reaction being carried out in acidic medium, or by means of an alkyl halide of general formula $R_6$—Hal in which Hal represents a halogen (iodine) atom, the reaction being carried out in alkaline medium (alkali metal or alkaline-earth metal carbonate, such as cesium carbonate), the reaction being carried out in an organic solvent, such as dimethylformamide, at a temperature of between 0 and 50° C.

The products of general formula (I) in which:
R represents a radical of general formula $$—(CH_2)_m—X_1—(CH_2)_n—Z$$

in which:
$X_1$, m and n are defined as above and
Z represents a —CON($R_7$) ($R_8$) radical in which:
$R_7$ represents a hydrogen atom or a straight or branched alkyl radical comprising 1 to 6 carbon atoms and
$R_8$ represents a hydrogen atom or a straight or branched alkyl radical comprising 1 to 6 carbon atoms optionally substituted by an amino, alkylamino comprising 1 to 4 carbon atoms, dialkylamino, each alkyl part of which comprises 1 to 4 carbon atoms, alkoxy comprising 1 to 4 carbon atoms, alkylthio comprising 1 to 4 carbon atoms, alkyloxycarbonyl, the alkyl part of which comprises 1 to 4 carbon atoms, carboxyl, cyano, phenyl optionally substituted by one or more identical or different radicals chosen from alkoxy radicals comprising 1 to 4 carbon atoms or trifluoromethyl radicals, 1- or 2-naphthyl, 2- or 3-furyl, 2- or 3-thienyl, 4- or 5-imidazolyl or 4- or 5-thiazolyl, or 2-, 3- or 4-pyridyl radical, or an indanyl or chromanyl radical or alternatively
$R_7$ represents a hydrogen atom or a straight or branched alkyl radical comprising 1 to 6 carbon atoms and
$R_8$ represents a hydroxyl, amino, alkyloxy comprising 1 to 6 straight- or branched-chain carbon atoms optionally substituted by a phenyl radical, alkylamino or dialkylamino, the alkyl parts of which comprise 1 to 4 carbon atoms, radical, or else preferably in which
$R_7$ represents a hydrogen atom or a straight or branched alkyl radical comprising 1 to 6 carbon atoms and
$R_8$ represents
a hydrogen atom,
a hydroxyl radical,
an arylsulfonyl radical, such as phenylsulfonyl, optionally substituted by one or more atoms or radicals, which are identical or different, chosen from halogen atoms and alkyl or alkyloxy radicals with, for these radicals, alkyl comprising 1 to 4 carbon atoms,
a 5- to 7-membered heterocycle incorporating one or more heteroatoms chosen from nitrogen, oxygen or sulfur atoms, it being possible for said heterocycle to be bonded via a heteroatom,
an amino radical optionally substituted by one or two radicals, which are identical or different, chosen from the following radicals:
alkyl comprising 1 to 4 carbon atoms,
aryl, such as phenyl, optionally substituted by one or more radicals, which are identical or different, chosen from alkyl or alkyloxy radicals with, for these radicals, alkyl comprising 1 to 4 carbon atoms,
5- to 7-membered heterocyclyl comprising one or more heteroatoms chosen from nitrogen, oxygen and sulfur atoms,
arylcarbonyl, such as benzoyl, optionally substituted by one or more radicals, which are identical or different, chosen from alkyl or alkyloxy radicals with, for these radicals, alkyl comprising 1 to 4 carbon atoms,
an alkyloxy radical comprising 1 to 6 straight- or branched-chain carbon atoms optionally substituted by a phenyl radical,
a straight or branched alkyl radical comprising 1 to 6 carbon atoms, such as methyl, optionally substituted by an amino, alkylamino, dialkylamino, hydroxyl, alkoxy comprising 1 to 4 carbon atoms, mercapto, alkylthio, alkyloxycarbonyl, carboxyl or cyano radical, an optionally substituted mono- or polycyclic aromatic radical having from 5 to 12 ring members which may or may not incorporate one or more heteroatoms chosen from oxygen, nitrogen and sulfur atoms, it being possible for said aromatic radical to be in particular the 2- or 3- or 4-pyridyl radical, preferably 3-pyridyl or 4-pyridyl, or the N-oxide of pyridine, or it also being possible for said aromatic radical to be a phenyl radical optionally substituted by one or more halogen atoms or by one or more hydroxyl, amino or trifluoromethyl groups or by one or more alkyl or alkenyl, alkoxy, alkylthio, alkylamino, alkylcarbonyl or C2 to C4 alkoxycarbonyl, carbamoyl, alkylcarbamoyl or dialkylcarbamoyl, the alkyl part of which comprises 1 to 8 carbon atoms, or formyl radicals, or alternatively a 1- or 2-naphthyl radical,
preferably, $R_7$ represents a hydrogen atom and $R_8$ represents a methyl radical substituted by the 3-pyridyl radical,
can be obtained by reaction of a product of general formula:

$$HN(R_7)(R_8)$$

in which $R_7$ and R. are defined as above with a product of general formula (I) in which Z represents a carboxyl radical.
It is particularly advantageous:
either first to react oxalyl chloride with a compound of general formula (I), in which R s represents a carboxyl radical, in solution in dichloromethane, in order to form the acid chloride as an intermediate, and then to react the compound of general formula HN($R_7$) ($R_8$), optionally in the presence of a base, such as triethylamine,
or directly to react the compound of general formula HN($R_7$) ($R_8$) with a compound of general formula (I) in which R represents a carboxyl radical, in an organic solvent, such as an alcohol (ethanol) or a halogenated solvent, such as dichloromethane, in the presence of a coupling agent, such as N,N'-carbonyldiimidazole, 1,1-dicyclohexylcarbodiimide, 1-ethyl-3-[3-(dimethylamino)propyl]carbodiimide hydrochloride or benzotriazol-1-yloxytris(dimethylamino)phosphonium hexafluorophosphate, at a temperature of between 0 and 50° C.

When at least one of the $R_7$ and $R_8$ symbols is substituted by an amino radical, it is particularly advantageous to protect it by a protective group, such as a tert-butoxycarbonyl, benzyloxycarbonyl or benzyl radical, prior to the coupling of the amine of general formula HN($R_7$)($R_8$) to the appropriate acid and then to replace the protective group by a hydrogen atom, for example by hydrogenolysis by means of hydrogen in the presence of a catalyst, such as palladium-on-charcoal, when it represents a benzyl or benzyloxycarbonyl radical, or by hydrolysis in acidic medium, when it represents a tert-butoxycarbonyl or benzyloxycarbonyl radical.

When at least one of the $R_7$ and $R_8$ symbols is substituted by a carboxyl radical, it is particularly advantageous to protect it by a protective group, such as an alkyl radical optionally substituted by a phenyl radical, such as the benzyl radical, prior to the coupling of the amine of general formula $HN(R_7)(R_8)$ to the appropriate acid and then to replace the protective group by a hydrogen atom, for example by hydrogenolysis by means of hydrogen in the presence of a catalyst, such as palladium-on-charcoal, or by saponification under the conditions described above.

When, in the product of general formula (I), $R_7$ represents a hydrogen atom or an alkyl radical comprising 1 to 6 carbon atoms and $R_8$ represents an alkyloxy radical substituted by a phenyl radical, the replacement of the alkyloxy radical, substituted by a phenyl radical, by a hydroxyl radical, carried out:

either by hydrogenolysis in the presence of a catalyst, such as palladium-on-charcoal, or by treatment with aluminum chloride in the presence of anisole in an organic solvent, such as nitromethane, at a temperature of between $-20°$ C. and room temperature, when the alkyl radical substituted by a phenyl radical is a benzyl radical, makes it possible to obtain a product of general formula (I) in which $R_7$ represents a hydrogen atom or an alkyl radical comprising 1 to 4 carbon atoms and $R_8$ represents a hydroxyl radical.

The products of general formula (I) in which:
R represents a radical of general formula:

—NHCO—T in which T represents a hydrogen atom or an alkyl radical (1 to 6 carbon atoms) optionally substituted by an amino, carboxyl, alkyloxycarbonyl, hydroxyl, alkyloxy, mercapto or alkylthio radical, can be obtained by reaction of an acid of general formula:

T—CO—OH in which T is defined as above with a product of general formula VI:

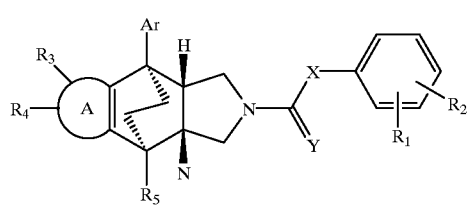
(VI)

in which formula:
A, Ar, $R_1$, $R_2$, $R_3$, $R_4$, $R_5$, X and Y are defined according to the general formula I.

The reaction of the acid of general formula T—CO—OH, in the acid form, with the product of general formula (VI) is generally carried out in an organic solvent, such as a halogenated aliphatic hydrocarbon, such as dichloromethane, in the presence of a coupling agent, such as 1-ethyl-3-[3-(dimethylamino)propyl]-carbodiimide hydrochloride, 1,1-dicyclohexylcarbodiimide or benzotriazol-1-oxytris(dimethylamino)-phosphonium hexafluorophosphate, optionally in the presence of an activating agent, such as hydroxybenzotriazole, at a temperature of between 0 and 50° C.

The reaction of the acid of general formula T—CO—OH, in the halide form, when T is other than a hydrogen atom, with the product of general formula (VI) is generally carried out in an organic solvent, such as a halogenated aliphatic hydrocarbon, such as dichloromethane, in the presence of a base (tertiary aliphatic amine) at a temperature of between 0 and 50° C.

The reaction of the acid of general formula T—CO—OH, in the anhydride form, with the product of general formula (VI) is generally carried out in an organic solvent, such as a halogenated aliphatic hydrocarbon, such as dichloromethane, in the presence of a base (tertiary aliphatic amine, pyridine or 4-dimethylaminopyridine) at a temperature of between 0 and 50° C.

The reaction of a compound T—CO—OH with a compound VI can optionally be followed by replacement of the protected ester functional groups or amine functional groups carried by T by carboxyl or amino radicals respectively, under the conditions described above.

When T is substituted by an amino radical, it is particularly advantageous to protect it by a protective group, such as a benzyloxycarbonyl or tert-butoxycarbonyl radical, prior to the coupling of the acid of general formula T—CO—OH to the appropriate amine and then to replace the protective group by a hydrogen atom, for example by hydrogenolysis by means of hydrogen in the presence of a catalyst, such as palladium-on-charcoal, or by hydrolysis in acidic medium.

When T is substituted by a carboxyl radical, it is particularly advantageous to protect it by a protective group, such as a methyl, ethyl or benzyl radical, prior to the coupling of the acid of general formula T—CO—OH to the appropriate amine and then to replace the protective group by a hydrogen atom, for example by hydrogenolysis by means of hydrogen in the presence of a catalyst, such as palladium-on-charcoal, or by saponification under the conditions described above.

The products of general formula (I) in which:
R represents a radical of general formula

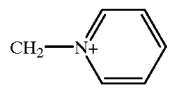

can be obtained by reaction of an excess of pyridine and of a strong acid or of a derivative of this acid with a product of general formula:

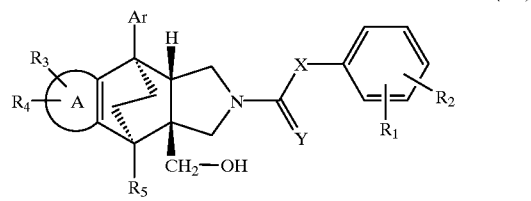
(VII)

in which formula A, Ar, $R_1$, $R_2$, $R_3$, $R_4$, $R_5$, X and Y are defined according to the general formula I.

The strong acid is preferably trifluoromethanesulfonic acid, optionally in the presence of trifluoromethanesulfonic anhydride.

The products of general formula (I) in which Y represents a sulfur atom can be obtained by thionation of a product of general formula (I) in which Y represents an oxygen atom.

The thionation is generally carried out under the usual conditions by means of phosphorus pentasulfide, the reaction being carried out in an organic solvent, such as tetrahydrofuran, at a temperature of between 0 and 50° C.

The products of general formula (I) in which one of the $R_1$ or $R_2$ symbols represents an alkylcarbonyloxy radical can be obtained by acylation of a product of general formula (I) in which one of the $R_1$ or $R_2$ symbols represents a hydroxyl radical by means of an aliphatic acid or of a derivative of this acid, such as a halide or the anhydride, under the usual esterification conditions.

As regards the intermediates described above, operating protocols and compounds useful in obtaining them are also provided hereinbelow.

The products of general formula (III) in the form of optical isomers, preferably the dextrorotatory isomer, can be obtained from the products of general formula (IX) in the form of optical isomers, preferably the levorotatory isomer, according to the following possible routes:

i. Conventionally, the products of general formula (III) in which R represents a carboxyl radical or a radical of general formula $COOR_6$ can be obtained by the action of trifluoromethanesulfonic acid on a product of general formula (VIII):

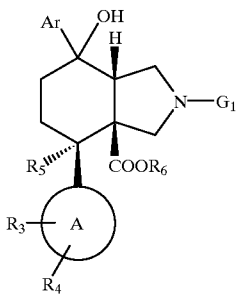

(VIII)

in the form of optical isomers, preferably the levorotatory isomer, in which formula:
A, Ar, $R_3$, $R_4$ and $R_5$, $R_6$ are defined as above,
$G_1$ represents a benzyl radical,
$R_6$ represents an alkyl radical comprising 1 to 3 carbon atoms
followed by replacement of the $G_1$ group by a hydrogen atom
  either by hydrogenolysis under the conditions described above, then, optionally, depending on the situation, followed by replacement of the hydrogen atom by a tert-butoxy carbonyl radical, by reaction with tert-butoxycarbonyl anhydride in an organic solvent, or by a benzyloxycarbonyl radical, by reaction with benzyloxycarbonyl chloride in an organic solvent
  or by reaction with an alkyl chloroformate, such as vinyl chloroformate or ethyl chloroformate or 2-chloroethyl chloroformate or 2,2,2-trichloroethyl chloroformate, in an organic solvent, such as dichloromethane, at a temperature of between 0° C. and room temperature, followed by acid hydrolysis of the intermediate carbamate formed, generally using a 1 to 6M aqueous hydrochloric acid solution, optionally in an organic solvent, such as an alcohol, for example methanol or ethanol, or an ether, for example tetrahydrofuran or dioxane.

The intramolecular cyclization of Friedel-Crafts type of the product of general formula (VIII) to the product of general formula (III) can generally be carried out by the action of an excess, from 3 to 20 molar equivalents, of a strong acid, such as trihluoromethanesulfonic acid, optionally in the presence of trifluoromethanesulfonic anhydride as a catalytic amount or optionally added as successive additions, the reaction being carried out in an organic solvent, such as dichloromethane, at a temperature of between 0° C. and the reflux temperature, from a few minutes to several days. It is also possible to carry out the intramolecular cyclization of Friedel-Crafts type by the action of a Lewis acid, such as aluminum chloride or titanium tetrachloride or boron trifluoride, optionally in the form of a complex with diethyl ether, in an organic solvent, such as dichloromethane or nitromethane or nitrobenzene.

This reaction can optionally be followed by saponification of the product obtained and optionally followed, depending on the situation, by replacement of the benzyl radical by a hydrogen atom.

The product of general formula (VIII) in the form of optical isomers, preferably the levorotatory isomer, can be obtained, for its part, conventionally by reaction of an organomagnesium derivative of general formula Ar—Mg—X, in which Ar is defined as above and X represents a halogen atom, or of an organolithium derivative of general formula Ar-Li, in which Ar is defined as above, with a product of general formula (IX):

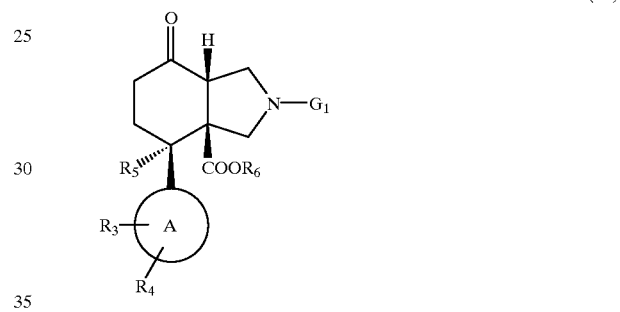

(IX)

in the form of optical isomers, preferably the levorotatory isomer, in which formula A, $R_3$, $R_4$, $R_5$, $R_6$ and $G_1$ are defined as above, under the usual conditions.

The reaction of an arylmagnesium derivative, obtained conventionally and optionally in the presence of anhydrous cerium(III) chloride under the conditions described by Imamoto (Tetrahedron Lett., 1985, p. 4763), with the ketone derivative of general formula (IX) is generally carried out in an organic solvent, such as diethyl ether or tetrahydrofuran, the reaction being carried out at a temperature of between 0° C. and the reflux temperature of the reaction mixture from a few minutes to 24 hours. However, it has been found to be particularly advantageous to carry out the reaction in toluene, optionally as a mixture with diethyl ether or tetrahydrofuran.

The reaction of an aryllithium derivative, obtained conventionally, with the ketone derivative of general formula (IX) is generally carried out in an organic solvent, such as diethyl ether or tetrahydrofuran, the reaction being carried out at a temperature of between −78° and −20° C. from a few minutes to 4 hours. However, it has been found to be particularly advantageous to carry out the reaction in toluene, optionally as a mixture with diethyl ether or tetrahydrofuran.

ii. According to a second particularly advantageous route, the compounds of general formula (III) in the form of optical isomers, preferably the dextrorotatory isomer, can be obtained from the compounds of general formula (IX) in the form of optical isomers, preferably the levorotatory isomer, via the formation of a stable and characterizable intermediate of general formula (XV) in the form of optical isomers, preferably the levorotatory isomer, characterized by the presence of an arylethylene functional group at the 7 position.

More specifically, the compounds of general formula III

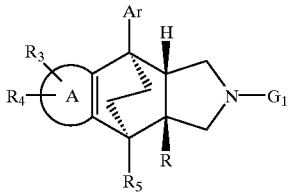

(III)

in the form of optical isomers, preferably the dextrorotatory isomer, in which formula A, $R_3$, $R_4$, $R_5$, Ar and R are as defined in general formula I and G1 represents a benzyl radical, can be obtained from compounds of general formula (IX):

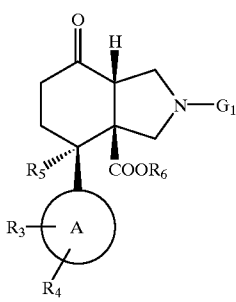

(IX)

in the form of optical isomers, preferably the levorotatory isomer, in which formula A, $R_3$, $R_4$, $R_5$, $R_6$ and $G_1$ are as defined above, via the formation of an intermediate of general formula (XV)

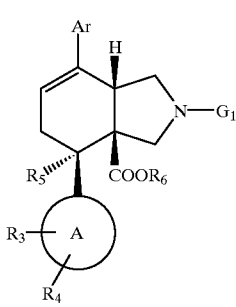

(XV)

in the form of optical isomers, preferably the levorotatory isomer, in which formula A, $R_3$, $R_4$, $R_5$, $R_6$, Ar and $G_1$ are as defined above.

The procedure developed successively involves:
either the condensation, at the 7 position, of a ketone derivative of general formula (IX) with hydrazine, to result in a hydrazone, followed by reaction with iodine to result, according to the Barton reaction (J. Chem. Soc., 1962, p. 470), in an iodoethylene derivative; followed by a palladium coupling reaction with an arylboronic acid, the Suzuki reaction (Tetrahedron Lett., 1979, p. 3437), of general formula Ar—B(OH)$_2$ or optionally with the trimeric anhydride of arylboronic acid, in which Ar is defined as above, or with an arylstannane, the Stille reaction (Angew. Chem. Int. Ed. Engl., 1986, p. 508), of general formula Ar—SnMe$_3$ in which Ar is defined as above, in order to result in this arylethylene intermediate of general formula (XV), the conversion of which by intramolecular cyclization of Friedel-Crafts type results in the expected product (III), or the reaction of a ketone derivative of general formula (IX) with trifluoromethanesulfonic anhydride, in order to result in an enol triflate at the 7 position (Org. Synth., 1990, p. 116); followed by a palladium coupling reaction with an arylboronic acid, the Suzuki reaction (Tetrahedron Lett., 1979, p. 3437), of general formula Ar—B(OH)$_2$ in which Ar is defined as above, or with an arylstannane, the Stille reaction (Angew. Chem. Int. Ed. Engl., 1986, p. 508), of general formula Ar—SnMe$_3$ in which Ar is defined as above, in order to result in this arylethylene intermediate of general formula (XV), the conversion of which by intramolecular cyclization of Friedel-Crafts type results in the expected product (III).

The ketone derivative of general formula (IX) is generally treated with an excess of hydrazine hydrate, from 3 to 20 molar equivalents, at reflux in a solvent, such as ethanol, from a few minutes to a few hours. The hydrazone thus obtained is then stirred with an excess of iodine, in the presence of an aliphatic tertiary amine, such as triethylamine, at a temperature in the region of 20° C. for a few hours in order to result in an iodoethylene derivative.

The ketone derivative of general formula (IX) is generally treated:
either with trifluoromethanesulfonic anhydride in the presence of an organic base, such as 2,6-di-tert-butyl-4-methylpyridine, in an organic solvent, such as dichloromethane, at a temperature in the region of room temperature for a few hours, according to Stang (Synthesis, 1980, p. 283), or with a bis(trifluoromethylsulfonyl)amide, such as N,N-bis(trifluoromethylsulfonyl)aniline, according to Mac-Murry (Tetrahedron Lett., 1983, p. 979), or 2-[N,N-bis(trifluoromethylsulfonyl)amino]pyridine, according to Comins (Tetrahedron Lett., 1992, p. 979), in the presence of a base, such as lithium diisoprolylamide, in an organic solvent, such as dichloromethane or 1,2-dimethoxyethane, in order to result in an enol triflate.

The coupling between the iodoethylene derivative or the enol triflate obtained above and an arylboronic acid obtained conventionally and optionally isolated in the trimeric anhydride form is generally carried out by stirring in a two-phase system composed of an organic solvent, preferably a mixture of toluene and methanol, and of a basic aqueous solution, preferably a 2N sodium carbonate solution, in the presence of a catalytic amount of palladium(0) derivative, preferably tetrakis(triphenylphosphine)-palladium, at a temperature in the region of the reflux temperature for a few hours, in order to result in the arylethylene compound of general formula (XV).

The coupling between the iodoethylene derivative or the enol triflate obtained above with an arylstannane obtained conventionally is generally carried out by stirring in a polar aprotic organic solvent, preferably dimethylformamide or N-methylpyrrolidone, in the presence of a catalytic amount of palladium(0) derivative, preferably tetrakis (triphenylphosphine)palladium, at a temperature of between 500 and 100° C. for a few hours, in order to result in the arylethylene compound of general formula (XV).

The intramolecular cyclization of Friedel-Crafts type of the compound of general formula (XV) to the product of general formula (III) is generally carried out under the conditions described above for the intramolecular cyclization of the products of general formula (VIII).

iii. According to a third route, a second preparation process makes it possible to obtain the compounds of general formula (III) in the form of optical isomers, preferably the dextrorotatory isomer, as defined above from the compounds of general formula (IX) in the form of optical isomers, preferably the levorotatory isomer, via the formation of the intermediate of general formula (XV) in the form of optical isomers, preferably the levorotatory isomer, which can optionally be isolated. This second process is very particularly advantageous when the aryl radical Ar represents a phenyl nucleus substituted, at the para or meta-para or meta-para-meta' positions, by electron-donating groups or a heterocyclic radical which is naturally rich in electrons or a heterocyclic radical suitably substituted by electron-donating groups, this second process consists in directly reacting, according to tandem intermolecular and then intramolecular cyclization reactions of Friedel-Crafts type, an aromatic or heterocyclic hydrocarbon Ar—H with a compound of general formula (IX) in an organic solvent in the presence of an excess of strong acid, such as trifluoromethanesulfonic acid, or optionally of a Lewis acid, such as aluminum chloride.

The procedure developed consists in condensing the product of general formula (IX) with an excess of trifluoromethanesulfonic acid (from 5 to 20 molar equivalents) in an organic solvent, such as dichloromethane, at a temperature in the region of room temperature from a few hours to several days. According to the number of molar equivalents and the concentration of trifluoromethanesulfonic acid, as well as the nature of the Ar radical and of the substituents which it carries, this reaction results either directly in the compounds of general formula (III) or in the compounds of general formula (XV) as intermediates, which are then cyclized as described above to compounds of general formula (III).

In addition, the compounds of general formula (I) or (III) can be obtained by functionalization of the substituents of the aromatic ring Ar of the corresponding compounds of general formula (I) or (III), by application or adaptation of the known methods for standard functionalizations, such as, and without implied limitation: functional substitution reactions (for example the replacement of a halogen atom by a cyano group by a palladium coupling), dealkylation reactions (for example by $BBr_3$) or alkylation reactions (in particular alkylation/cyclization reactions by the action of $BBr_2$).

Another subject of the present invention also relates to these compounds of general formula (XV):

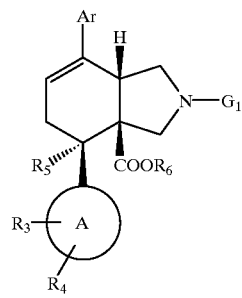

(XV)

in the form of optical isomers, preferably the levorotatory isomer, in which formula A, $R_3$, $R_4$, $R_5$ and Ar are as defined in general formula I, $G_1$ represents a benzyl radical and $R_6$ represents an alkyl radical comprising 1 to 3 carbon atoms.

The products of general formula (III)

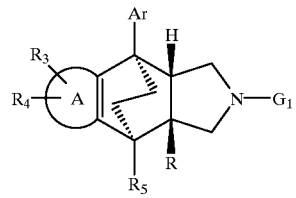

(III)

in which formula R represents a radical

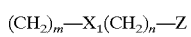

in which:
m is equal to 0,
$X_1$ represents a bond,
n is equal to 0 and
Z represents a —COOR, or —CON($R_7$) ($R_8$) radical can be obtained from a product of general formula (VIII), in which R represents a carboxyl radical, by esterification and amidation under the conditions described above, followed by cyclization by the action of trifluoromethanesulfonic acid under the conditions described above.

The products of general formula (III) in which R represents a radical

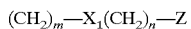

in which:
m is equal to 1,
$X_1$ represents a bond,
n is equal to 0 and
Z represents a —$COOR_6$, —CON($R_7$) ($R_8$) or PO($OR_9$)$_2$ radical can be obtained from a product of general formula:

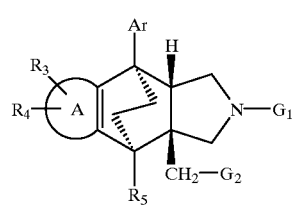

(XI)

in which formula A, Ar, $R_3$, $R_4$ and R are defined as above and $G_1$ represents a protective group for the amine functional group (benzyl, benzyloxycarbonyl or tert-butoxycarbonyl and $G_2$ represents a leaving group, such as a trifluoromethylsulfonyloxy radical.

More particularly, in order to obtain a product of general formula (III) in which R represents a radical

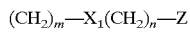

in which:

m is equal to 1, $X_1$ represents a bond, n is equal to 0 and

Z represents a carboxyl, —$COOR_6$, in which $R_6$ represents an alkyl radical, or —$CON(R_7)(R_8)$ radical, it is particularly advantageous to use the corresponding nitrile as an intermediate, which nitrile can be obtained by reaction of an alkali metal cyanide with the product of general formula (XI), the reaction being carried out in a polar organic solvent, such as dimethyl sulfoxide, at a temperature of between 0 and 50° C., which nitrile is hydrolyzed to the corresponding acid, which can then be esterified or amidated under the usual conditions.

More particularly, in order to obtain a product of general formula (III) in which R represents a radical

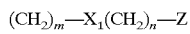

in which:

m is equal to 1, $X_1$ represents a bond, n is equal to 0 and

Z represents a —$PO(OR_9)_2$ radical, it is particularly advantageous to react a trialkyl phosphite with a product of general formula (XI) and then, optionally, to convert the phosphonate obtained to the corresponding phosphonic acid.

The products of general formula (III)

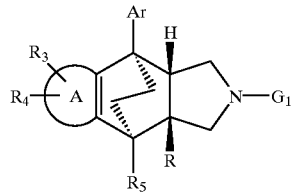

in which formula:

R represents a $(CH_2)_m$—$X_1$—$(CH_2)_n$—Z radical with m equal to 1, $X_1$ representing an oxygen or sulfur atom, n equal to 1 or 2 and Z representing a carboxyl, —$COOR_6$, in which $R_6$ represents an alkyl radical, or —$CON(R_7)(R_8)$ radical and $G_1$ represents a protective group for the amine functional group can be obtained by reaction of an ester or of an amide of general formula:

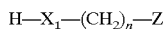

in which $X_1$, n and Z are defined as above, with a product of general formula (XI), the reaction being carried out in an anhydrous organic solvent, such as dioxane, in the presence of an alkali metal hydride, such as sodium hydride, optionally followed, depending on the situation, by saponification of the product of general formula (III) thus obtained.

The products of general formula (III) in which:

m is equal to 1, $X_1$ represents a bond, n is equal to 1, with it being possible for the methylene group to be substituted by a carboxyl or alkoxycarbonyl or carbamoyl or alkylcarbamoyl or dialkylcarbamoyl radical, $G_1$ represents a protective group for the amine functional group and Z represents a carboxyl, —$COOR_6$, in which $R_6$ represents an alkyl radical, or —$CON(R_7)(R_8)$ radical, can be obtained by reaction of a malonic acid, anionized beforehand, or of a malonic acid derivative, preferably a diester, with a product of general formula (XI), the reaction being carried out in an anhydrous organic solvent, such as dioxane, in the presence of an alkali metal hydride, such as sodium hydride, at a temperature of between 0° C. and the reflux temperature of the reaction mixture, followed, depending on the situation, by saponification, esterification, amidation or decarboxylation of the product of general formula (III) thus obtained.

The products of general formula (III) in which:

R represents an —NH—CO—T radical in which T is defined as above can be obtained by amidation of a product of general formula (III) in which:

$R_3$ is defined as above, $G_1$ represents a protective group of the amine functional group and R represents an amino radical by means of an acid of general formula T—CO—OH in which T is defined as above, under the conditions described above for the amidation of a product of general formula (VI).

The products of general formula (III) in which R represents an amino radical or the products of general formula (VI) can be obtained according to the methods which make it possible to convert a carboxyl radical to an amino radical without affecting the remainder of the molecule.

The carboxyl functional group of a product of general formula (III) or (I) is generally converted to the amino radical via an isocyanate which can be obtained by pyrolysis of the acid azide, which can itself be obtained by reaction of an alkali metal azide with the corresponding acid halide. The intermediate isocyanate thus obtained is conventionally condensed with benzyl alcohol and then the benzyl carbamate obtained is converted to the amino radical, either by hydrogenolysis or by acid hydrolysis under the conditions described above.

The products of general formula (III) in which R represents a 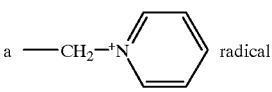 radical can be obtained by reaction of pyridine and of a strong acid or of a derivative of this acid with a product of general formula (XII):

(XII)

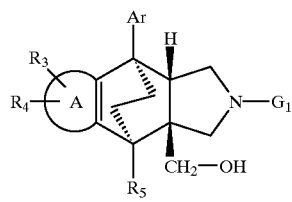

in which formula A, Ar, $R_3$, $R_4$ and $R_5$ are defined as above and $G_1$ represents a protective group for the amine functional group.

The products of general formula (VII) or of general formula (XII) can be obtained respectively by reduction of a product of general formula (I) or of a product of general formula (III) in which R represents a radical of general formula —$COOR_6$ in which $R_6$ preferably represents an alkyl radical comprising 1 to 3 carbon atoms.

The reduction is generally carried out by means of a lithium aluminum hydride, the reaction being carried out in an organic solvent, such as an ether, for example tetrahydrofuran, at a temperature of between 0 and 50° C.

2. According to a second route, the products of general formula (I) in the form of optical isomers, preferably dextrorotatory, can also be obtained from the products of general formula (IX) in the form of optical isomers, preferably the levorotatory isomer, by coupling of the side chain in order to form the product of general formula (VIII):

(XIII)

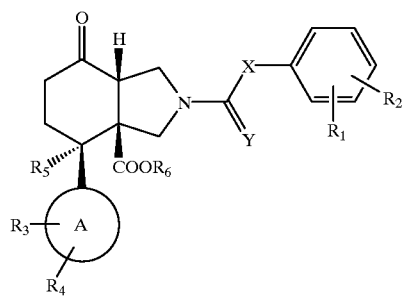

in the form of optical isomers, preferably the levorotatory isomer, in which formula A, $R_1$, $R_2$, $R_3$, $R_4$, $R_5$, $R_6$, X and Y are defined as above, and then, without distinction, by cyclization of the cycloperhydroisoindole nucleus and optionally modification of the R substituent:

The products of general formula (I), in which A, Ar, $R_1$, $R_2$, $R_3$, $R_4$, $R_5$, X and Y are defined as above and R represents a $COOR_6$ radical in which $R_6$ is defined as above, can also be obtained from a product of general formula (IX) in which $R_3$, $R_4$, $R_5$ and $R_6$ are defined as above and $G_1$ represents a hydrogen atom.

The product of general formula (IX)

(IX)

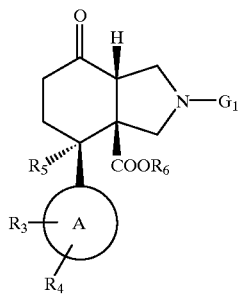

in which $G_1$ represents a hydrogen atom, is obtained from the product of general formula (IX), in which $G_1$ represents a protective group for the amino functional group, under the conditions described above for the preparation of a product of general formula (III) in which GI represents a hydrogen atom.

The product of general formula (IX) in the form of optical isomers, preferably the levorotatory isomer, in which formula $G_1$ represents a hydrogen atom is converted to the product of general formula:

(XIII)

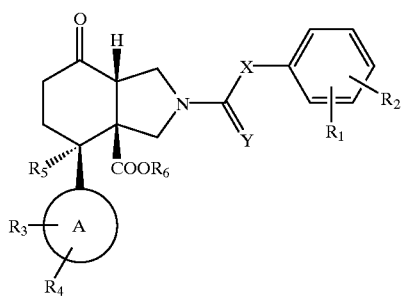

in the form of optical isomers, preferably the levorotatory isomer, in which formula A, $R_1$, $R_2$, $R_3$, $R_4$, $R_5$, $R_6$, X and Y are defined as above, the reaction being carried out, depending on the meanings of X and Y, in the following way:

the products of general formula (XIII), in which Y represents an oxygen or sulfur atom and X represents a —CO—, methylene, vinyldiyl, alken-1,1-diyl or cycloalkan-1,1-diyl group, can be obtained by reaction of an acid of general formula (II) or of its chloride or of its anhydride with a product of general formula (IX) in which Gi represents a hydrogen atom, the reaction being carried out under the conditions described above for the reaction of a product of general formula (II) with a product of general formula (III) in which $G_1$ represents a hydrogen atom, the products of general formula (XIII), in which Y represents an oxygen or sulfur atom and X represents an oxygen atom, can be obtained by reaction of a haloformate or of a halothioformate of general formula (IV) with a product of general formula (IX) in which Gi represents a hydrogen atom, the reaction being carried out under the conditions described above for the reaction of a product of general formula (IV) with a product of general formula (III) in which $G_1$ represents a hydrogen atom, the products of general formula (XIII), in which Y represents an oxygen or sulfur atom and X represents an NH group, can be obtained by reaction of an isocyanate or of an isothiocyanate of general formula (V) with a product of general formula (IX) in which Gi represents a hydrogen atom, the reaction being carried out under the conditions described above for the reaction of a product of general formula (V) with a product of general formula (III) in which $G_1$ represents a hydrogen atom.

The product of general formula (XIII) in the form of optical isomers, preferably the levorotatory isomer, is converted to the product of general formula:

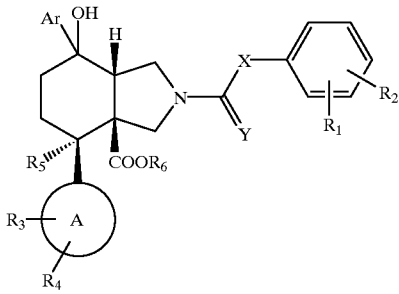

(XIV)

in the form of optical isomers, preferably the levorotatory isomer, in which formula A, Ar, $R_1$, $R_2$, $R_3$, $R_4$, $R_5$, $R_6$, X and Y are defined as above, by reaction of a metallic derivative of general formula Ar—Mg—X or Ar—Li, in which X represents a halogen atom, with a product of general formula (XIII), the reaction being carried out under the conditions described above for the reaction of an organomagnesium or organolithium derivative of general formula Ar—Mg—X or Ar—Li with a product of general formula (IX).

The product of general formula (XIV) in the form of optical isomers, preferably the levorotatory isomer, is converted to the product of general formula (I) in the form of optical isomers, preferably the dextrorotatory isomer, in which formula A, Ar, $R_1$, $R_2$, $R_3$, $R_4$, $R_5$, $R_6$, X and Y are defined as above, by the action of trifluoromethanesulfonic acid or of a Lewis acid on the product of general formula (XIV), the reaction being carried out under the conditions described above for the action of trifluoromethanesulfonic acid or of a Lewis acid on a product of general formula (VIII).

The reaction of an aromatic hydrocarbon or of an aromatic heterocycle Ar—H, as defined above, in the presence of trifluoromethanesulfonic acid or of a Lewis acid, with a product of general formula (XIII), in which $R_1$, $R_2$, $R_3$, $R_4$, $R_5$, $R_6$, X and Y are defined as above, results in a product of general formula (I) in which Ar is defined as above and R represents a COOR$_6$ radical in which $R_6$ represents an alkyl radical comprising 1 to 3 carbon atoms.

The products of general formula (I) in the form of optical isomers, preferably the dextrorotatory isomer, in which formula:
A, Ar, $R_1$, $R_2$, $R_3$, $R_4$, $R_5$, X and Y are defined as above and R represents a radical

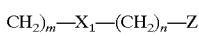

in which m, n, $X_1$ and Z are defined as above can also be prepared from a product of general formula (VII) in the form of optical isomers, preferably the dextrorotatory isomer, under the conditions described above for the preparation of the products of general formula (III) from a product of general formula (XI), after replacement of the hydroxyl radical of the product of general formula (VII) by a leaving group, such as a trifluoromethanesulfonyloxy radical.

As described in Applications WO 98/29390 and FR 2,772,764, the products of general formula (X) can be obtained by esterification of the corresponding 3-oxocyclohex-1-ene-1-carboxylic acids,

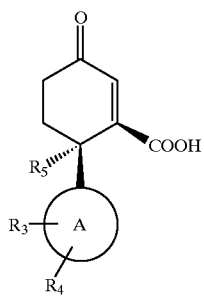

in which A, $R_3$, $R_4$ and $R_5$ are defined as above, by means of an aliphatic alcohol comprising 1 to 3 carbon atoms, in the presence of an inorganic acid, such as hydrochloric acid or sulfuric acid, at a temperature of between 0° C. and the reflux temperature of the reaction mixture, or by means of an alkyl halide (iodide), in the presence of an organic base, such as 1,8-diazabicyclo[5.4.0]undec-7-ene, or an inorganic base, such as cesium carbonate, the reaction being carried out in a solvent chosen from tetrahydrofuran, dimethylformamide, acetone or dioxane.

3-Oxocyclohex-1-ene-1-carboxylic acids, in which $R_3$, $R_4$ and Rs are defined as above, can be obtained from 3-oxo-6-phenylcyclohexane-1-ol-1-carboxylic acids,

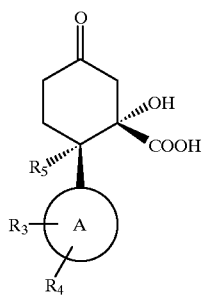

in which A, $R_3$, $R_4$ and $R_5$ are defined as above, either by thermal dehydration, by heating at a temperature in the region of 190° C. (according to J. Org. Chem., 1971, p. 3707) or by heating in refluxing toluene in the presence of p-toluenesulfonic acid, or by reacting with an inorganic base, such as sodium hydroxide, at a temperature of between 0 and 50° C.

3-Oxo-6-phenylcyclohexane-1-ol-1-carboxylic acids, in which $R_3$, $R_4$ and $R_5$ are defined as above, can be obtained by reaction of pyruvic acids,

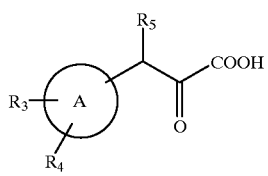

where A, $R_3$, $R_4$ and $R_5$ are defined as above, or optionally of the corresponding esters, more particularly in the case where $R_5$ does not represent a hydrogen atom, with methyl vinyl ketone, the reaction generally being carried out in aqueous/alcoholic medium, such as a methanol/water mixture, in the presence of an inorganic base, such as sodium hydroxide (according to J. Org. Chem., 1971, 3707).

Pyruvic acids can be obtained, more particularly in the case where $R_5$ represents a hydrogen atom, either by hydrolysis of the corresponding α-acetamidovinyl acids,

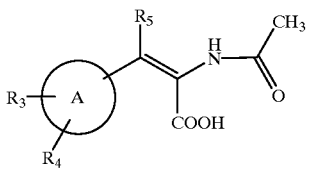

where A, $R_3$, $R_4$ and $R_5$ are defined as above, by heating in hydrochloric acid, according to Org. Synth., 1943, p. 519, or by hydrolysis of the corresponding hydantoins,

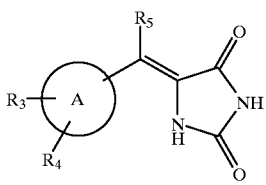

where A, $R_3$, $R_4$ and $R_5$ are defined as above, by heating in 20% sodium hydroxide solution, according to Org. Synth. Coll. Vol. V, p. 627.

α-Acetamidovinyl acids can be obtained, from the corresponding aldehydes

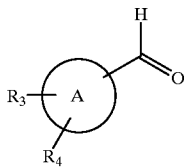

where A, $R_3$ and $R_4$ are defined as above, according to Org. Synth., 1939, p. 1, by reaction with N-acetylglycine in refluxing acetic anhydride in the presence of sodium acetate. The intermediate azlactones thus obtained are then hydrolyzed to a-acetamidocinnamic acids by heating at reflux in aqueous acetone.

Hydantoins can be obtained by heating the corresponding aldehydes, according to Org. Synth. Coll. Vol. V, p. 267, with hydantoin in the presence of an organic base, such as piperidine, at a temperature in the region of 130° C.

Pyruvates can be obtained, more particularly in the case where $R_5$ does not represent a hydrogen atom but an alkyl or alkylthio radical, from carboxylic acids,

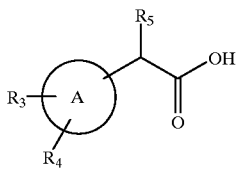

by reaction of the corresponding dianion, generally obtained by reaction of an organic base, such as n-butyllithium, with the acid, with ethyl oxalate at a temperature in the region of −70° C., followed by decarboxylation, the reaction being carried out under the conditions described in Tetrahedron Lett., 1981, 2439–42.

The reaction mixtures obtained by the various processes described above are treated according to conventional physical methods (evaporation, extraction, distillation, chromatography, crystallization, for example) or conventional chemical methods (formation of salts, for example).

The compounds of formula (I) can optionally be converted into addition salts with an inorganic or organic acid by the action of such an acid in an organic solvent, such as an alcohol, a ketone, an ether or a chlorinated solvent. These salts also form part of the invention.

The products of general formula (I) can be provided in the form of non-toxic and pharmaceutically acceptable salts. These non-toxic salts comprise salts with inorganic acids (hydrochloric, sulfuric, hydrobromic, phosphoric or nitric acids) or with organic acids (acetic, propionic, succinic, maleic, hydroxymaleic, benzoic, fumaric, methanesulfonic, trifluoroacetic or oxalic acids) or with inorganic bases (sodium hydroxide, potassium hydroxide, lithium hydroxide, calcium hydroxide) or organic bases (tertiary amines, such as triethylamine, piperidine, benzylamine), depending on the nature of the compounds of general formula (I).

The following examples are presented by way of illustration of the present invention and do not limit the present invention.

EXAMPLE 1

Preparation of the dextrorotatory enantiomer of methyl (3aRS,4SR,9SR,9aRS)-4,9-ethano-2-[2-(2-methoxyphenyl)vropenoyl]-9-(4-methylphenyl)- 2,3,3a,4,9,9a-hexahydro-1H-benzo[f]isoindole-3a-carboxylate Stage A 358 g (2.52 mol) of methyl iodide and 361 g (2.38 mol) of 1,8-diazabicyclo[5.4.0]undec-7-ene are successively added to a solution of 428 g (1.98 mol) of (RS)-3-oxo-6-phenylcyclohex-1-ene-1-carboxylic acid, which can be obtained according to J. Org. Chem., 1971, 36, 3707, in 4.5 dm³ of acetone and then the reaction mixture is brought to reflux for five hours. The acetone is subsequently distilled off and the residue is stirred with 2.5 dm³ of water. After cooling to 10° C., the precipitate formed is filtered off, washed with ice-cold water and then dried at 30° C. 423 g (93%) of methyl (RS)-3-oxo-6-phenylcyclohex-1-ene-1-carboxylate are thus obtained in the form of a yellow powder, the characteristics of which are as follows:

melting point=66° C.

N.M.R. spectrum (300 MHz, CDCl₃, d in ppm): 2.1–2.4 (mt, 4H, H at 4 and at 5), 3.72 (s, 3H, CH₃), 4.25 (dt, 1H, H at 6), 6.88 (s, 1H, H at 2), 7.2–7.52 (mt, 5H, aromatic protons).

Stage B

Preparation of methyl (R,S)-3-oxo-6-phenylcyclohex-1-enecarboxylate in the resolved levorotatory form 202 g of methyl (R,S)-3-oxo-6-phenylcyclohex-1-enecarboxylate-in the racemic form are dissolved with vigorous stirring in 7.75 dm³ of cyclohexane at 30° C. and the insoluble particles are extracted by settling (Solution 1). 513.6 g of K₂HPO₄ are dissolved in 29.43 dm³ of distilled water in a 50 dm³ stirred reactor (Solution 2). Solution 2 is adjusted to a pH of 7.2 with 85% (w/%) H₃PO₄, heated to 30° C. and mixed with Solution 1. 2.8 dm³ of a solution of Candida antartica, "fraction B", lipase (e.g. Chirazyme® L2, solution sold by Boehringer Mannheim) is subsequently added to the reactor. The reaction is carried out with vigorous stirring at 30° C. The enantioselective resolution is monitored by chiral HPLC on the following column: Chiralpak® AD (Daicel Chemical Industries Ltd), mobile phase: heptane/ethanol 90/10 (V/V), UV detection: 220 nm, flow rate: 1 ml/min. After 342 h, the organic phase, in the form of an emulsion (Solution 3), is separated from the aqueous phase by settling. 7.75 dm$^3$ of cyclohexane and 1.25 dm$^3$ of ethanol are mixed with Solution 3. 15.5 dm$^3$ of the upper phase are separated from the lower phase comprising 2.4 dm$^3$ of water and of ethanol. The upper phase is concentrated and dried under vacuum at 40° C., resulting in 53.5 g of a yellow solid: methyl (R,S)-3-oxo-6-phenylcyclohex-1-enecarboxylate in the resolved levorotatory form with a 93% enantiomeric excess, the characteristics of which are as follows:

optical rotation: $[a]_{365}^{20}$=−183.3+/−2.20 (c=0.5, methanol)

HPLC (column: Chiralpak® AD, sold by Daicel Chemical Industries Ltd, mobile phase: heptane/ethanol 90/10 (v/v), UV detection: 220 nm, flow rate: 1 ml/min):

Retention time: methyl (R,S)-3-oxo-6-phenylcyclohex-1-enecarboxylate in the resolved levorotatory form: 8.4 min Stage C A solution of 95 g (0.413 mol) of the levorotatory enantiomer of methyl (R,S)-6-phenyl-3-oxocyclohexene-1-carboxylate, with an enantiomeric excess of greater than 90%, and of 0.47 cm$^3$ of trifluoroacetic acid in 500 cm$^3$ of dichloromethane is brought to reflux. 138.5 g (0.496 mol) of N-(n-butoxymethyl)-N-(trimethylsilylmethyl)benzylamine, which can be obtained according to Chem. Pharm. Bull., 1985, 276, are then added dropwise over fifteen minutes and reflux is maintained for ten minutes. The reaction mixture is then cooled to 20° C. After stirring during a saturated aqueous sodium hydrogencarbonate solution, the organic phase is concentrated and the yellow oil obtained is purified by silica gel chromatography (230–400 mesh), elution being carried out with a cyclohexane/ethyl acetate (90/10 and then 80/20 by volume) mixture. The oil thus obtained is taken up in 645 cm$^3$ of cyclohexane and the organic phase is washed successively with an N aqueous methanesulfonic acid solution and then.with distilled water. 118.2 g (79%) of the levorotatory enantiomer of methyl (3aRS,4SR,7aSR)-2-benzyl-7-oxo-4-phenylperhydroisoindole-3a-carboxylate are then obtained in the form of a viscous yellow oil, the characteristics of which are as follows:

mass spectrum (EI): M/Z=363 (M$^+$)

optical rotation: $[\alpha]_{365}^{20}$=−58.7+/−1° (c=0.5/methanol)

Stage D 76.2 g (0.445 mol) of 4-bromotoluene and 10.8 g (0.445 mol) of magnesium turnings in 500 cm$^3$ of diethyl ether are heated at reflux for one hour. After cooling to a temperature in the region of 5° C., a solution of 124.65 g (0.343 mol) of levorotatory enantiomer methyl (3aRS,4SR,7aRS)-2-benzyl-7-oxo-4-phenylperhydroisoindole-3a-carboxylate in 500 cm$^3$ of toluene is added. The reaction mixture is stirred for one hour at a temperature in the region of 20° C. and then hydrolyzed with 450 cm$^3$ of a saturated aqueous ammonium chloride solution. The aqueous phase is separated by settling and extracted with two times 500 cm$^3$ of ethyl acetate. The organic phases are combined, washed successively with 100 cm$^3$ of distilled water and 100 cm$^3$ of a saturated aqueous sodium chloride solution, dried over magnesium sulfate and concentrated under reduced pressure. After purification by flash chromatography on silica gel (230–400 mesh), elution being carried out with cyclohexane/ethyl acetate (95/5 and then 80/20 by volume) mixtures, 135.9 g (87%) of the levorotatory enantiomer of methyl (3aRS,4SR,7RS,7aRS)-2-benzyl-7-hydroxy-7-(4-methylphenyl)-4-phenylperhydroisoindole-3a-carboxylate are obtained in the form of a white solid, the characteristics of which are as follows:

optical rotation: $[\alpha]_{365}^{20}$=−60.3+/−1° (c=0.5, methanol)

$^1$H N.M.R. spectrum (250 MHz, CDCl$_3$, d in ppm): 1.84 and 2.60 (d mt and mt, J=12.5 Hz, each 1H, CH$_2$ at 5), from 2.05 to 2.20 (mt, 2H, 1H of the CH$_2$ at 1 and 1H of the CH$_2$ at 6), 2.32 (s, 3H, ArCH$_3$), 2.40 and 2.95 (2d, J=10.5 Hz, each 1H, CH$_2$ at 3), 2.45 (mt, 1H, the other H of the CH$_2$ at 6), 2.64 (mt, 1H, the other H of the CH$_2$ at 1), 2.85 (mt, 1H, H at 7a), 3.32 (s, 3H, COOCH$_3$), 3.40 and 3.70 (2d, J=12.5 Hz, each 1H, NCH$_2$Ar), 3.50 (dd, J=12.5 and 3 Hz, 1H, H at 4), 6.68 (s, 1H, OH at 7), from 7.00 to 7.50 (mt, 10H, aromatic H at 4 and aromatic H of the benzyl), 7.12 and 7.40 (2d, J=8 Hz, each 2H, H at the ortho and meta positions of the aromatic at 7).

Stage E 250 cm$^3$ of trifluoromethanesulfonic acid are added dropwise to a solution, maintained at a temperature in the region of 0° C., of 135.9 g (0.335 mol) of the levorotatory enantiomer of methyl (3aRS,4SR,7RS,7aRS)-2-benzyl-7-hydroxy-7-(4-methylphenyl)-4-phenylperhydroisoindole-3a-carboxylate in 1 dm$^3$ of dichloromethane. The reaction mixture is stirred for 30 minutes at a temperature in the region of 0° C. and for 2 hours at a temperature in the region of 20° C. and then cooled to a temperature in the region of 0° C. 200 cm$^3$ of distilled water are then added and the pH of the aqueous phase is then brought to between 8 and 9 by addition of 450 cm$^3$ of a 4N aqueous sodium hydroxide solution. The organic phase is separated by settling, washed successively with 100 cm$^3$ of distilled water and 100 cm$^3$ of a saturated aqueous sodium chloride solution, dried over magnesium sulfate and concentrated under reduced pressure. 94.12 g (72%) of the dextrorotatory enantiomer of methyl (3aRS,4SR,9SR,9aRS)-2-benzyl-4,9-ethano-9-(4-methylphenyl)-2,3,3a,4,9,9a-hexahydro-1H-benzo[f]isoindole-3a-carboxylate are thus obtained in the form of a white solid, the characteristics of which are as follows:

optical rotation: $[\alpha]_{365}^{20}$=+38.2+/−1° (c=0.5, methanol)

$^1$H N.M.R. spectrum (300 MHz, CDCl$_3$, d in ppm): 1.61, 1.90 and 2.67 (3 mts, respectively 1H, 1H and 2H, CH$_2$CH$_2$), from 2.50 to 2.60 (mt, 2H, 1H of the CH$_2$ at 1 and 1H CH$_2$ at 3), 2.57 (s, 3H, ArCH$_3$), 2.95 (d, J=10 Hz, the other H of the CH$_2$ at 1), 3.37 (d, J=10 Hz, the other H of the CH$_2$ at 3), 3.44 (broad d, J=10 Hz, 1H, H at 9a), 3.54 and 3.85 (2d, J=12.5 Hz, each 1H, NCH$_2$Ar), 3.57 (broad s, 1H, H at 4), 3.72 (s, 3H, COOCH$_3$), 6.70 (broad d, J=7.5 Hz, 1H, H at 8), from 7.10 to 7.60 (mt, 12H, H at 5, H at 6, H at 7, H at the ortho and meta positions of the aromatic at 9 and aromatic H of the benzyl).

Stage F 93.62 g (0.214 mol) of the dextrorotatory enantiomer methyl (3aRS,4SR,9SR,9aRS)-2-benzyl-4,9-ethano-9-(4-methylphenyl)-2,3,3a,4,9,9a-hexahydro-1H-benzo[f]isoindole-3a-carboxylate, in solution in 1.5 dm$^3$ of methanol, are reduced by 41 g of ammonium formate in the presence of 9.4 g of 10%. (w/%) palladium-on-charcoal by heating at reflux for two hours. After cooling, the catalyst is separated by filtration and rinsed with three times 100 cm$^3$ of methanol and the filtrate is concentrated under reduced pressure. The residue is dissolved in 500 cm$^3$ of ethyl acetate and the organic phase is washed successively with 2 times 100 cm$^3$ of a saturated aqueous sodium hydrogen carbonate solution, 100 cm$^3$ of distilled water and 100 cm$^3$ of a saturated aqueous sodium chloride solution, dried over magnesium sulfate and concentrated under reduced pressure. 68.19 g of the dextrorotatory enantiomer of methyl (3aRS,4SR,9SR,9aRS)-4,9-ethano-9-(4-methylphenyl)-2,3,3a,4,9,9a-hexahydro-1H-benzo[f]isoindole-3a-carboxylate are obtained in the form of a white solid, the characteristics of which are as follows:

optical rotation: $[\alpha]_{365}^{20}$=+44.1+/−0.9° (c=0.5, methanol)

$^1$H N.M.R. spectrum (250 MHz, CDC13, d in ppm): 1.56, 1.78 and 2.24 (3 mts, respectively 1H, 1H and 2H, CH$_2$CH$_2$), 2.42 (s, 3H, ArCH$_3$), 2.79 and 2.96 (2 dd, respectively J=12.5 and 5.5 Hz and J=1.25 and 8 Hz, each 1H, CH$_2$ at 1), 3.10 and 3.39 (2 d, J=12.5 Hz, each 1H, CH$_2$ at 3), 3.30 (mt, 1H, H at 9a), 3.51 (broad s, 1H, H at 4), 3.60 (s, 3H, COOCH$_3$), 6.56 (broad d, J=7.5 Hz, 1H, H at 8), from 6.95 to 7.45 (mt, 7H, H at 5, H at 6, H at 7 and H at the ortho and meta positions of the aromatic at 9).

Stage G

A solution of 18.6 cm$^3$ of oxalyl chloride in 18 cm$^3$ of dichloromethane is added dropwise to a solution of 38.6 g (0.216 mol) of 2-(2-methoxyphenyl)propenoic acid, which can be obtained according to WO 98/29390, in 300 cm$^3$ of dichloromethane and 1.8 cm$^3$ of N,N-dimethylformamide. The reaction mixture is stirred for a further two hours at a temperature in the region of 20° C., then cooled to a temperature in the region of 0° C. and run dropwise into a solution of 68.09 g (0.196 mol) of the dextrorotatory enantiomer of methyl ($^3$aRS,4SR,9SR,9aRS)-4,9-ethano-9-(4-methylphenyl)-2,3,3a,4,9,9a-hexahydro-1H-benzo[f] isoindole-3a-carboxylate in 500 cm$^3$ of dichloromethane and 55.4 cm$^3$ of triethylamine, the temperature being maintained in the region of 0° C. The reaction mixture is stirred for a further one hour at a temperature in the region of 0° C., then overnight at a temperature in the region of 20° C. and poured into 350 cm$^3$ of distilled water. The organic phase is separated by settling, washed with 450 cm$^3$ of an N aqueous hydrochloric acid solution and then 200 cm$^3$ of a saturated aqueous sodium chloride solution, dried over magnesium sulfate and concentrated under reduced pressure. After purification by flash chromatography on silica gel (230–400 mesh), elution being carried out with a cyclohexane/ethyl acetate (70/30 by volume) mixture, 93.96 g (94%) of the dextrorotatory enantiomer of methyl (3aRS,4SR,9SR,9aRS)-4,9-ethano-2-[2-(2-methoxyphenyl)propenoyl]-9-(4-methylphenyl)-2,3,3a,4,9,9a-hexahydro-1H-benzo[f] isoindole-3a-carboxylate are obtained in the form of a white solid, the characteristics of which are as follows:

optical rotation: $[\alpha]_{365}^{20}$=+60.8+/−1° (c=0.5, methanol)

$^1$H N.M.R. spectrum (250 MHz, d6-DMSO, at a temperature of 383 K, d in ppm): 1.44, 1.68 and from 2.00 to 2.30 (3 mts, respectively 1H, 1H and 2H, CH$_2$CH$_2$), 2.40 (s, 3H, ArCH$_3$), from 3.35 to 3.50 (mt, 3H, CH$_2$ at 1 and H at 9a), 3.46 (mt, 1H, H at 4), 3.55 (s, 3H, COOCH$_3$), 3.60 and 4.10 (2d, J=12.5 Hz, each 1H, CH$_2$ at 3), 3.73 (s, 3H, ArOCH$_3$), 5.54 and 5.70 (2s, each 1H, =CH$_2$), 6.46 (broad d, J=7.5 Hz, 1H, H at 8), from 6.90 to 7.40 (mt, 11H, H at 5, H at 6, H at 7, H at the ortho and meta positions of the aromatic at 9 and aromatic H at the ortho, meta and para positions with respect to the OCH$_3$).

EXAMPLE 2

Preparation of the dextrorotatory enantiomer of (3aRS,4SR,9SR,9aRS)-4,9-ethano-2-[2-(2-methoxylhenvl)prolenoyl]-9-(4-methylphenyl)-2,3,3a,4,9,9a-hexahydro-1H-benzo[f] isoindole-3a-carboxylic acid 93.46 g (0.184 mol) of the dextrorotatory enantiomer of methyl (3aRS,4SR,9SR,9aRS)-4,9-ethano-2-[2-(2-methoxyphenyl)propenoyl]-9-(4-methylphenyl)-2,3,3a,4,9, 9a-hexahydro-1H-benzo[f]isoindole-3a-carboxylate are heated at reflux for three hours in 1.6 dm$^3$ of ethanol in the presence of 370 cm$^3$ of a normal aqueous sodium hydroxide solution. The reaction mixture is subsequently concentrated under reduced pressure and the residue dissolved in 500 cm$^3$ of distilled water. The aqueous phase is washed with three times 250 cm$^3$ of diethyl ether and then acidified with 400 cm$^3$ of an N aqueous hydrochloric acid solution to a pH in the region of 2. The aqueous phase is extracted with 1 dm$^3$ and then two times 200 cm$^3$ of dichloromethane and the combined organic phases are washed with three times 200 cm$^3$ of water, dried over magnesium sulfate and then concentrated under reduced pressure. After purification by flash chromatography on silica gel (230–400 mesh), elution being carried out with a dichloromethane/methanol (97.5/2.5 by volume) mixture, and then by two successive recrystallizations from 850 and then 740 cm$^3$ of isopropanol, 46.11 g of the dextrorotatory enantiomer of (3aRS,4SR,9SR,9aRS)-4, 9-ethano-2-[2-(2-methoxyphenyl)propenoyl]-9-(4-methylphenyl)-2,3,3a,4,9,9a-hexahydro-1H-benzo[f] isoindole-3a-carboxylic acid, with an enantiomeric purity of greater than 99.9%, are obtained in the form of a white solid, the characteristics of which are as follows:

melting point=233° C.

mass spectrum (EI): M/Z=493 (M$^+$) and 449 (M$^+$—CO$_2$)

optical rotation: $[\alpha]_{365}^{20}$=+71.3+/−1.2° (c=0.5, methanol).

HPLC:

Stationary phase: chiral silica carrying (3,5-dinitrobenzoyl)-R-phenylalanine grafts disclosed in WO 98/29390, Mobile phase: dichloromethane/ethanol/n-heptane/trifluoroacetic acid (50/1/50/0.1 by volume) mixture at a flow rate of 2 cm$^3$/min Retention time: 9.53 min.

EXAMPLE 3

Preparation of (3aRS,4SR,9SR,9aRS)-9-(benzothien-2-yl)-4,9-ethano-2-[2-(2-methoxyphenyl)propenoyl)]-2,3,3a,4,9, 9a-hexahydro-1H-benzo[f]isoindole-3a-carboxylic acid, dextrorotatory enantiomer The preparation is carried out according to Stages A, B and C of Example 1 and then as described hereinbelow:

Stage D:

A solution of 100 g (0.275 mol) of the levorotatory enantiomer of methyl (3aRS,4RS,7aSR)-2-benzyl-4-phenyl-7-oxoperhydroisoindole-3a-carboxylate and of 50 g (1 mol) of hydrazine hydrate in 750 cm$^3$ of ethanol is brought to reflux for one and a half hours. After concentrating the ethanol under reduced pressure, the residue is taken up in 400 cm$^3$ of dichloromethane and the organic phase is washed with distilled water and then with a saturated aqueous sodium chloride solution, dried over magnesium sulfate and concentrated under reduced pressure. 100 g (960%) of the levorotatory enantiomer of methyl (3aRS, 4SR,7aRS)-2-benzyl-7-hydrazono-4-phenylperhydroisoindole-3a-carboxylate are thus obtained in the form of a yellow oil used as is in the following stage.

Stage E

A solution of 134.5 g (0.53 mol) of iodine in 600 cm$^3$ of tetrahydrofuran is added dropwise to a solution of 100 g (0.265 mol) of the levorotatory enantiomer of methyl (3aRS, 4SR,7aRS)-2-benzyl-7-hydrazono-4-phenylperhydroisoindole-3a-carboxylate and of 110 cm$^3$ (0.795 mol) of triethylamine in 1.4 dm$^3$ of tetrahydrofuran. After stirring for one hour at room temperature, the reaction mixture is concentrated under reduced pressure to approximately 500 cm$^3$ and then 1 dm$^3$ of ethyl acetate is added. The organic phase is washed with two times 800 cm$^3$ of a saturated aqueous sodium hydrogencarbonate solution and then with two times 500 cm$^3$ of a saturated aqueous sodium thiosulfate solution, dried over magnesium sulfate and concentrated under reduced pressure. After purification by chromatography on silica gel (230–400 mesh), elution being carried out with a cyclohexane/ethyl acetate (95/5 by volume) mixture, 56 g (45%) of the levorotatory enantiomer of methyl (3aRS,4SR,7aRS)-2-benzyl-7-iodo-4-phenyl-1,2,3,4,5,7a-hexahydroisoindole-3a-carboxylate are obtained in the form of a viscous brown oil, the characteristics of which are as follows:

mass spectrum (EI): M/Z 473 (M+)
optical rotation: $[\alpha]_{365}^{20}$=−51.8+/−1° (c=0.5, methanol)

Stage F 10.43 cm³ (69 mmol) of N,N,N',N'-tetramethylethylenediamine are added dropwise at −40° C. to a solution of 13.41 g (63 mmol) of 5-bromobenzothiophene, which can be obtained according to J. Het. Chem., 1988, 25, 1271–2, in 100 cm³ of tetrahydrofuran. After stirring for fifteen minutes at −40° C., 43.3 cm³ of a 1.6M solution (0.069 mol) of n-butyllithium in hexane are added dropwise and the reaction mixture is stirred for two hours between −30 and −40° C. 7.86 cm³ (69 mmol) of trimethyl borate are subsequently added at −30° C. and stirring is maintained for two hours while allowing the temperature to return to between 0 and −5° C. The red solution obtained is hydrolyzed by addition of 80 cm³ of a 5N aqueous hydrochloric acid solution and then 200 cm³ of ethyl acetate are added. The organic phase is separated by settling, washed with a saturated aqueous sodium chloride solution, dried over magnesium sulfate and concentrated under reduced pressure. 9.3 g (76%) of a yellow powder are thus obtained composed to an overwhelming extent of benzothiophene-2-boronic acid in trimeric anhydride form, used as is in the continuation of the synthesis, the characteristics of which are as follows:

mass spectrum (EI): M/Z=480 (M+)
melting point=260–63° C.

Stage G

A solution of 9.3 g (17.3 mmol) of benzothiophene-2-boronic acid trimeric anhydride in 100 cm³ of methanol and 400 cm³ of a 2N aqueous sodium carbonate solution are successively added to a solution of 22.36 g (47 mmol) of the levorotatory enantiomer of methyl (3aRS,4SR,7aRS)-2-benzyl-7-iodo-4-phenyl-1,2,3,4,5,7a-hexahydroisoindole-3a-carboxylate and of 6.03 g (5.2 mmol) of tetrakis (triphenylphosphine)palladium in 250 cm³ of 1,2-dimethoxyethane, the reaction mixture is then brought to reflux for two hours and stirring is maintained overnight at room temperature. After returning to a temperature in the region of 20° C., the reaction mixture is extracted with 800 cm³ of ethyl acetate and then the organic phase is washed with a saturated aqueous sodium chloride solution, dried over magnesium sulfate and concentrated under reduced pressure. The brown residue obtained is purified by flash chromatography on silica gel (230–400 mesh), elution being carried out with a cyclohexane/ethyl acetate (80/20 by volume) mixture. 11.04 g (50%) of the levorotatory enantiomer of methyl (3aRS,4SR,7aRS)-2-benzyl-4-phenyl-7-(2-benzothienyl)-1,2,3,4,5,7a-hexahydroisoindole-3a-carboxylate are thus obtained in the form of a yellow foam, the characteristics of which are as follows:

mass spectrum (EI): M/Z=479 (M+)
¹H N.M.R. spectrum (400 MHz, CDCl₃, d in ppm): 2.53 (dt, J=18 and 5 Hz, 1H), from 2.80 to 2.95 (mt, 1H), 2.84 (AB, J=10 Hz, 2H), 3.17 (t, J=10 Hz, 1H), 3.48 (dd, J=9.5 and 5 Hz, 1H), from 3.55 to 3.70 (mt, 4H), 3.56 (s, 3H), 6.44 (mt, 1H), from 7.05 to 7.40 (mt, 13H), 6.67 (dd, J=6.5 and 2 Hz, 1H), 7.75 (broad d, J=7 Hz, 1H).
optical rotation: $[a]_{3652}^{20}$=−28.1+/−0.70 (c=0.5, dichloromethane).

Stage H

The prepation is carried out as in Stage E of Example 1 but from 11 g (23 mmol) of the levorotatory enantiomer of methyl (3aRS,4SR,7aRS)-2-benzyl-4-phenyl-7-(2-benzothienyl)-1,2,3,4,5,7a-hexahydroisoindole-3a-carboxylate in 100 cm³ of dichloromethane and from 15 cm³ of trifluoromethanesulfonic acid. After washing with diisopropyl ether, 7.96 g (72%) of the dextrorotatory enantiomer of methyl (3aRS,4SR,9SR,9aRS)-9-(2-benzothienyl)-2-benzyl-4,9-ethano-2,3,3a,4,9,9a-hexahydro-1H-benzo[f]isoindole-3a-carboxylate are thus obtained in the form of a viscous yellow oil, used as is in the continuation of the synthesis, the characteristics of which are as follows:

mass spectrum (EI): M/Z=479 (M+)
optical rotation: $[\alpha]_{365}^{20}$=+22.7+/−0.70 (c=0.5, dichloromethane).

Stage I

A solution of 4.80 g (10 mmol) of the dextrorotatory enantiomer of methyl (3aRS,4SR,9SR,9aRS)-9-(2-benzothienyl)-2-benzyl-4,9-ethano-2,3,3a,4,9,9a-hexahydro-1H-benzo[f]isoindole-3a-carboxylate and of 3.37 cm³ (50 mmol) of vinyl chloroformate in 100 cm³ of dichloromethane is stirred overnight at room temperature. After concentrating under reduced pressure, the residue is dissolved in 60 cm³ of an N solution of hydrochloric acid in methanol and brought to reflux for two hours. After cooling, 100 cm³ of distilled water are added, the pH is brought to 8 by addition of an N aqueous sodium hydroxide solution and extraction is carried out with ethyl acetate. The organic phase is dried over sodium sulfate and then concentrated under reduced pressure and 3.84 g (99%) of the dextrorotatory enantiomer of methyl (3aRS,4SR,9SR,9aRS)-9-(2-benzothienyl)-4,9-ethano-2,3,3a,4,9,9a-hexahydro-1H-benzo[f]isoindole-3a-carboxylate are then obtained in the form of a white foam, used as is in the continuation of the synthesis, the characteristics of which are as follows:

mass spectrum (EI): M/Z=389 (M+)
optical rotation: $[\alpha]_{365}^{20}$=+21.5+/−0.50 (c=0.5, dichloromethane).

Stage J

The preparation is carried out as in Stage G of Example 1 but from 1.93 g (11 mmol) of 2-(2-methoxyphenyl)propenoic acid in 50 cm³ of dichloromethane comprising 1 cm³ of N,N-dimethylformamide, from 0.96 cm³ (11 mmol) of oxalyl chloride in 5 cm³ of dichloromethane, and from 3.84 g (9.9 mmol) of the dextrorotatory enantiomer of methyl (3aRS,4SR,9SR,9aRS)-9-(2-benzothienyl)-4,9-ethano-2,3,3a,4,9,9a-hexahydro-1H-benzo[f]isoindole-3a-carboxylate in 50 cm³ of dichloromethane and 3.39 cm³ (24 mmol) of triethylamine. After purification by flash chromatography on silica gel (230–400 mesh), elution being carried out with a cyclohexane/ethyl acetate (60/40 by volume) mixture, 3.26 g (60%) of the dextrorotatory enantiomer of methyl (3aRS,4SR,9SR,9aRS)-9-(2-benzothienyl)-4,9-ethano-2-[2-(2-methoxyphenyl)propenoyl]-2,3,3a,4,9,9a-hexahydro-1H-benzo[f]isoindole-3a-carboxylate are thus obtained in the form of a white foam, the characteristics of which are as follows:

mass spectrum (EI): M/Z=549 (M+)
optical rotation: $[\alpha]_{365}^{20}$=+43.2+/−0.80 (c=0.5, dichloromethane).

Stage K

The preparation is carried out as in Example 2, but from 4.49 g (8 mmol) of the dextrorotatory enantiomer of methyl (3aRS,4SR,9SR,9aRS)-9-(2-benzothienyl)-4,9-ethano-2-[2-(2 -methoxyphenyl)propenoyl]-2,3,3a,4,9,9a-hexahydro-1H-benzo[f]isoindole-3a-carboxylate at reflux for two hours in 100 cm³ of ethanol in the presence of 20 cm³ of an N aqueous sodium hydroxide solution. After two successive recrystallizations from 50% aqueous ethanol and then from a mixture of hexane and isopropanol (50/50 by volume), 2.55 g (58%) of the dextrorotatory enantiomer of (3aRS, 4SR,9SR,9aRS)-9-(2-benzothienyl)-4,9-ethano-2-[2-(2-methoxyphenyl)propenoyl]-2,3,3a,4,9,9a-hexahydro-IH-benzo[f]isoindole-3a-carboxylic acid are thus obtained in the form of white crystals, the characteristics of which are as follows:

melting point=170° C.

mass spectrum (EI): M/Z 535 (M$^+$)

$^1$H NMR spectrum (250 MHz, d6-(CD$_3$)$_2$SO, at a temperature of 373 K, d in ppm): 1.40 (mt, 1H), 1.64 (mt, 1H), 1.98 (mt, 1H), 2.13 (mt, 1H), 3.24 (mt, 3H), 3.46 (broad t, J=2.5 Hz, 1H), 3.59 (d, J=13 Hz, 1H), 3.72 (s, 3H), 4.07 (broad d, J=13 Hz, 1H), 5.54 (s, 1H), 5.68 (s, 1H), 6.40 (broad d, J=7.5 Hz, 1H), from 6.90 to 7.45 (mt, 9H), 7.52 (broad d, J=8.5 Hz, 2H).

optical rotation: $[\alpha]_{365}^{20}$=+43.5+/−1° (c=0.5, dichloromethane).

EXAMPLE 4

Preparation of the dextrorotatory enantiomer of (3aRS,4SR, 9SR,9aRS)-9-(2,4-dichlorophenyl)-4,9-ethano- 2-[2-(2-methoxyphenyl)propenoyl]-2,3,3a,4,9,9a-hexahydro-1H-benzo[f]isoindole-3a-carboxylic acid The preparation is carried out according to Stages A, B and C of Example 1, then D, E and F of Example 3 and then as described hereinbelow:

Stage A

The preparation is carried out as in Stage G of Example 3 but from 22.5 g (47.6 mmol) of the levorotatory enantiomer of methyl (3aRS,4SR,7aRS)-2-benzyl-7-iodo-4-phenyl-1,2,3,4,5,7a-hexahydroisoindole-3a-carboxylate and from 2.43 g (2.1 mmol) of tetrakis(triphenylphosphine) palladium in 400 cm$^3$ of toluene and then from 10 g (52.4 mmol) of 2,4-dichlorophenylboronic acid in 200 cm$^3$ of methanol and from 400 cm$^3$ of a 2N aqueous sodium carbonate solution, at reflux for two hours. After purification by flash chromatography on silica gel (230–400 mesh), elution being carried out with a cyclohexane/ethyl acetate (90/10 by volume) mixture, 20.3 g (87%) of the levorotatory enantiomer of methyl (3aRS,4SR,7aRS)-2-benzyl-4-phenyl-7-(2,4-dichlorophenyl)-1,2,3,4,5,7a-hexahydroisoindole-3a-carboxylate are obtained in the form of a very viscous yellow oil, the characteristics of which are as follows:

mass spectrum (EI): M/Z=492 (M$^+$)

NMR spectrum optical rotation: $[\alpha]_{365}^{20}$=−41.6+/−10 (c=0.5, methanol)

Stage B

The preparation is carried out as in Stage E of Example 1, but from 20.15 g (40.9 mmol) of the levorotatory enantiomer of methyl (3aRS,4SR,7aRS)-2-benzyl-4-phenyl-7-(2,4-dichlorophenyl)-1,2,3,4,5,7a-hexahydroisoindole-3a-carboxylate in 30 cm$^3$ of dichloromethane and 73 cm$^3$ (0.82 mol) of trifluoromethanesulfonic acid for four hours at reflux. After purification by flash chromatography on silica gel (230–400 mesh), elution being carried out with a cyclohexane/ethyl acetate (60/40 by volume) mixture, 8.8 g (44%) of the dextrorotatory enantiomer of methyl (3aRS, 4SR,9SR,9aRS)-2-benzyl-9-(2,4-dichlorophenyl)-4,9-ethano-2,3,3a,4,9,9a-hexahydro-1H-benzo[f]isoindole-3a-carboxylate are obtained in the form of a white foam, the characteristics of which are as follows:

mass spectrum (EI): M/Z=492 (M$^+$)

optical rotation: $[\alpha]_{365}^{20}$=+86.5+/−1.50 (c=0.5, dichloromethane).

Stage C

The preparation is carried out as in Stage I of Example 3, but from 8.8 g (17.9 mmol) of the dextrorotatory enantiomer of methyl (3aRS,4SR,9SR,9aRS)-2-benzyl-9-(2,4-dichlorophenyl)- 4,9-ethano-2,3,3a,4,9,9a-hexahydro-1H-benzo[f]isoindole-3a-carboxylate and from 2.9 cm$^3$ (44.8 mmol) of vinyl chloroformate in 150 cm$^3$ of dichloromethane for twenty-four hours at room temperature, and by then taking the concentrate to reflux for eight hours in 180 cm$^3$ of a 4N solution of hydrochloric acid in dioxane. 5.44 g (66%) of the dextrorotatory enantiomer of methyl (3aRS,4SR,9SR,9aRS)-9-(2,4-dichlorophenyl)-4,9-ethano-2,3,3a,4,9,9a-hexahydro-1H-benzo[f]isoindole-3a-carboxylate are obtained in the form of a pale yellow foam, used as is in the continuation of the synthesis, the characteristics of which are as follows:

mass spectrum (EI): M/Z=438 (M$^+$)

optical rotation: $[\alpha]_{365}^{20}$=+103+/−1.7° (c=0.5, dichloromethane).

Stage D

The preparation is carried out as in Stage G of Example 1, but from 2.4 g (13.5 mmol) of 2-(2-methoxyphenyl) propenoic acid and from 1.2 cm$^3$ (13.7 mmol) of oxalyl chloride in 25 cm$^3$ of dichloromethane comprising 1 cm$^3$ of N,N-dimethylformamide, and then from 5.44 g (12.3 mmol) of the dextrorotatory enantiomer of methyl (3aRS,4SR,9SR, 9aRS)-9-(2,4-dichlorophenyl)-4,9-ethano-2,3,3a,4,9,9a-hexahydro-1H-benzo[f]isoindole-3a-carboxylate in 50 cm$^3$ of dichloromethane and 4.2 cm$^3$ (30 mmol) of triethylamine for eighteen hours at room temperature. After purification by flash chromatography on silica gel (230–400 mesh), elution being carried out with a cyclohexane/ethyl acetate (60/40 by volume) mixture, 5.4 g (67%) of the dextrorotatory enantiomer of methyl (3aRS,4SR,9SR,9aRS)-9-(2,4-dichlorophenyl)-4,9-ethano-2-[2-(2-methoxyphenyl) propenoyl]-2,3,3a,4,9,9a-hexahydro-1H-benzo[f]isoindole-3a-carboxylate are obtained in the form of a white foam, the characteristics of which are as follows:

mass spectrum (EI): M/Z=562 (M$^+$)

optical rotation: $[\alpha]_{365}^{20}$=+106.3+/−1.70 (c=0.5, methanol).

Stage E

The preparation is carried out as in Example 2, but from 5.4 g (9.6 mmol) of the dextrorotatory enantiomer of methyl (3aRS,4SR,9SR,9aRS)-9-(2,4-dichlorophenyl)-4,9-ethano-2-[2-(2-methoxyphenyl)propenoyl]-2,3,3a,4,9,9a-hexahydro-1H-benzo[f]isoindole-3a-carboxylate at reflux for three and a half hours in 130 cm$^3$ of ethanol and 20 cm$^3$ of a normal aqueous sodium hydroxide solution. After purification by flash chromatography on silica gel (230–400 mesh), elution being carried out with an ethyl acetate/acetic acid (99/1 by volume) mixture, and then recrystallizing from isopropyl acetate, 1.94 g (36%) of the dextrorotatory enantiomer of (3aRS,4SR,9SR,9aRS)-9 -(2,4-dichlorophenyl)-4, 9-ethano-2-[2-(2-methoxyphenyl)propenoyl]-2,3,3a,4,9,9a-hexahydro-1H-benzo[f]isoindole-3a-carboxylic acid are obtained in the form of white crystals, the characteristics of which are as follows:

melting point=194° C.

mass spectrum (EI): M/Z=548 (M$^+$)

optical rotation: $[\alpha]_{365}^{20}$=+126.6+/−1.80 (c=0.5, methanol).

EXAMPLE 5

Preparation of the dextrorotatory enantiomer of (3aRS,4SR, 9SR,9aRS)-9-(3,4-dichlorophenyl)-4,9-ethano-2-[2-(2-methoxyphenyl)propenoyl]-2,3,3a,4,9,9a-hexahydro-1H-benzo[f]isoindole-3a-carboxylic acid The preparation is carried out according to Stages A, B and C of Example 1 and then as described hereinbelow:

Stage A

The preparation is carried out as in Stage D of Example 1, but from 9.95 g (44 mmol) of 3,4-dichlorobromobenzene in 120 cm³ of diethyl ether and from 1.07 g (44 mmol) of magnesium at reflux for 30 minutes and then from 8 g (22 mmol) of the levorotatory enantiomer of methyl (3aRS,4SR,7aRS)-2-benzyl-7-oxo-4-phenyloctahydroisoindole-3a-carboxylate in 120 cm³ of diethyl ether for ten minutes at a temperature in the region of 10° C. After purification by flash chromatography on silica gel (230–400 mesh), elution being carried out with a cyclohexane/acetate (85/15 by volume) mixture, 7.19 g (64%) of the levorotatory enantiomer of methyl (3aRS,4SR,7RS,7aRS)-2-benzyl-7-(3,4-dichlorophenyl)-7-hydroxy-4-phenyloctahydroisoindole-3a-carboxylate are obtained in the form of a white solid, the characteristic of which is as follows:

optical rotation: $[\alpha]_{365}^{20}=-28.6+/-0.70$ (c=0.5, methanol).

Stage B

The preparation is carried out as in Stage E of Example 1, but from 9 g (17 mmol) of the levorotatory enantiomer of methyl (3aRS,4SR,7RS,7aRS)-2-benzyl-7-(3,4-dichlorophenyl)-7-hydroxy-4-phenyl-1,3,3a,4,5,6-hexahydroisoindole-3a-carboxylate, from 23 cm³ of trifluoromethanesulfonic acid and from 150 cm³ of dichloromethane. 8.41 g (970-.) of the dextrorotatory enantiomer of methyl (3aRS,4SR,9SR,9aRS)-2-benzyl-9-(3,4-dichlorophenyl)-4,9-ethano-2,3,3a,4,9,9a-hexahydro-1H-benzo[f]isoindole-3a-carboxylate are obtained in the form of a white foam, the characteristic of which is as follows:

optical rotation: $[\alpha]_{365}^{20}=+43.9+/-0.30$ (c=0.5, methanol).

Stage C

The preparation is carried out as in Stage I of Example 3, but from 8.3 g (16.8 mmol) of the dextrorotatory enantiomer of methyl (3aRS,4SR,9SR,9aRS)-2-benzyl-9-(3,4-dichlorophenyl)-4,9-ethano-2,3,3a,4,9,9a-hexahydro-1H-benzo[f]isoindole-3a-carboxylate and from 3.86 cm³ (33.7 mmol) of vinyl chloroformate in 50 cm³ of dichloromethane for twenty-four hours at room temperature. By taking the concentrate to reflux for eight hours in 135 cm³ of a 1N solution of hydrochloric acid in diethyl ether, 5.47 g (750%) of the dextrorotatory enantiomer of methyl (3aRS,4SR,9SR,9aRS)-9-(2,4-dichlorophenyl)-4,9-ethano-2,3,3a,4,9,9a-hexahydro-1H-benzo[f]isoindole-3a-carboxylate are obtained in the form of a foam:

optical rotation: $[\alpha]_{365}^{20}=+67.3+/-1.20$ (c=0.5, dichloromethane)

Stage D

The preparation is carried out as in Stage G of Example 1, but from 5.4 g (12.3 mmol) of the dextrorotatory enantiomer of methyl (3aRS,4SR,9SR,9aRS)-9-(3,4-dichlorophenyl)-4,9-ethano-2,3,3a,4,9,9a-hexahydro-1H-benzo[f]isoindole-3a-carboxylate, from 2.3 g (12.9 mmol) of 2-(2-methoxyphenyl)propenoic acid, from 1.13 cm³ (12.9 mmol) of oxalyl chloride and from 3.6 cm³ (25.8 mmol) of triethylamine. After purification by flash chromatography on silica gel (230–400 mesh), elution being carried out with cyclohexane/acetate (60/40, then 50/50 by volume) mixtures, 5.45 g (79%) of the dextrorotatory enantiomer of methyl (3aRS,4SR,9SR,9aRS)-9-(3,4-dichlorophenyl)-4,9-ethano-2-[2-(2-methoxyphenyl)propenoyl]-2,3,3a,4,9,9a-hexahydro-1H-benzo[f]isoindole-3a-carboxylate are obtained in the form of a white solid, the characteristic of which is as follows:

optical rotation: $[\alpha]_{365}^{20}=+78.6+/-1.40$ (c=0.5, methanol).

Stage E

The preparation is carried out as in Example 2, but from 5.2 g (9.2 mmol) of the dextrorotatory enantiomer of methyl (3aRS,4SR,9SR,9aRS)-9-(3,4-dichlorophenyl)-4,9-ethano-2-[2-(2-methoxyphenyl)propenoyl]-2,3,3a,4,9,9a-hexahydro-1H-benzo[f]isoindole-3a-carboxylate, from 46 cm³ of a normal aqueous sodium hydroxide solution and 100 cm³ of dioxane. After recrystallization from a mixture of 150 cm³ of cyclohexane and of 20 cm³ of ethyl acetate isopropyl acetate, 4.23 g (83%) of the dextrorotatory enantiomer of (3aRS,4SR,9SR,9aRS)-9-(3,4-dichlorophenyl)-4,9-ethano-2-[2-(2-methoxyphenyl)propenoyl]-2,3,3a,4,9,9a-hexahydro-1H-benzo[f]isoindole-3a-carboxylic acid are obtained, the characteristics of which are as follows:

melting point=210° C.

optical rotation: $[\alpha]_{365}^{20}=+85.2+/-1.30$ (c=0.5, methanol).

EXAMPLE 6

Preparation of the dextrorotatory enantiomer of (3aRS,4SR,9SR,9aRS)-9-(4-bromophenyl)-4,9-ethano-2-[2-(2-methoxyphenyl)propenoyl]-2,3.3a,4,9,9a-hexahydro-1H-benzo[f]isoindole-3a-carboxylic acid The preparation is carried out according to Stages A, B and C of Example 1, then D and E of Example 3 and then as hereinbelow:

Stage A

The preparation is carried out as in Stage G of Example 3, but from 12 g (25 mmol) of the levorotatory enantiomer of methyl (3aRS,4SR,7aRS)-2-benzyl-7-iodo-4-phenyl-2,3,a,4,5,7a-hexahydroisoindole-3a-carboxylate in 240 cm³ of toluene, from 1.46 g (1.25 mmol) of tetrakis(triphenylphosphine)palladium, from 5.56 g (27 mmol) of 4-bromophenylboronic acid in 120 cm³ of methanol and from 240 cm³ of a 2N aqueous sodium carbonate solution at reflux for eighteen hours. After purification by flash chromatography on silica gel (230–400 mesh), elution being carried out with a mixture of cyclohexane and of ethyl acetate (90/10 by volume), 10.44 g (83%) of the levorotatory enantiomer of methyl (3aRS,4SR,7aRS)-2-benzyl-7-(4-bromophenyl)-4-phenyl-2,3,3a,4,5,7a-hexahydro-1H-isoindole-3a-carboxylate are obtained in the form of a white foam, the characteristics of which are as follows:

optical rotation: $[\alpha]_{365}^{20}=-10.4+/-0.70$ (c=0.5, methanol).

mass spectrum (EI): M/Z=502 (M⁺).

Stage B

The preparation is carried out as in Stage E of Example 1, but from 10.44 g (21 mmol) of the levorotatory enantiomer of methyl (3aRS,4SR,7aRS)-2-benzyl-7-(4-bromophenyl)-4-phenyl-2,3,3a,4,5,7a-hexahydro-1H-isoindole-3a-carboxylate and from 13.8 cm³ of trifluoromethanesulfonic acid in 100 cm³ of dichloromethane for 18 hours at room temperature. 9.26 g (89a) of the dextrorotatory enantiomer of methyl (3aRS,4SR,9SR,9aRS)-2-benzyl-9-(4-bromophenyl)-4,9-ethano-2,3,3a,4,9,9a-hexahydro-1H-benzo[f]isoindole-3a-carboxylate are thus obtained in the form of a beige powder, used as is in the continuation of the synthesis, the characteristics of which are as follows:

optical rotation $[\alpha]_{365}^{20}=+38.5+/-0.90$ (c=0.5, methanol).

mass spectrum (EI): M/Z=502 (M⁺).

Stage C

The preparation is carried out as in Stage I of Example 3, but from 9.26 g (18 mmol) of the dextrorotatory enantiomer of methyl (3aRS,4SR,9SR,9aRS)-2-benzyl-9-(4-bromophenyl)-4,9-ethano-2,3,3a,4,9,9a-hexahydro-1H-isoindole-3a-carboxylate and from 5.06 cm³ (55 mmol) of vinyl chloroformate for seventy-two hours at room temperature in 200 cm³ of dichloromethane, and by then taking the concentrate in 200 cm³ of methanol and 55 cm³ of a 4M solution of hydrochloric acid in dioxane to reflux for three hours. 7.32 g (80%) of hydrochloride of the dextrorotatory enantiomer of methyl (3aRS,4SR,9SR,9aRS)-9-(4-bromophenyl)-4,9-ethano-2,3,3a,4,9,9a-hexahydro-1H-isoindole-3a-carboxylate are thus obtained in the form of white crystals, the characteristics of which are as follows:

optical rotation: $[\alpha]_{365}^{20}$=+59.8+/−1.10 (c=0.5, methanol).

mass spectrum (EI): M/Z=412 (M⁺).

Stage D

The preparation is carried out as in Stage G of Example 1, but from 7.32 g (16.3 mmol) of hydrochloride of the dextrorotatory enantiomer of methyl (3aRS,4SR,9SR, 9aRS)-9-(4-bromophenyl)-4,9-ethano-2,3,3a,4,9,9a-hexahydro-1H-benzo[f]isoindole-3a-carboxylate, from 3.2 g (17.9 mmol) of 2-(2-methoxyphenyl)propenoic acid, from 1.57 cm³ (17.9 mmol) of oxalyl chloride and from 5 cm³ (35.8 mmol) of triethylamine in solution in 70 cm³ of dichloromethane comprising 0.2 cm³ of DMF for twenty hours at room temperature. After purification on silica gel (230–400 mesh), elution being carried out with a mixture of cyclohexane and ethyl acetate (70/30 by volume), 7.01 g (75%) of the dextrorotatory enantiomer of methyl (3aRS, 4SR,9SR,9aRS)-9-(4-bromophenyl)-4,9-ethano-2-[2-(2-methoxyphenyl)propenoyl]-2,3,3a,4,9,9a-hexahydro-1H-benzo[f]isoindole-3a-carboxylate are obtained in the form of a light-beige powder, the characteristics of which are as follows:

optical rotation: $[\alpha]_{365}^{20}$=+60.6+/−1.10 (c=0.5, methanol).

mass spectrum (EI): M/Z=572 (M⁺).

Stage E

The preparation is carried out as in Example 2, but from 7.01 g (12.2 mmol) of the dextrorotatory enantiomer of methyl (3aRS,4SR,9SR,9aRS)-9-(4-bromophenyl)-4,9-ethano-2-[2-(2-methoxyphenyl)propenoyl]-2,3,3a,4,9,9a-hexahydro-1H-benzo[f]isoindole-3a-carboxylate at reflux for seven hours in 15.3 cm³ of a normal aqueous sodium hydroxide solution and from 250 cm³ of ethanol. After purification by flash chromatography on silica gel (230–400 mesh), elution being carried out with a mixture of ethyl acetate, of methanol and of acetic acid (95/4/1 by volume), and then recrystallization from a mixture-of ethyl acetate and of diisopropyl ether (1/4 by volume), 2.28 g (33%) of (3aRS,4SR,9SR,9aRS)-9-(4-bromophenyl)-4,9-ethano-2-[2-(2-methoxyphenyl)propenoyl]-2,3,3a,4,9,9a-hexahydro-1H-benzo[f]isoindole-3a-carboxylic acid, dextrorotatory enantiomer, are obtained in the form of a white solid, the characteristics of which are as follows:

optical rotation: $[\alpha]_{365}^{20}$=+72.6+/−1.20 (c=0.5, methanol).

melting point=205° C.

mass spectrum (EI): M/Z=558 (M⁺).

optical rotation: $[\alpha]_{365}^{20}$=+65.4+/−1.00 (c=0.5, methanol).

EXAMPLE 7

Preparation the dextrorotatory enantiomer of (3aRS,4SR, 9SR,9aRS)-4,9-ethano-2-[2-(2-methoxyphenyl)propenoyl]-9-(4-chlorophenyl)-2,3,3a,4,9,9a-hexahydro-1H-benzo[f] isoindole-3a-carboxylic acid The preparation is carried out according to Stages A, B and C of Example 1 and then according to:

Stage A

The preparation is carried out as in Stage D of Example 1, but from 10.2 g (53 mmol) of 4-chlorobenzene, from 1.2 g (53 mmol) of magnesium turnings and from 9.67 g (26.6 mmol) of the levorotatory enantiomer of methyl (3aRS,4SR, 7aRS)-2-benzyl-7-oxo-4-phenylperhydroisoindole-3a-carboxylate in 60 cm³ of diethyl ether and 60 cm³ of toluene. After purification on silica gel (230–400 mesh), elution being carried out with a mixture of cyclohexane and of ethyl acetate (90/10 by volume), 8.5 g (68%) of the levorotatory enantiomer of methyl (3aRS,4SR,7RS,7aRS)-2-benzyl-7-(4-chlorophenyl)-7-hydroxy-4-phenyloctahydroisoindole-3a-carboxylate are obtained in the form of a white solid, the characteristic of which is as follows:

optical rotation: $[\alpha]_{365}^{20}$=−24.2+/−0.70 (c=0.5, methanol).

Stage B

The preparation is carried out as in Stage E of Example 1, but from 9.3 g (19.5 mmol) of the levorotatory enantiomer of methyl (3aRS,4SR,7RS,7aSR)-2-benzyl-7-(4-chlorophenyl)-7-hydroxy-4-phenyl-2,3,3a,4,5,6-hexahydroisoindole-3a-carboxylate, from 21.6 cm³ (0.2 mol) of trifluoromethanesulfonic acid and from 100 cm³ of dichloromethane. After purification on silica gel (230–400 mesh), elution being carried out with a mixture of cyclohexane and of ethyl acetate (90/10 by volume, 6.9 g (77%) of the dextrorotatory enantiomer of methyl (3aRS,4SR,9SR, 9aRS)-2-benzyl-9-(4-chlorophenyl)-4,9-ethano-2,3,3a,4,9, 9a-hexahydro-1H-benzo[f]isoindole-3a-carboxylate are obtained in the form of a white solid, the characteristic of which is as follows:

optical rotation: $[\alpha]_{365}^{20}$=+43.7+/−0.90 (c=0.5, methanol).

Stage C

The preparation is carried out as in Stage I of Example 3, but from 6.9 g (15 mmol) of the dextrorotatory enantiomer of methyl (3aRS,4SR,9SR,9aRS)-2-benzyl-9-(4-chlorophenyl)-4,9-ethano-2,3,3a,4,9,9a-hexahydro-1H-benzo[f]isoindole-3a-carboxylate and from 4.14 cm³ (45 mmol) of vinyl chloroformate in 100 cm³ of dichloromethane, followed by purification on silica gel (230–400 mesh), elution being carried out with a mixture of cyclohexane and of ethyl acetate (70/30 by volume), of the intermediate carbamate, which is subsequently taken up in 200 cm³ of methanol and 48 cm³ of a 4N solution of hydrochloric acid in dioxane. 5.34 g (85%) of the dextrorotatory enantiomer of methyl (3aRS,4SR,9SR,9aRS)-9-(4-chlorophenyl)-4,9-ethano-2,3,3a,4,9,9a-hexahydro-1H-benzo[f]isoindole-3a-carboxylate hydrochloride are thus obtained in the form of a white foam, the characteristic of which is as follows:

optical rotation: $[\alpha]_{365}^{20}$=+66.8+/−1.20 (c=0.5, methanol).

Stage D

The preparation is carried out as in Stage G of Example 1, but from 5.34 g (13.2 mmol) of the dextrorotatory enantiomer of methyl (3aRS,4SR,9SR,9aRS)-9-(4-chlorophenyl)-4,9-ethano-2,3,3a,4,9,9a-hexahydro-1H-benzo[f]isoindole-3a-carboxylate hydrochloride, from 2.6 g (14.5 mmol) of 2-(2-methoxyphenyl)propenoic acid, from 1.3 cm³ (14.5 mmol) of oxalyl chloride and from 4 cm³ (29 mmol) of triethylamine. After purification on silica gel (230–400 mesh), elution being carried out with a mixture of cyclohexane and of ethyl acetate (70/30 by volume), 6.48 g (936) of the dextrorotatory enantiomer of methyl (3aRS, 4SR,9SR,9aRS)-9-(4-chlorophenyl)-4,9-ethano-2-[2-(2-methoxyphenyl)propenoyl]-2,3,3a,4,9,9a-hexahydro-1H-benzo[f]isoindole-3a-carboxylate are obtained, the characteristic of which is as follows:

optical rotation: $[\alpha]_{365}^{20}$=+66.4+/−1.10 (c=0.5, methanol).

Stage E

The preparation is carried out as in Example 2, but from 6.4 g (12 mmol) of the dextrorotatory enantiomer of methyl (3aRS,4SR,9SR,9aRS)-9-(4-chlorophenyl)-4,9-ethano-2-[2-(2-methoxyphenyl)propenoyl]-2,3,3a,4,9,9a-hexahydro-1H-benzo[f]isoindole-3a-carboxylate, from 24 cm$^3$ of a normal aqueous sodium hydroxide solution and 160 cm$^3$ of ethanol. After purification by flash chromatography on silica gel (230–400 mesh), elution being carried out with a dichloromethane/ethanol (96/4 by volume) mixture, and then recrystallization from isopropyl acetate, 1.55 g (25%) of (3aRS,4SR,9SR,9aRS)-9-(4-chlorophenyl)-4,9-ethano-2-[2-(2-methoxyphenyl)propenoyl]-2,3,3a,4,9,9a-hexahydro-1H-benzo[f]isoindole-3a-carboxylic acid, dextrorotatory enantiomer, are obtained, the characteristics of which are as follows:

melting point: 210° C.

optical rotation: $[\alpha]_{365}^{20}$=+72.2+/−1.20 (c=0.5, methanol).

EXAMPLE 8

Preparation of the dextrorotatory enantiomer of methyl (3aRS,4SR,9SR,9aRS)-9-(2,3-dihydrobenzofuran-5-yl)-4,9-ethano-2-[2-(2-methoxyphenyl)propenoyl]-2,3,3a,4,9,9a-hexahydro-1H-benzo[f]isoindole-3a-carboxylate acid The preparation is carried out according to Stages A, B and C of Example 1 and then the preparation is carried out as disclosed in Examples 61 (Stages A, B and C) and 62 of Application WO 98/29390 but from the levorotatory enantiomer methyl (3aRS,4SR,7aRS)-2-benzyl-7-oxo-4-phenyloctahydroisoindole-3a-carboxylate, in order to successively form:

dextrorotatory enantiomer [lacuna] methyl (3aRS,4SR,9SR,9aRS)-2-benzyl-9-(2,3-dihydrobenzofuran-5-yl)-4,9-ethano-2,3,3a,4,9,9a-hexahydro-1H-benzo[f]isoindole-3a-carboxylate dextrorotatory enantiomer methyl (3aRS,4SR,9SR,9aRS)-9-(2,3-dihydrobenzofuran-5-yl)-4,9-ethano-2,3,3a,4,9,9a-hexahydro-1H-benzo[f]isoindole-3a-carboxylate, dextrorotatory enantiomer methyl (3aRS,4SR,9SR,9aRS-9-(2,3-dihydrobenzofuran-5-yl)-4,9-ethano-2-[2-(2-methoxyphenyl)propenoyl]-2,3,3a,4,9,9a-hexahydro-1H-benzo[f]isoindole-3a-carboxylate dextrorotatory enantiomer of (3aRS,4SR,9SR,9aRS)-9-(2,3-dihydrobenzofuran-5-yl)-4,9-ethano-2-[2-(2-methoxyphenyl)propenoyl]-2,3,3a,4,9,9a-hexahydro-1H-benzo[f]isoindole-3a-carboxylic acid in the form of a white crystalline powder, the characteristics of which are as follows:

melting point=241° C.

mass spectrum (EI): M/Z=521 (M$^+$)

optical rotation: $[\alpha]_{365}^{20}$=+75.5+/−1.30 (c=0.5, DMF).

EXAMPLE 9

Preparation of the dextrorotatory enantiomer of (3aRS,4SR,8SR,8aRS)-4,8-ethano-2-[2-(2-methoxyphenyl)propenoyl]-8-(4-methylphenyl)-2,3,3a,4,8,8a-hexahydro-1H-thieno[2,3-f]isoindole-3a-carboxylic acid Stage A A solution of 45.77 g (0.4 mol) of thiophene-3-carboxaldehyde and 33.43 g (0.28 mol) of N-acetylglycine in 75 cm$^3$ of acetic anhydride comprising 16.8 g (0.28 mol) of dry sodium acetate is heated at 100° C. for one hour under the conditions described by Org. Synth., II, 1–3 and then the reaction mixture is allowed to cool the night to a temperature in the region of 0° C. The crystals formed are filtered off and 42.8 g of beige crystals are then obtained, which crystals are brought to reflux for four hours in 150 cm$^3$ of water and 400 cm$^3$ of-acetone. After cooling, the solvents are evaporated under reduced pressure and the residue is purified by recrystallization from 350 cm$^3$ of water. 33.79 g (39%) of 1-acetylamino-3-(3-thienyl)propen-2-oic acid are thus obtained in the form of fine yellow crystals, the characteristic of which is as follows:

melting point=228° C.

Stage B 33.78 g (89 mmol) of 1-acetylamino-3-(3-thienyl)propen-2-oic acid are heated at reflux for four hours in 360 cm$^3$ of a normal aqueous hydrochloric acid solution under the conditions described in Org. Synth., II, 519–20. After heating for three hours, crystals are formed and are filtered off after cooling to 0° C. 22.4 g (99%) of (3-thienyl)pyruvic acid are thus obtained in the form of fine white crystals, the characteristics of which are as follows:

melting point=203–4° C.

mass spectrum (EI): M/Z=170 (M$^+$).

Stage C 17.1 cm$^3$ (21 mmol) of methyl vinyl ketone and 7.2 g (18 mmol) of sodium hydroxide pellets are successively added to a solution, cooled to 0° C., of 22.4 g (13 mmol) of (3-thienyl)pyruvic acid in 150 cm$^3$ of methanol and then the reaction mixture is stirred at a temperature in the region of 20° C. for two hours. After neutralizing with 60 cm$^3$ of a 3N aqueous hydrochloric acid solution, the precipitate formed is filtered off, washed with water and then dried at 20° C. 21.85 g (70%) of 6-(3-thienyl)-3-oxocyclohexan-1-ol-1-carboxylic acid are thus obtained in the form of a yellow powder, the characteristics of which are as follows:

melting point=204° C.

$^1$H N.M.R. spectrum (300 MHz, d6-(CD$_3$)$_2$SO with addition of a few drops of d4—CD$_3$COOD, d in ppm): from 2.20 to 2.80 (mt, 4H, CH$_2$CH$_2$), 2.34 and 3.00 (2 d, J=14 Hz, each 1H, COCH$_2$), 3.66 (dd, J=12.5 and 3 Hz, 1H, ArCH), 7.06 (d, J=5 Hz, 1H, H at 4 of the thienyl), 7.24 (broad d, J=3 Hz, 1H, H at 2 of the thienyl), 7.36 (dd, J=5 and 3 Hz, 1H, H at 5 of the thienyl).

Stage D 21.84 g (9.1 mmol) of 6-(3-thienyl)-3-oxocyclohexan-1-ol-1-carboxylic acid are heated at reflux for three hours in 220 cm$^3$ of toluene in the presence of 2.2 g of para-toluenesulfonic acid. The reaction mixture is subsequently cooled to 50 and the precipitate formed is filtered off, washed with isopropyl ether and then dried at 50° C. 18.47 g (91%) of a mixture predominantly comprising (RS)-6-(3-thienyl)-3-oxocyclohexene-1-carboxylic acid are thus obtained in the form of a brown solid, used as is in the following stage, the characteristics of which are as follows:

mass spectrum (EI): M/Z=222 (M$^+$)

Stage E 7.5 cm$^3$ (12 mmol) of methyl iodide and 16.8 cm$^3$ (11.2 mol) of 1,8-diazabicyclo[5.4.0]undec-7-ene, dropwise, are successively added to a solution of 18.45 g (8.3 mmol) of (RS)-6-(3-thienyl)-3-oxocyclohexene-1-carboxylic acid in 250 cm$^3$ of dry acetone and then the reaction mixture is brought to reflux for two hours and 30 minutes. After hot filtration of an insoluble material and concentration of the solvents under reduced pressure, the residue is purified by flash chromatography on silica gel (230–400 mesh), elution being carried out with dichloromethane. 14.84 g (76%) of methyl (RS)-6-(2-thienyl)-3 -oxocyclohexene-1-carboxylate are thus obtained in the form of a yellow powder, the characteristics of which are as follows:

melting point=69° C.

mass spectrum (EI): M/Z=236 (M$^+$)

$^1$H N.M.R. spectrum (250 MHz, CDCl$_3$, d in ppm): from 2.05 to 2.55 (mt, 4H, CH$_2$CH$_2$), 3.77 (s, 3H, COOCH$_3$), 4.33

(mt, 1H, ArCH), 6.85 (s, 1H, =CH), 6.91 (dd, J=2.5 and 2 Hz, 1H, H at 2 of the thienyl), 6.99 (dd, J=5 and 2 Hz, 1H, H at 4 of the thienyl), 7.34 (dd, J=5 and 2.5 Hz, 1H, H at 5 of the thienyl).

Stage F

The preparation is carried out according to Stage B of Example 1, but from methyl (RS)-6-(3-thienyl)-3-oxocyclohexene-1-carboxylate, to result in methyl (RS)-6-(3-thienyl)-3-oxocyclohexene-1-carboxylate in the levorotatory form.

The preparation is subsequently carried out as in Examples 1 (Stage F) and 2 (Stages A to G) of Application FR 2,772,764, but from methyl (RS)-6-(3-thienyl)-3-oxocyclohexene-1-carboxylate in the levorotatory form, in order to successively form: methyl (3aRS,4SR,7aRS)-2-benzyl-4-(3-thienyl)-7-oxooctahydroisoindole-3a-carboxylate, in the levorotatory form methyl (3aRS,4SR,7aRS)-2-benzyl-7-hydrazono-4-(3-thienyl)octahydroisoindole-3a-carboxylate, in the levorotatory form methyl (3aRS,4SR,7aRS)-2-benzyl-7-iodo-4-(3-thienyl)-1,2,3,4,5,7a-hexahydroisoindole-3a-carboxylate, in the levorotatory form methyl (3aRS,4SR,7aRS)-2-benzyl-7-(4-methylphenyl)-4-(3-thienyl)-1,2,3,4,5,7a-hexahydroisoindole-3a-carboxylate, in the levorotatory form methyl (3aRS,4SR,8SR,8aRS)-2-benzyl-4,8-ethano-8-(4-methylphenyl)-2,3,3a,4,8,8a-hexahydro-1H-thieno[2,3-f]isoindole-3a-carboxylate, in the dextrorotatory form methyl (3aRS,4SR,8SR,8aRS)-4,8-ethano-8-(4-methylphenyl)-2,3,3a,4,8,8a-hexahydro-1H-thieno[2,3-f]isoindole-3a-carboxylate, in the dextrorotatory form methyl (3aRS,4SR,8SR,8aRS)-4,8-ethano-2-[2-(2-methoxyphenyl)propenoyl]-8-(4-methylphenyl)-2,3,3a,4,8,8a-hexahydro-1H-thieno[2,3-f]isoindole-3a-carboxylate, in the dextrorotatory form (3aRS,4SR,8SR,8aRS)-4,8-ethano-2-[2-(2-methoxyphenyl)propenoyl]-8-(4-methylphenyl)-2,3,3a,4,8,8a-hexahydro-1H-thieno[2,3-f]isoindole-3a-carboxylic acid, in the dextrorotatory form, in the form of a very pale yellow powder, the characteristics of which are as follows:

melting point=176° C.

optical rotation: $[\alpha]_{365}^{20}$=101.6+/−1.40 (c=0.5, methanol)

$^1$H N.M.R. spectrum (400 MHz, d6-(CD$_3$)$_2$SO, at a temperature of 393 K, d in ppm): 1.34, 1.53 and from 1.95 to 2.10 (3 mts, respectively 1H, 1H and 2H, CH$_2$CH$_2$), 2.38 (s, 3H, ArCH$_3$), from 3.20 to 3.50 (mt, 3H, CH$_2$ at 1 and CH at 8a), 3.53 and 4.01 (respectively d and broad d, J=12.5 Hz, each 1H, CH$_2$ at 3), 3.65 (broad s, 1H, CH at 4), 3.73 (s, 3H, ArOCH$_3$) 5.54 and 5.68 (2 broad s, each 1H, =CH$_2$), from 6.90 to 7.40 (mt, 1OH, aromatic H at the ortho and meta positions of the 4-methylphenyl, aromatic H of the 2-methoxyphenyl, H at 5 and H at 6).

EXAMPLE 10

The compounds corresponding to Examples 1 to 101 of Application WO 98/29390 and to Examples 1 to 6 of Application FR 2,772,764 can be prepared respectively from the intermediate obtained in Stage B of Example 1 and in Stage F of Example 9 of the present application, the preparation being carried out by application of the procedures given as examples in the corresponding Applications WO 98/29390 and FR 2,772,764.

EXAMPLE 11

Stage B of Example 1 was carried out starting with methyl (R,S)-3-oxo-6-phenylcyclohex-1-enecarboxylate in the racemic form with various enzymes; the results obtained were as follows:

Separation of the dextrorotatory enantiomer of methyl (R,S)-3-oxo-6-phenylcyclohex-1-enecarboxylate:

| Enzyme (distributor) | ee (%) | Yield (%) |
|---|---|---|
| Pronase (Boehr. Mann.) | 91 | 82 |
|  | 100 | 41 |
| Subtilisin (Novo) | 100 | 40 |
| Alacalase 2.4 L (Novo) | 100 | 38 |
|  | 92 | 40 |
| Protease Nagarse (Sigma) | 100 | 32 |
| EH 16 (Altus Biol.) | 97 | 29 |
| EH 15 (Altus Biol.) | 91 | low |
| EH 11 (Altus Biol.) | 45 | 39 |
| Lipase M (Amano) | 74 | 54 |

Separation of the levorotatory enantiomer of methyl (R,S)-3-oxo-6-phenylcyclohex-1-enecarboxylate:

| Enzyme | ee (%) | Yield (%) |
|---|---|---|
| Lipase L2 (Boehr. Mann.) | 95 | 30 |
| Lipase PS C (Amano) | 36 | 55 |
| ESL 01 (Rec. Biocatalyst) | 79 | 29 |
| SP 525 (Novo) | 100 | low |
| Lipase L6 (Boehr. Mann.) | 50 | 22 |
| Esterase 30000 (Gist Broc) | 25 | 37 | ee: enantiomeric excess

What is claimed is:

1. A process for the preparation of a compound of formula (I), in the form of its optical isomer, or a salt of a compound of formula (I):

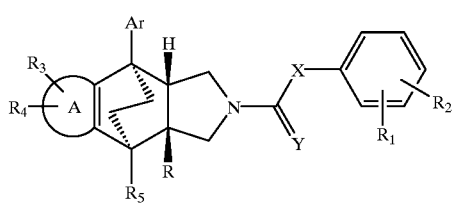

(I)

in which:

A is
a phenyl radical fused with the isoindole nucleus, wherein R$_3$ and R$_4$, which are identical or different, are chosen from hydrogen and halogen atoms and alkyl, hydroxyl, alkyloxy, alkylcarbonyloxy, mercapto, alkylthio, alkylsulfonyl, alkylsulfinyl, amino, alkylamino, dialkylamino, alkyloxycarbonylamino, carboxyl, alkyloxycarbonyl, carbamoyl, alkylcarbamoyl, dialkylcarbamoyl, formyl, alkylcarbonyl, cyano and trifluoromethyl radicals;

or A is a monocyclic or condensed bi- or tricyclic system in which each saturated or unsaturated ring comprises from 4 to 7 members and in which at least one of the rings has from 1 to 4 identical or different heteroatoms chosen from nitrogen, oxygen and sulfur atoms, wherein R$_3$ and R$_4$ are each a hydrogen atom;

Ar is
a phenyl radical optionally substituted by one or more atoms or radicals, which are identical or different, chosen from halogen atoms and the radicals: alkyl having 1 to 4 carbon atoms, alkenyl having 2 to 4 carbon atoms, hydroxyl, mercapto, alkylthio, alkylsulfonyl, alkyl-sulfinyl, amino, alkylamino, dialkylamino, formyl, alkylcarbonyl, carboxyl, alkoxycarbonyl, carbamoyl, alkylcarbamoyl, dialkylcarbamoyl, cyano, trifluoromethyl, and alkoxy having 1 to 4 carbon atoms, wherein the alkyl portion of said radicals is optionally perhalogenated, or
a phenyl radical condensed with a 4- to 7-membered heterocycle having one or more heteroatoms chosen from oxygen, nitrogen and sulfur atoms, or
a polycyclic aromatic or nonaromatic radical, or
a 5- to 12-membered heterocyclic aromatic or nonaromatic radical incorporating one or more heteroatoms chosen from oxygen, nitrogen and sulfur atoms, bonded to the condensed ring via a carbon—carbon bond, said radical being optionally substituted by one or more atoms or radicals, which are identical or different, chosen from halogen atoms and the radicals: alkyl, alkenyl having 2 to 4 carbon atoms, hydroxyl, alkoxy comprising 1 to 4 carbon atoms, mercapto, alkylthio, alkylsulfonyl, alkylsulfinyl, amino, alkylamino, dialkylamino, formyl, alkylcarbonyl, carboxyl, alkoxycarbonyl, carbamoyl, alkylcarbamoyl, dialkylcarbamoyl, cyano and trifluoromethyl, wherein an alkyl radical having 1 to 4 carbon atoms is optionally attached to any radical provided in the definition of Ar;

R is
a radical of formula

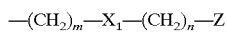

in which
$X_1$ is a single bond or an oxygen or sulfur atom,
m is an integer equal to 0 or 1,
n is an integer equal to 0, 1 or 2,
wherein one or more methylene radicals are optionally substituted by a carboxyl, alkoxycarbonyl, carbamoyl, alkylcarbamoyl, dialkylcarbamoyl, amino, alkylamino or dialkylamino radical, and
wherein an alkyl radical having 1 to 4 carbon atoms is optionally attached to any radical provided in the definition of R;

Z is
(1) a carboxyl radical,
(2) a $COOR_6$ radical, wherein $R_6$ is a straight or branched alkyl radical having 1 to 3 carbon atoms, or
(3) a radical of formula $CON(R_7)(R_8)$, wherein
$R_7$ is a hydrogen atom or a straight or branched alkyl radical having 1 to 6 carbon atoms, and
$R_8$ is
a hydrogen atom,
a hydroxyl radical, or
an arylsulfonyl radical, optionally substituted by one or more atoms or radicals, which are identical or different, chosen from halogen atoms and alkyl and alkyloxy radicals,
wherein an alkyl radical having 1 to 4 carbon atoms is optionally attached to any radical provided in the definition of Z,
(4) a 5- to 7-membered heterocycle incorporating one or more heteroatoms chosen from nitrogen, oxygen and sulfur atoms, wherein said heterocycle is optionally bonded via a heteroatom,
(5) an amino radical optionally substituted by one or two radicals, which are identical or different, chosen from the radicals:
alkyl having 1 to 4 carbon atoms,
aryl, optionally substituted by one or more radicals, which are identical or different, chosen from alkyl and alkyloxy radicals wherein an alkyl radical having 1 to 4 carbon atoms is optionally attached to any radical provided in the definition of said aryl,
5- to 7-membered heterocycle having one or more heteroatoms chosen from nitrogen, oxygen and sulfur atoms,
arylcarbonyl, optionally substituted by one or more radicals, which are identical or different, chosen from alkyl and alkyloxy radicals, wherein an alkyl radical having 1 to 4 carbon atoms is optionally attached to any radical provided in the definition of said arylcarbonyl,
(6) an alkyloxy radical having 1 to 6 straight- or branched-chain carbon atoms optionally substituted by a phenyl radical,
(7) a straight or branched alkyl radical having 1 to 6 carbon atoms, optionally substituted by an amino, alkylamino, dialkylamino, hydroxyl, alkoxy comprising 1 to 4 carbon atoms, mercapto, alkylthio, alkyloxycarbonyl, carboxyl, or cyano radical, an optionally substituted mono- or polycyclic aromatic radical having from 5 to 12 ring members which does or does not incorporate one or more heteroatoms chosen from oxygen, nitrogen and sulfur atoms, or a phenyl radical optionally substituted by one or more halogen atoms, or by one or more hydroxyl, amino or trifluoromethyl groups, or by one or more alkyl or alkenyl, alkoxy, alkylthio, alkylamino, alkylcarbonyl, $C_2$–$C_4$ alkoxycarbonyl, carbamoyl, alkylcarbamoyl, or dialkylcarbamoyl, wherein the alkyl part has 1 to 8 carbon atoms, or a formyl radical, or a 1- or 2-naphthyl radical,
or Z is
(8) a $PO(OR_9)_2$ radical in which $R_9$ is a hydrogen atom or a straight or branched alkyl radical having 1 to 6 carbon atoms, or
(9) an —NH—CO—T radical in which T is a hydrogen atom or a straight or branched alkyl radical having 1 to 6 carbon atoms optionally substituted by an amino, carboxyl, alkyloxycarbonyl, hydroxyl, alkyloxy, mercapto or alkylthio radical, or
(10)

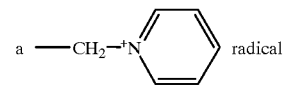

having an anion as a counterion,
wherein an alkyl radical having 1 to 4 carbon atoms is optionally attached to any radical provided in the definition of Z;
$R_1$ and $R_2$, which are identical or different, are chosen from hydrogen atoms, halogen atoms and alkyl radicals, alkyloxy radicals, each optionally substituted by a dialkylamino radical, wherein the alkyl part of each radical haes 1 to 4 carbon atoms or forms, with the nitrogen atom, a saturated heterocycle containing 5 or 6 ring members, alkylthio radicals and alkyloxycarbonyl radicals, or $R_1$ and $R_2$ are situated at the ortho position with respect to one another and form a saturated or unsaturated heterocycle having 1 or 2 heteroatoms chosen from nitrogen and oxygen, optionally substituted by a halogen atom or by an alkyl or alkyloxy radical, wherein an alkyl radical having 1 to 4 carbon atoms is optionally attached to any radical provided in the definition of $R_1$ and $R_2$;

$R_5$ is a hydrogen atom or an alkyl or alkylthio radical, wherein an alkyl radical having 1 to 4 carbon atoms is optionally attached to any radical provided in the definition of $R_5$;

X is an oxygen or sulfur atom or one of the groups: —NH—, —CO—, methylene, alken-1,1-diyl, or cycloalkan-1,1-diyl having 3 to 6 carbon atoms;

and

Y is chosen from an oxygen and sulfur atom;

said process comprising starting with a compound of formula (X):

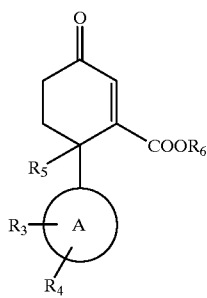

(X)

wherein A, $R_3$, $R_4$, $R_5$ and $R_6$ are defined as above for formula (1); reacting said compound of formula (X) with an enzyme to form a compound of formula (X'), in the form of an optical isomer:

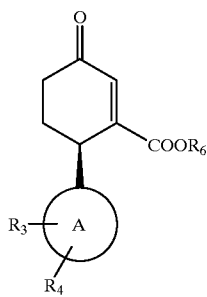

(X')

wherein A, $R_3$, $R_4$ and $R_6$ are defined as above for formula (1);

reacting said compound of formula (X') in the form of an optical isomer with an N-trialkylsilylmethyl-N-(alkoxymethyl)amine carrying a protective group for the amine functional group, to form a compound of formula (IX):

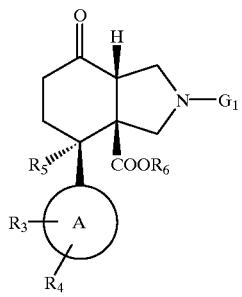

(IX)

wherein A, $R_3$, $R_4$, $R_5$ and $R_6$ are defined as above for formula (1) and $G_1$ is a protective group for the amine functional group;

converting said compound of formula (IX) to a compound of formula (I), either wherein said conversion occurs by cyclizing the cycloperhydroisoindole nucleus, to form a compound of formula (III)

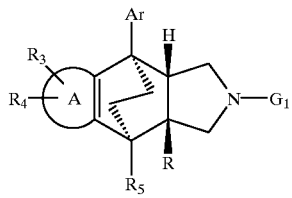

(III)

in the form of an optical isomer, wherein

A, Ar, R, $R_3$, $R_4$ and $R_5$ are defined as above for formula (1), and $G_1$ is a hydrogen atom, and by coupling with the side chain and optionally modifying the R substituent, to form a compound of formula (I); or wherein said conversion occurs by coupling of the side chain, to form a compound of formula (XII):

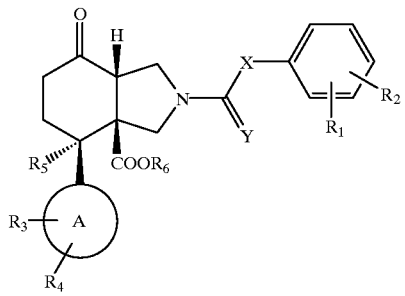

(XIII)

in the form of an optical isomer, wherein A, R., $R_2$, $R_3$, $R_4$, $R_5$, $R_6$, X and Y are defined as above, and cyclizing the cycloperhydroisoindole nucleus and optionally modifying the R substituent, to form a compound of formula (I) in the form of an optical isomer.

2. A process for the preparation of a compound of formula (I) according to claim 1, wherein, in the formula (I):

A is a phenyl radical fused to the isoindole ring or a thienyl or indolyl radical, and R₃ and R₄ are each a hydrogen atom;

Ar is a 2,3-dihydro-1,4-benzodioxin-6-yl, a 2,3-dihydrobenzofuran-5-yl or a benzothien-2-yl radical or a phenyl radical optionally substituted at the 4 position or at least one of the 2 and 4 positions by a chlorine atom;

R is a carboxyl radical, a —COOMe radical or a —CON(R₇)(R₈) radical, with the proviso that when R₇ represents a hydrogen atom, R₈ represents a methyl radical substituted by the 3-pyridyl radical, or one of R₁ or R₂ is a hydrogen atom and the other is a methoxy radical;

R₅ is a hydrogen atom or a methyl radical;

X is a methylene or vinyldiyl group; and

Y is an oxygen atom;

wherein said compound of formula (I) is in the form of an optical isomer or a salt thereof.

3. A process for the preparation of a compound of formula (I) according to claim 1, wherein said compound of formula (I) is chosen from:

methyl (3aRS,4SR,9SR,9aRS)-4,9-ethano-2-(2-(2-methoxy-phenyl)propenoyl)-9-(4-methylphenyl)-2,3,3a,4,9,9a-hexahydro-1H-benzo(f)isoindole-3a-carboxylate;

(3aRS,4SR,9SR,9aRS)-4,9-ethano-2-(2-(2-methoxyphenyl)-propenoyl)-9-(4-methylphenyl)-2,3,3a,4,9,9a-hexahydro-1H-benzo(f)isoindole-3a-carboxylic acid; (3aRS,4SR,9SR,9aRS)-4,9-ethano-2-(2-(2-methoxyphenyl)-acetyl)-9-(4-methylphenyl)-2,3,3a,4,9,9a-hexahydro-1H-benzo(f)isoindole-3a-carboxylic acid;

(3aRS,4SR,9SR,9aRS)-4,9-ethano-9-(4-methoxyphenyl)-2-(2-(2-methoxyphenyl)acetyl)-2,3,3a,4,9,9a-hexahydro-1H-benzo(f)isoindole-3a-carboxylic acid;

(3aRS,4SR,9SR,9aRS)-4,9-ethano-2-(2-(2-methoxyphenyl)-acetyl)-9-(4-methylsulfanylphenyl)-2,3,3a,4,9,9a-hexahydro-1H-benzo(f)isoindole-3a-carboxylic acid;

(3aRS,4SR, 9SR, 9aRS)-4, 9-ethano-9-(4-fluorophenyl)-2-(2-(2-methoxyphenyl)acetyl)-2,3,3a,4,9,9a-hexahydro-1H-benzo(f)isoindole-3a-carboxylic acid;

(3aRS,4SR,9SR,9aRS)4,9-ethano-2-(2-(2-methoxyphenyl)-acetyl)-9-(3-methylphenyl)-2,3,3a,4,9,9a-hexahydro-1H-benzo(f)isoindole-3a-carboxylic acid; (3aRS,4SR,9SR, 9aRS)4,9-ethano-9-(3-methoxyphenyl)-2-(2-(2-methoxyphenyl)acetyl)-2, 3, 3a,4,9, 9a-hexahydro-1H-benzo(f)isoindole-3a-carboxylic acid;

methyl (3aRS,4SR,9SR,9aRS)-9-(3,4-dimethylphenyl)-4,9-ethano-2-(2-(2-methoxyphenyl)acetyl)-2,3,3a,4,9,9a-hexahydro-1H-benzo(f)isoindole-3a-carboxylate;

(3aRS,4SR,9SR,9aRS)-9-(3,4-dimethylphenyl)-4,9-ethano-2-(2-(2-methoxyphenyl)acetyl)-2,3,3a,4,9,9a-hexahydro-1H-benzo(f)isoindole-3a-carboxylic acid;

(3aRS,4SR,9SR,9aRS)-3a-N-benzylcarbamoyl-4,9-ethano-2-(2-(2-methoxyphenyl)propenoyl)-9-(4-methylphenyl)2,3,3a,4,9,9a-hexahydro-1H-benzo(f)isoindole;

(3aRS,4SR,9SR,9aRS)-3a-carbamoyl-4,9-ethano-2-(2-(2-methoxyphenyl)propenoyl)-9-(4-methylphenyl)2,3,3a,4,9,9a-hexahydro-1H-benzo(f)isoindole;

benzyl (3aRS,4SR, 9SR,9aRS)-4,9-ethano-2-(2-(2-methoxy-phenyl)propenoyl)-9-(4-methylphenyl)-2, 3, 3a,4,9,9a-hexahydro-1H-benzo(f)isoindole-3a-hydroxamate;

(3aRS,4SR,9SR,9aRS)-4,9-ethano-2-(2-(2-methoxyphenyl)-propenoyl)-9-(4-methylphenyl)-2,3,3a,4,9,9a-hexahydro-1H-benzo(fisoindole-3a-hydroxamic acid; (3aRS,4SR, 9SR,9aRS)-4, 9-ethano-2-(2-(2-methoxyphenyl)propenoyl)-9-(4-methylphenyl)-2,3,3a,4,9,9a-hexahydro-1H-benzo(f)isoindole-3a-N-(3-pyridylmethyl)-carboxamide;

(3aRS,4SR,9SR,9aRS)-4,9-ethano-2-(2-(2-methoxyphenyl)propenoyl)-9-(4-methylphenyl)-2,3,3a,4,9,9a-hexahydro-1H-benzo(fisoindole-3a-N-(4-pyridylmethyl)-carboxamide;

methyl (3aRS,4SR, 9SR,9aRS)-4, 9-ethano-2-(2-(2-methoxyphenyl)propenoyl)-9-(4-methylphenyl)-2,3,3a,4,9,9a-hexahydro-1H-benzo(f)isoindole-3a-hydroxamate;

(3aRS,4SR,9SR,9aRS)-4,9-ethano-2-(2-(2-methoxyphenyl)propenoyl)-9-(4-methylphenyl)-2,3,3a,4,9,9a-hexahydro-I H-benzo(f)isoindole-3a-N',N'-dimethylcarbohydrazide;

(3aRS,4SR,9SR,9aRS)-4,9-ethano-2-(2-(2-methoxyphenyl)propenoyl)-9-(4-methylphenyl)-2,3,3a,4,9,9a-hexahydro-1H-benzo(f)isoindole-3a-N'-phenylcarbohydrazide;

(3aRS,4SR,9SR,9aRS)-4,9-ethano-2-(2-(2-methoxyphenyl)propenoyl)-9-(4-methylphenyl)-2,3,3a,4,9,9a-hexahydro-1H-benzo(fisoindole-3a-N',N'-pentamethylenecarbohydrazide;

(3aRS,4SR,9SR,9aRS)-4,9-ethano-2-(2-(methoxyphenyl)propenoyl)-9-(4-methylphenyl)-3a-phenylsulfonylaminocarbonyl-2,3,3a,4,9,9a-hexahydro-1H-benzo(f)isoindole;

(3aRS,4SR,9SR,9aRS)4,9-ethano-2-(2-(2-methoxyphenyl)propenoyl)-9-(4-methylphenyl)-2,3,3a,4,9,9a-hexahydro-1H-benzo(f)isoindole-3a-N-(N-oxo-3pyridyl)-methylcarboxamide;

(3aRS,4SR,9SR,9aRS)-4,9-ethano-2-(2-(2-methoxyphenyl)propenoyl)-9-(4-methylphenyl)-2,3,3a,4, 9, 9a-hexahydro-1H-benzo(f)isoindole-3a-N'-(4-methoxyphenyl)-carbohydrazide;

(3aRS,4SR,9SR, 9aRS)-4,9-ethano-2-(2-(2-methoxyphenyl)propenoyl)-9-(4-methylphenyl)-2,3,3a,4,9,9a-hexahydro-1H-benzo(f)isoindole-3a-N'-methyl,N'-phenylcarbohydrazide;

(3aRS,4SR,9SR, 9aRS)-4, 9-ethano-2-(2-(2-methoxyphenyl)propenoyl)-9-(4-methylphenyl)-2,3,3a,4,9,9a-hexahydro-1H-benzo(f)isoindole-3a-N'-(2-methyl-phenyl) carbohydrazide;

methyl (3aRS,4SR,9SR,9aRS)-9-(2,3-dihydro-1,4-benzodioxin-6-yl)-4,9-ethano-2-(2-(2-methoxyphenyl)-propenoyl)-2,3,3a,4,9,9a-hexahydro-1H-benzo(fisoindole-3a-carboxylate;

(3aRS,4SR,9SR,9aRS)-9-(2,3-dihydro-1,4-benzodioxin-6-yl)-4,9-ethano-2-(2-(2-methoxyphenyl)propenoyl)-2,3,3a,4,9,9a-hexahydro-1H-benzo(f)isoindole-3a-carboxylic acid;

(3aRS,4SR,9SR,9aRS)-9-(2,3-dihydro-1,4-benzodioxin-6-yl)-4,9-ethano-2-(2-(2-methoxyphenyl)propenoyl))-2,3,3a,4,9,9a-hexahydro-1H-benzo(f)isoindole-3a-(N-(3-pyridylmethyl)carboxamide;

(3aRS,4SR,9SR,9aRS)-9-(2,3-dihydro-1,4-benzodioxin-6-yl)-4,9-ethano-2-(2-(2-methoxyphenyl)propenoyl))-2,3,3a,4,9,9a-hexahydro-1H-benzo(f)isoindole-3a-N-(2-thienylmethyl)carboxamide;

(3aRS,4SR, 9SR, 9aRS)-4, 9-ethano-2-(2-(2-methoxyphenyl)-acetyl)-9-(3,4, 5-trimethylphenyl)-2,3, 3a,4,9,9a-hexahydro-1H-benzo(f)isoindole-3a-carboxylic acid;

(3aRS,4SR, 9SR,9aRS)-4, 9-ethano-2-(2-(2-methoxyphenyl)-propenoyl)-9-(2-methylphenyl)-2,3, 3a,4,9,9a-hexahydro-1H-benzo(fisoindole-3a-carboxylic acid; methyl (3aRS,4SR,9SR,9aRS)-4,9-ethano-2-(2-(2-methoxyphenyl)propenoyl)-9-(4-trifluoromethylphenyl)-2,3,3a,4,9,9a-hexahydro-1H-benzo(fisoindole-3a-carboxylate;

(3aRS,4SR,9SR,9aRS)-4,9-ethano-2-(2-(2-methoxyphenyl)-propenoyl)-9-(4-trifluoromethylphenyl)-2,3,3a,4,9,9a-hexahydro-1H-benzo(f)isoindole-3a-carboxylic acid; (3aRS,4SR,9SR, 9aRS)-4,9-ethano-2-(2-(2-methoxyphenyl)-propenoyl)-9-(4-trifluoromethylphenyl)-2,3,3a,4,9,9a-hexahydro-1H-benzo(fisoindole-3a-N-(4-pyridylmethyl)carboxamide;

(3aRS,4SR,9SR,9aRS)4,9-ethano-2-(2-(2-methoxyphenyl)-propenoyl)-9-(4-trifluoromethylphenyl)-2, 3, 3a,4,9,9a-hexahydro-1H-benzo(fisoindole-3a-N'-benzoylcarbohydrazide;

(3aRS,4SR,9SR,9aRS)-4,9-ethano-2-(2-(2-methoxyphenyl)-propenoyl)-9-(4-trifluoromethylphenyl)-2,3,3a,4,9,9a-hexahydro-1H-benzo(fisoindole-3a-N'-phenylcarbohydrazide;

methyl (3aRS,4SR,9SR,9aRS)-4,9-ethano-2-(2-(2-methoxyphenyl)propenoyl)-9-(2-naphthyl)-2,3,3a,4,9,9a-hexahydro-1H-benzo(fisoindole-3a-carboxylate; (3aRS,4SR,9SR,9aRS)4,9-ethano-2-(2-(2-methoxyphenyl)-propenoyl)-9-(2-naphthyl)-2,3,3a,4,9,9a-hexahydro-1H-benzo(Disoindole-3a-carboxylic acid;

methyl (3aRS,4SR, 9SR, 9aRS)-4,9-ethano-2-(2-(2-methoxyphenyl)propenoyl)-9-(5-methyl-2-thienyl)-2,3,3a,4,9,9a-hexahydro-1H-benzo(f)isoindole-3a-carboxylate;

(3aRS,4SR,9SR,9aRS)-4,9-ethano-2-(2-(2-methoxyphenyl)-propenoyl)-9-(5-methyl-2-thienyl)-2,3,3a,4,9,9a-hexahydro-1H-benzo(f)isoindole-3a-carboxylic acid;

methyl (3aRS,4SR,9SR,9aRS)-9-(4-bromophenyl)-4,9-ethano-2-(2-(2-methoxyphenyl)propenoyl)-2,3,3a,4,9,9a-hexahydro-1H-benzo(f)isoindole-3a-carboxylate;

(3aRS,4SR,9SR,9aRS)-9-(4-bromophenyl)-4,9-ethano-2-(2-(2-methoxyphenyl)propenoyl)-2,3,3a,4,9,9a-hexahydro-1H-benzo(f)isoindole-3a-carboxylic acid;

(3aRS,4SR,9SR,9aRS)-9-(3,4-dichlorophenyl)-4,9-ethano-2-(2-(2-methoxyphenyl)propenoyl)-2,3,3a,4,9,9a-hexahydro-1H-benzo(f)isoindole-3a-carboxylic acid;

methyl (3aRS,4SR,9SR,9aRS)-4,9-ethano-2-(2-(2-methoxyphenyl)propenoyl)-9-(4-chlorophenyl)-2,3,3a,4,9,9a-hexahydro-1H-benzo(f)isoindole-3a-carboxylate;

(3aRS,4SR,9SR,9aRS)-9-(4-chlorophenyl)4, 9-ethano-2-(2-(2-methoxyphenyl)propenoyl)-2, 3, 3a,4,9,9a-hexahydro-1H-benzo(Disoindole-3a-carboxylic acid;

(3aRS,4SR,9SR,9aRS)-4,9-ethano-2-(2-(2-methoxyphenyl)propenoyl)-9-(4-methoxy-3-methylphenyl)-2,3,3a,4,9,9a-hexahydro-1H-benzo(f)isoindole-3a-carboxylic acid;

methyl (3aRS,4SR,9SR,9aRS)-4, 9-ethano-2-(2-(2-methoxyphenyl)propenoyl)-9-(3-indolyl)-2,3, 3a,4,9, 9a-hexahydro-1H-benzo(f)isoindole-3a-carboxylate;

(3aRS,4SR,9SR,9aRS)-4,9-ethano-9-(4-isopropylphenyl)-2-(2-(2-methoxyphenyl)-acetyl)-2,3, 3a,4,9,9a-hexahydro-1H-benzo(f)isoindole-3a-carboxylic acid; (3aRS,4SR, 9SR,9aRS)-4,9-ethano-9-(4-isopropylphenyl)-2-(2-(2-methoxyphenyl)propenoyl)-2, 3, 3a,4,9,9a-hexahydro-1H-benzo(f)isoindole-3a-carboxylic acid;

methyl (3aRS,4SR,9SR,9aRS)-4,9-ethano-2-(2-(2-methoxyphenyl)propenoyl)-9-(3-thienyl)-2,3,3a,4,9,9a-hexahydro-1H-benzo(f)isoindole-3a-carboxylate; methyl (3aRS,4SR,9SR,9aRS)-4,9-ethano-9-(4-ethylphenyl)-2-(2-(2-methoxyphenyl)propenoyl)-2,3,3a,4,9,9a-hexahydro-1H-benzo(f)isoindole-3a-carboxylate;

(3aRS,4SR,9SR,9aRS)-4,9-ethano-9-(4-ethylphenyl)-2-(2-(2-methoxyphenyl)propenoyl)-2,3,3a,4,9,9a-hexahydro-1H-benzo(f)isoindole-3a-carboxylic acid; methyl (3aRS,4SR,9SR,9aRS)-9-(2,3-dihydrobenzofuran-5-yl)-4,9-ethano-2-(2-(2-methoxyphenyl)propenoyl)-2,3,3a,4,9,9a-hexahydro-1H-benzo(f)isoindole-3a-carboxylate;

methyl (3aRS,4SR,9SR,9aRS)-9-(2,3-dihydrobenzofuran-5-yl)-4,9-ethano-2-(2-(2-methoxyphenyl)propenoyl)-2,3,3a,4,9,9a-hexahydro-1H-benzo(fisoindole-3a-carboxylate;

(3aRS,4SR,9SR,9aRS)-9-(2,3-dihydrobenzofuran-5-yl)-4,9-ethano-2-(2-(2-methoxyphenyl)propenoyl))-2,3,3a,4,9,9a-hexahydro-1H-benzo(f)isoindole-3a-N-(3-pyridylmethyl)-carboxamide;

methyl (3aRS,4SR,9SR, 9aRS)-4,9-ethano-9-(4-fluorophenyl)-2-(2-(2-methoxyphenyl)propenoyl)-2,3,3a,4,9,9a-hexahydro-1H-benzo(f)isoindole-3a-carboxylate;

(3aRS,4SR,9SR,9aRS)-4,9-ethano-9-(4-fluorophenyl)-2-(2-(2-methoxyphenyl)propenoyl)-2,3,3a,4,9,9a-hexahydro-1H-benzo(f)isoindole-3a-carboxylic acid;

methyl (3aRS,4SR,9SR,9aRS)-9-(4-chloro-3-fluorophenyl)-4,9-ethano-2-(2-(2-methoxyphenyl)propenoyl)-2,3,3a,4,9,9a-hexahydro-1H-benzo(f)isoindole-3a-carboxylate;

(3aRS ,4SR,9SR,9aRS)-9-(4-chloro-3-fluorophenyl)4,9-ethano-2-(2-(2-methoxyphenyl)propenoyl)-2,3,3a,4,9, 9a-hexahydro-1H-benzo(f)isoindole-3a-carboxylic acid;

methyl (3aRS,4SR,9SR,9aRS)-4,9-ethano-2-(2-(2-methoxyphenyl)propenoyl)-9-(3-methylphenyl)-2,3,3a,4,9,9a-hexahydro-1H-benzo(Disoindole-3a-carboxylate;

(3aRS,4SR,9SR,9aRS)-4,9-ethano-2-(2-(2-methoxyphenyl)propenoyl)-9-(3-methylphenyl)-2,3,3a,4,9,9a-hexahydro-1H-benzo(f)isoindole-3a-carboxylic acid;

methyl (3aRS,4SR,9SR,9aRS)-9-(1,3-benzodioxol-5-yl)-4, 9-ethano-2-(2-(2-methoxyphenyl)propenoyl)-2,3,3a, 4,9,9a-hexahydro-1H-benzo(f)isoindole-3a-carboxylate;

methyl (3aRS,4SR,9SR,9aRS)-9-(3,4-dimethylphenyl)-4, 9-ethano-2(2-(2-methoxyphenyl)propenoyl)-2,3,3a,4, 9,9a-hexahydro-1H-benzo(fisoindole-3a-carboxylate;

(3aRS,4SR,9SR,9aRS)-9-(3,4-dimethylphenyl)-4,9-ethano-2(2-(2-methoxyphenyl)propenoyl)-2,3,3a,4,9, 9a-hexahydro-1H-benzo(f)isoindole-3a-carboxylic acid;

methyl (3aRS,4SR,9SR,9aRS)-4,9-ethano-9-(4-methoxyphenyl)-2-(2-(2-methoxyphenyl)propenoyl)-2,3,3a,4, 9,9a-hexahydro-1H-benzo(fisoindole-3a-carboxylate;

(3aRS,4SR,9SR,9aRS)-4,9-ethano-9-(4-methoxyphenyl)-2-(2-(2-methoxyphenyl)propenoyl)-2,3,3a,4,9,9a-hexahydro-1H-benzo(f)isoindole-3a-carboxylic acid;

(3aRS,4SR,9SR,9aRS)-4,9-ethano-9-(4-methoxyphenyl)-2-(2-(2-methoxyphenyl)propenoyl)-2,3,3a,4,9,9a-hexahydro-1H-benzo(f)isoindole-3a-N-(3-pyridylmethyl)carboxamide;

(3aRS,4SR,9SR,9aRS)-4,9-ethano-9-(4-methoxyphenyl)-2-(2-(2-methoxyphenyl)propenoyl)-2,3,3a,4,9,9a-hexahydro-1H-benzo(f)isoindole-3a-N'-phenylcarbohydrazide;

(3aRS,4SR,9SR,9aRS)-4,9-ethano-9-(4-methoxyphenyl)-2-(2-(2-methoxyphenyl)propenoyl)-2,3,3a,4,9,9a-hexahydro-1H-benzo(f)isoindole-3a-hydroxamic acid;

(3aRS,4SR,9SR,9aRS)4, 9-ethano-9-(4-methoxyphenyl)-2-(2-(2-methoxyphenyl)propenoyl)-2,3,3a,4, 9, 9a-hexahydro-1H-benzo(f)isoindole-3a-N'-(3-pyridyl) carbohydrazide;

(3aRS,4SR,9SR,9aRS)4,9-ethano-9-(4-methoxyphenyl)-2-(2-(2-methoxyphenyl)propenoyl)-2,3,3a,4,9,9a-hexahydro-1H-benzo(f)isoindole-3a-N-(3-thienylmethyl)carboxamide;

(RS)- and (SR)-2-{(3aRS,4SR,9SR,9aRS)4,9-ethano-9-(4-methoxyphenyl)-2-(2-(2-methoxyphenyl)propenoyl)-2,3,3a,4,9,9a-hexahydro-1H-benzo(f)isoindole-3a-carbonylamino}phenylacetic acids;

(3aRS,4SR,9SR,9aRS)4,9-ethano-2-(2-(2-methoxyphenyl)propenoyl)-9-(4-trifluoromethoxyphenyl)-2,3,3a,4,9,9,9a-hexahydro-1H-benzo(f)isoindole-3a-carboxylic acid;

methyl (3aRS,4SR,9SR,9aRS)-9-(3-bromophenyl)4,9-ethano-2-(2-(2-methoxyphenyl)-propenoyl)-2,3,3a,4,9,9a-hexahydro-1H-benzo(f)isoindole-3a-carboxylate;

(3aRS,4SR,9SR,9aRS)-9-(3-bromophenyl)4,9-ethano-2-(2-(2-methoxyphenyl)propenoyl)-2,3,3a,4,9,9a-hexahydro-1H-benzo(f)isoindole-3a-carboxylic acid;

methyl (3aRS,4SR,9SR,9aRS)4,9-ethano-9-(3-fluoro-phenyl-2-(2-(2-methoxyphenyl)-propenoyl)-2,3,3a,4,9,9a-hexahydro-1H-benzo(f)isoindole-3a-carboxylate;

(3aRS,4SR,9SR,9aRS)4,9-ethano-9-(3-fluorophenyl)-2-(2-(2-methoxyphenyl)propenoyl))-2,3,3a,4,9,9a-hexahydro-1H-benzo(f)isoindole-3a-carboxylic acid;

(3aRS,4SR,9SR,9aRS)-4,9-ethano-9-(3-fluorophenyl)-2-(2-(2-methoxyphenyl)propenoyl))-2,3,3a,4,9,9a-hexahydro-1H-benzo(f)isoindole-3a-(N-(3-pyridylmethyl)carboxamide;

methyl (3aRS,4SR,9SR,9aRS)-9-(3-chlorophenyl)-4,9-ethano-2-(2-(2-methoxyphenyl)-propenoyl)-2,3,3a,4,9,9a-hexahydro-1H-benzo(f)isoindole-3a-carboxylate;

(3aRS,4SR,9SR,9aRS)-9-(3-chlorophenyl)-4,9-ethano-2-(2-(2-methoxyphenyl)propenoyl)-2,3,3a,4,9,9a-hexahydro-1H-benzo(f)isoindole-3a-carboxylic acid;

(3aRS,4SR,9SR,9aRS)-9-(3-chlorophenyl)-4,9-ethano-2-(2-(2-methoxyphenyl)propenoyl))-2,3,3a,4,9,9a-hexahydro-1H-benzo(f)isoindole 3a-(N-(3-pyridylmethyl)carboxamide;

methyl (3aRS,4SR,9SR,9aRS)-9-(3-N,N-dimethylaminophenyl)-4,9-ethano-2-(2-(2-methoxyphenyl)propenoyl)-2,3,3a,4,9,9,9a-hexahydro-1H-benzo(f)isoindole-3a-carboxylate;

(3aRS,4SR,9SR, 9aRS)-9-(3-N,N-dimethylaminophenyl)4,9-ethano-2-(2-(2-methoxyphenyl)propenoyl)-2,3,3a,4,9,9,9a-hexahydro-1H-benzo(f)isoindole-3a-carboxylic acid;

methyl (3aRS,4SR,9SR,9aRS)-9-(3-aminophenyl)-4,9-ethano-2-(2-(2-methoxyphenyl)propenoyl)-2,3,3a,4,9,9,9a-hexahydro-1H-benzo(f)isoindole-3a-carboxylate hydrochloride;

methyl (3aRS,4SR,9SR,9aRS)-9-(4-N,N-dimethylaminophenyl)-4,9-ethano-2-(2-(2-methoxyphenyl)propenoyl)-2,3,3a,4,9,9,9a-hexahydro-1H-benzo(f)isoindole-3a-carboxylate;

(3aRS,4SR,9SR, 9aRS)-9-(4-cyanophenyl)-4, 9-ethano-2-(2-(2-methoxyphenyl)propenoyl)-2,3,3a,4,9,9,9a-hexahydro-1H-benzo(f)isoindole-3a-carboxylic acid;

methyl (3aRS,4SR,9SR,9aRS)-9-(3-cyanophenyl)-4,9-ethano-2-(2-(2-methoxyphenyl)propenoyl)-2,3,3a,4,9,9,9a-hexahydro-1H-benzo(fisoindole-3a-carboxylate;

(3aRS,4SR,9SR,9aRS)-4,9-ethano-9-(3-hydroxy-4-methoxyphenyl)-2-(2-(2-methoxyphenyl)propenoyl)-2,3,3a,4,9,9a-hexahydro-1H-benzo(fisoindole-3a-carboxylic acid;

methyl (3aRS,4SR,9SR,9aRS)-4,9-ethano-5-methoxy-2-(2-(2-methoxyphenyl)propenoyl)-9-(4-methylphenyl)-2,3,3a,4,9,9a-hexahydro-1H-benzo(f)isoindole-3a-carboxylate;

(3aRS,4SR,9SR,9aRS)-4,9-ethano-5-methoxy-2-(2-(2-methoxyphenyl) propenoyl)-9-(4-methylphenyl)-2,3,3a,4,9,9a-hexahydro-1H-benzo(fisoindole-3a-carboxylic acid;

(3aRS,4SR,9SR,9aRS)-4,9-ethano-2(2-(2-methoxyphenyl)propenoyl)-4-methyl-9-(4-methoxyphenyl)-2,3,3a,4,9,9a-hexahydro-1H-benzo(f)isoindole-3a-carboxylic acid;

(3aRS,4SR,9SR,9aRS)-9-(benzothien-2-yl)-4,9-ethano-2-(2-(2-methoxyphenyl)propenoyl))-2,3,3a,4,9,9a-hexahydro-1H-benzo(fisoindole-3a-carboxylic acid;

(3aRS,4SR,9SR,9aRS)-9-(2,4-dichlorophenyl)-4,9-ethano-2-(2-(2-methoxyphenyl)propenoyl))-2,3,3a,4,9,9a-hexahydro-1H-benzo(fisoindole-3a-carboxylic acid;

(3aRS,4SR,8SR,8aRS)-4,8-ethano-2-(2-(2-methoxyphenyl)propenoyl)-8-phenyl-2,3,3a,4,8,8a-hexahydro-1H-thieno(2,3-f)isoindole-3a-carboxylic acid; (3aRS,4SR,8SR,8aRS)-4,8-ethano-2-(2-(2-methoxyphenyl)propenoyl)-8-(4-methylphenyl)-2,3,3a,4,8,8a-hexahydro-1H-thieno(2,3-f)isoindole-3a-carboxylic acid;

(3aRS,4SR,8SR,8aRS)-4,8-ethano-2-(2-(2-methoxyphenyl)propenoyl)-8-(4-trifluoromethylphenyl)-2,3,3a,4,8,8a-hexahydro-1H-thieno(2,3-f)isoindole-3a-carboxylic acid;

(3aRS,4SR,8SR,8aRS)-N-benzyl-4,8-ethano-2-(2-(2-methoxyphenyl)propenoyl)-8-(4-trifluoromethylphenyl)-2,3,3a,4,8,8a-hexahydro-1H-thieno(2,3-f)isoindole-3a-carboxamide;

(3aRS,4SR,10SR,10aRS)-4,9-ethano-2-(2-(2-methoxyphenyl)propenoyl)-10-(4-methylphenyl)-2,3,3a,4, 10,10a-hexahydro-1H-indolo(2,3-f)isoindole-3a-carboxylic acid;

(3aRS,4SR,8SR,8aRS)-N-(3-pyridyl)methyl-4,8-ethano-2-(2-(2-methoxyphenyl)propenoyl)-8-(4-methylphenyl)-2,3,3a,4,8,8a-hexahydro-1H-thieno(2,3-f)isoindole-3a-carboxamide;

methyl (3aRS,4SR,8SR,8aRS)-4,8-ethano-8-(4-methoxyphenyl)-2-(2-(2-methoxyphenyl)propenoyl)-2,3,3a,4,8,8a-hexahydro-1H-thieno(2,3-f)isoindole-3a-carboxylate;

(3aRS,4SR,8SR,8aRS)4,8-ethano-8-(4-methoxyphenyl)-2-(2-(2-methoxyphenyl)propenoyl)-2,3,3a,4,8,8a-hexahydro-1H-thieno(2,3-f)isoindole-3a-carboxylic acid; and (3aRS,4SR,8SR,8aRS)-N-(3-pyridyl)methyl-8-(benzo-1,4-dioxan-6-yl)-4,8-ethano-2-(2-(2-methoxyphenyl)propenoyl)-2,3,3a,4,8,8a-hexahydro-1H-thieno(2,3-f)isoindole-3a-carboxamide;

wherein said compound is in the form of an optical isomer or a salt thereof.

4. A process for the preparation of a compound of formula (I) according to claim 3, wherein said compound of formula (I) is chosen from:

(3aRS,4SR,9SR,9aRS)-4,9-ethano-2-(2-(2-methoxyphenyl)propenoyl)-9-(4-methylphenyl)-2,3,3a,4,9,9a-hexahydro-1H-benzo(f)isoindole-3a-carboxylic acid;

(3aRS,4SR,9SR,9aRS-9-(benzothien-2-yl)-4,9-ethano-2-(2-(2-methoxyphenyl)propenoyl))-2,3,3a,4,9,9a-hexahydro-1H-benzo(f)isoindole-3a-carboxylic acid;

(3aRS,4SR,9SR,9aRS)-9-(2,4-dichlorophenyl)-4,9-ethano-2-(2-(2-methoxyphenyl)propenoyl))-2,3,3a,4,9,9a-hexahydro-1H-benzo(f)isoindole-3a-carboxylic acid;

(3aRS,4SR,9SR,9aRS)-9-(3,4-dichlorophenyl)4,9-ethano-2-(2-(2-methoxyphenyl)propenoyl)-2,3,3a,4,9,9a-hexahydro-1H-benzo(f)isoindole-3a-carboxylic acid;

(3aRS,4SR,9SR,9aRS)-9-(4-bromophenyl)4,9-ethano-2-(2-(2-methoxyphenyl)propenoyl)-2,3,3a,4,9,9a-hexahydro-1H-benzo(f)isoindole-3a-carboxylic acid;

(3aRS,4SR,9SR,9aRS)4,9-ethano-2-(2-(2-methoxyphenyl)propenoyl)-9-(4-chlorophenyl)-2,3,3a,4,9,9a-hexahydro-1H-benzo(f)isoindole-3a-carboxylic acid;

methyl (3aRS,4SR,9SR,9aRS)-9-(2,3-dihydrobenzofuran-5-yl)-4,9-ethano-2-(2-(2-methoxyphenyl)propenoyl)-2,3,3a,4,9,9a-hexahydro-1H-benzo(f)isoindole-3a-carboxylate; and (3aRS,4SR,8SR,8aRS)-4,8-ethano-2-(2-(2-methoxyphenyl)propenoyl)-8-(4-methylphenyl)-2,3,3a,4,8,8a-hexahydro-1H-thieno(2,3-f)isoindole-3a-carboxylic acid;

wherein said compound is in the form of an optical isomer or a salt thereof.

5. A process for the preparation of a compound of formula (I) according to claim 1, wherein said compound of formula (I) is obtained in the form of its dextrorotatory enantiomer.

6. A process according to claim 2, wherein:

in the definition of Ar, said phenyl radical is substituted at the 4 position by a methyl, trifluoromethyl or methoxy radical or a chlorine or bromine atom; or at least one of $R_1$ and $R_2$ are attached at the ortho position of the phenyl ring.

7. A process according to claim 1, wherein:

in the definition of $R_8$, said straight or branched alkyl radical having 1 to 6 carbon atoms is methyl; or in the definition of a

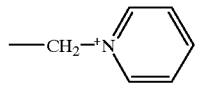

radical,
said anion is trifluoromethansulfonate; or said X is vinyidiyl.

8. A process according to claim 1, wherein:

in the definition of $R_8$, said straight or branched alkyl radical having 1 to 6 carbon atoms is methyl; and in the definition of a

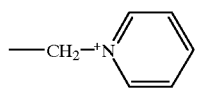

radical,
said anion is trifluoromethansulfonate; and said X is vinyldiyl.

9. A process according to claim 1, wherein:

in the definition of $R_8$, said straight or branched alkyl radical having 1 to 6 carbon atoms is methyl; and in the definition of a

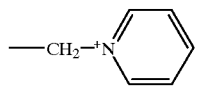

radical,
said anion is trifluoromethansulfonate.

10. A process according to claim 1, wherein:

in the definition of $R_8$, said straight or branched alkyl radical having 1 to 6 carbon atoms is methyl; and said X is vinyldiyl.

11. A process according to claim 1, wherein:

in the definition of a

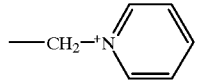

radical,
said anion is trifluoromethansulfonate; and said X is vinyldiyl.

12. A process according to claim 2, wherein:

in the definition of Ar, said phenyl radical is substituted at the 4 position by a methyl, trifluoromethyl or methoxy radical or a chlorine or bromine atom; and at least one of R. and $R_2$ are attached at the ortho position of the phenyl ring.

* * * * *

UNITED STATES PATENT AND TRADEMARK OFFICE
CERTIFICATE OF CORRECTION

PATENT NO. : 6,291,679 B1
DATED : September 18, 2001
INVENTOR(S) : Patrick Mailliet et al.

It is certified that error appears in the above-identified patent and that said Letters Patent is hereby corrected as shown below:

Title page,
Item [57], ABSTRACT,
Line 2, "benzoperhydroisindole" should read -- benzoperhydroisoindole --.

Column 53,
Line 56, "$R_8$is" should read -- $R_8$ is --.

Column 54,
Line 66, "haes" should read -- has --.

Column 55,
Line 42, "formula (1)" should read -- formula (I) --.
Lines 60-61, "formula (1)" should read -- formula (I) --.

Column 56,
Line 17, 37 and 38, "formula (1)" should read -- formula (I) --.
Line 45, "formula (XII)" should read -- formula (XIII) --.
Line 61, "A, R., $R_2$," should read -- A, $R_1$, $R_2$, --.

Column 57,
Lines 25, 29, 32, 40, 57, and 65, "benzo(fisoindole" should read -- benzo(f)isoindole --.

Column 58,
Lines 5, 12, 29, and 55, "benzo(fisoindole" should read -- benzo(f)isoindole --.
Line 21, "hexahydro-I H" should read -- hexahydro-1H --.

Column 59,
Line 7, "benzo(fisoindole" should read -- benzo(f)isoindole --.
Line 11, "benzo(fisoindole" should read -- benzo(f)isoindole --.
Line 18, "benzo(fisoindole" should read -- benzo(f)isoindole --.
Line 23, "benzo(fisoindole" should read -- benzo(f)isoindole --.
Line 30, "benzo(fisoindole" should read -- benzo(f)isoindole --.
Line 33, "benzo(Disoindole" should read -- benzo(f)isoindole --.
Line 58, "(4-chlorophenyl)4" should read -- (4-chlorophenyl)-4 --.
Linr 60, "benzo(Disoindole" should read -- benzo(f)isoindole --.

Column 60,
Line 25, "benzo(fisoindole" should read -- benzo(f)isoindole --.
Line 41, "(4-chloro-3-fluorophenyl)4" should read -- (4-chloro-3-fluorophenyl)-4 --.
Line 47, "benzo(Disoindole" should read -- benzo(f)isoindole --.

UNITED STATES PATENT AND TRADEMARK OFFICE
CERTIFICATE OF CORRECTION

PATENT NO. : 6,291,679 B1
DATED : September 18, 2001
INVENTOR(S) : Patrick Mailliet et al.

It is certified that error appears in the above-identified patent and that said Letters Patent is hereby corrected as shown below:

Column 60, cont'd,
Line 60, "benzo(fisoindole" should read -- benzo(f)isoindole --.
Line 67, "benzo(fisoindole" should read -- benzo(f)isoindole --.

Column 61,
Lines 16, 20, 24, and 28, "9aRS)4" should read -- 9aRS)-4 --.
Line 32, "(3-bromophenyl)4" should read -- (3-bromophenyl)-4 --.
Line 36, "(3-bromophenyl)4" should read -- (3-bromophenyl)-4 --.
Line 39, "9aRS)4" should read -- 9aRS)-4 --.
Line 42, "9aRS)4" should read -- 9aRS)-4 --.

Column 62,
Line 14, 18, 26, 34, and 38, "benzo(fisoindole" should read -- benzo(f)isoindole --.

Column 63,
Line 27, "(3,4-dichlorophenyl)4" should read -- (3,4-dichlorophenyl)-4 --.
Line 31, "(4-bromophenyl)4" should read -- (4-bromophenyl)-4 --.

Column 64,
Lines 9-10, "vinyidiyl" should read -- vinyldiyl --.
Line 57, "R. and $R_2$" should read -- $R_1$ and $R_2$ --.

Signed and Sealed this

Thirtieth Day of April, 2002

Attest:

*Attesting Officer*

JAMES E. ROGAN
*Director of the United States Patent and Trademark Office*